(12) United States Patent
Martin et al.

(10) Patent No.: US 7,671,060 B2
(45) Date of Patent: Mar. 2, 2010

(54) HETEROARYL BENZAMIDE DERIVATIVES

(75) Inventors: Nathaniel George Martin, Macclesfield (GB); Darren McKerrecher, Macclesfield (GB); Kurt Gordon Pike, Macclesfield (GB); Michael James Waring, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 18 days.

(21) Appl. No.: 11/924,888

(22) Filed: Oct. 26, 2007

(65) Prior Publication Data

US 2008/0318968 A1 Dec. 25, 2008

Related U.S. Application Data

(60) Provisional application No. 60/863,056, filed on Oct. 26, 2006, provisional application No. 60/957,370, filed on Aug. 22, 2007.

(51) Int. Cl.
A61K 31/4965 (2006.01)
(52) U.S. Cl. .................. 514/255.05; 544/336
(58) Field of Classification Search ............ 514/255.05; 544/336
See application file for complete search history.

(56) References Cited

U.S. PATENT DOCUMENTS

| | | | |
|---|---|---|---|
| 2,750,393 A | 6/1956 | Elpern | |
| 2,967,194 A | 1/1961 | Hauptschein | |
| 3,917,625 A | 11/1975 | Lee et al. | |
| 3,950,351 A | 4/1976 | Rossignol et al. | |
| 4,009,174 A | 2/1977 | Cluzan et al. | |
| 4,105,785 A | 8/1978 | Mauvernay et al. | |
| 4,146,631 A | 3/1979 | Ford et al. | |
| 4,434,170 A | 2/1984 | Dostert et al. | |
| 4,474,792 A | 10/1984 | Erickson | |
| 4,634,783 A | 1/1987 | Fujii et al. | |
| 4,966,891 A | 10/1990 | Fujiu et al. | |
| 5,258,407 A | 11/1993 | Washburn et al. | |
| 5,273,986 A | 12/1993 | Holland et al. | |
| 5,399,702 A | 3/1995 | Holland et al. | |
| 5,466,715 A | 11/1995 | Washburn et al. | |
| 5,510,478 A | 4/1996 | Sabb | |
| 5,661,153 A | 8/1997 | Isobe et al. | |
| 5,672,750 A | 9/1997 | Perry | |
| 5,712,270 A | 1/1998 | Sabb | |
| 5,849,735 A | 12/1998 | Albright et al. | |
| 6,110,945 A | 8/2000 | Head et al. | |
| 6,197,798 B1 | 3/2001 | Fink et al. | |
| 6,200,995 B1 | 3/2001 | De la Brouse-Elwood et al. | |
| 6,207,693 B1 | 3/2001 | Setoi et al. | |
| 6,214,878 B1 | 4/2001 | Bernardon et al. | |
| 6,242,474 B1 | 6/2001 | Yamasaki et al. | |
| 6,255,335 B1 | 7/2001 | Himmler et al. | |
| 6,316,482 B1 | 11/2001 | Setoi et al. | |
| 6,320,050 B1 | 11/2001 | Bizzarro et al. | |
| 6,348,474 B1 | 2/2002 | Kayakiri et al. | |
| 6,369,229 B1 | 4/2002 | Head et al. | |
| 6,376,515 B2 | 4/2002 | Zhu et al. | |
| 6,388,071 B2 | 5/2002 | Mahaney | |
| 6,448,399 B1 | 9/2002 | Corbett et al. | |
| 6,486,349 B1 | 11/2002 | Flitter et al. | |
| 6,528,543 B1 | 3/2003 | Bizzarro et al. | |
| 6,545,155 B2 | 4/2003 | Corbett et al. | |
| 6,610,846 B1 | 8/2003 | Bizzarro et al. | |
| 6,613,942 B1 | 9/2003 | Ling et al. | |
| 7,132,546 B2 | 11/2006 | Kato et al. | |
| 7,199,140 B2 | 4/2007 | Hayter et al. | |
| 7,230,108 B2 | 6/2007 | Hargreaves et al. | |
| 7,390,908 B2 | 6/2008 | Boyd et al. | |
| 7,524,957 B2 | 4/2009 | Boyd et al. | |
| 2001/0027200 A1 | 10/2001 | De la Brouse-Elwood et al. | |
| 2002/0002183 A1 | 1/2002 | Zhu et al. | |
| 2002/0095044 A1 | 7/2002 | Jagtap et al. | |
| 2003/0162690 A1 | 8/2003 | Zhu et al. | |
| 2003/0228982 A1 | 12/2003 | Helmke et al. | |
| 2004/0014968 A1 | 1/2004 | Bizzarro et al. | |
| 2004/0077555 A1 | 4/2004 | Ishihara et al. | |
| 2004/0214868 A1 | 10/2004 | Hayter et al. | |
| 2005/0080106 A1 | 4/2005 | Boyd et al. | |

(Continued)

FOREIGN PATENT DOCUMENTS

CA 2605738 11/2006

(Continued)

OTHER PUBLICATIONS

Jordan, V. C. Nature Reviews: Drug Discovery, 2, 2003, 205.*

(Continued)

Primary Examiner—James O Wilson
Assistant Examiner—Douglas M Willis
(74) Attorney, Agent, or Firm—Morgan Lewis & Bockius LLP

(57) ABSTRACT

The invention relates to a novel group of compounds of Formula (I) or a salt thereof:

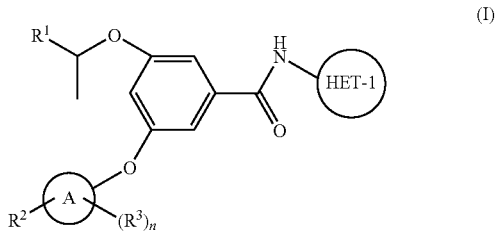

wherein $R^1$, $R^2$, $R^3$, n, A and HET-1 are as described in the specification, which may be useful in the treatment or prevention of a disease or medical condition mediated through glucokinase (GLK) such as type 2 diabetes. The invention also relates to pharmaceutical compositions comprising said compounds, methods of treatment of diseases mediated by GLK using said compounds and methods for preparing compounds of Formula (I).

3 Claims, 2 Drawing Sheets

U.S. PATENT DOCUMENTS

| | | |
|---|---|---|
| 2005/0148605 A1 | 7/2005 | Grotzfeld et al. |
| 2005/0165074 A1 | 7/2005 | Grotzfeld et al. |
| 2005/0171171 A1 | 8/2005 | Mehta et al. |
| 2005/0171172 A1 | 8/2005 | Lai et al. |
| 2005/0261315 A1 | 11/2005 | Mehta et al. |
| 2006/0004010 A1 | 1/2006 | Habashita et al. |
| 2006/0058353 A1 | 3/2006 | Mckerrecher et al. |
| 2006/0167053 A1 | 7/2006 | IIno et al. |
| 2006/0258728 A1 | 11/2006 | Tani et al. |
| 2007/0078168 A1 | 4/2007 | Caulkett |
| 2007/0093535 A1 | 4/2007 | Hayter et al. |
| 2007/0112040 A1 | 5/2007 | Hayter et al. |
| 2007/0255062 A1 | 11/2007 | Johnstone et al. |
| 2007/0287693 A1 | 12/2007 | Johnstone et al. |
| 2008/0015203 A1 | 1/2008 | Johnstone et al. |
| 2008/0057074 A1 | 3/2008 | Takaoka et al. |
| 2008/0153800 A1 | 6/2008 | Mccabe et al. |
| 2008/0171734 A1 | 7/2008 | Campbell et al. |
| 2008/0200694 A1 | 8/2008 | Cornwall et al. |
| 2008/0234273 A1 | 9/2008 | McKerrecher et al. |
| 2008/0280872 A1 | 11/2008 | Johnstone et al. |
| 2008/0280874 A1 | 11/2008 | Johnstone et al. |
| 2008/0300412 A1 | 12/2008 | Hopes et al. |
| 2008/0312207 A1 | 12/2008 | Johnstone et al. |
| 2008/0318968 A1 | 12/2008 | Martin et al. |
| 2009/0018157 A1 | 1/2009 | Johnstone et al. |
| 2009/0029905 A1 | 1/2009 | Mckerrecher et al. |
| 2009/0062351 A1 | 3/2009 | Caulkett et al. |
| 2009/0105214 A1 | 4/2009 | McKerrecher et al. |
| 2009/0105263 A1 | 4/2009 | Caulkett et al. |
| 2009/0111790 A1 | 4/2009 | Mckerrecher et al. |
| 2009/0118159 A1 | 5/2009 | McKerrecher et al. |
| 2009/0227592 A1 | 9/2009 | Boyd et al. |

FOREIGN PATENT DOCUMENTS

| | | |
|---|---|---|
| CS | 173097 | 6/1978 |
| EP | 0316704 | 5/1989 |
| EP | 0353452 | 2/1990 |
| EP | 0219436 | 12/1993 |
| EP | 0619116 | 10/1994 |
| EP | 1048659 | 11/2000 |
| EP | 1132381 | 9/2001 |
| EP | 0620216 | 1/2003 |
| EP | 1336607 | 8/2003 |
| EP | 1357116 | 10/2003 |
| EP | 1400540 | 3/2004 |
| EP | 1496052 | 1/2005 |
| EP | 1790637 | 5/2005 |
| EP | 1541563 | 6/2005 |
| EP | 1600442 | 11/2005 |
| EP | 1604981 | 12/2005 |
| EP | 1702919 | 9/2006 |
| EP | 1995246 | 11/2008 |
| FR | 1526074 | 5/1968 |
| FR | 2088019 | 1/1972 |
| GB | 1352415 | 5/1974 |
| GB | 1561350 | 2/1980 |
| GB | 1588242 | 4/1981 |
| GB | 2216517 | 10/1989 |
| GB | 2331748 | 6/1999 |
| GB | 2385328 | 8/2003 |
| JP | 50105559 | 8/1975 |
| JP | 57021320 | 2/1982 |
| JP | 57075962 | 5/1982 |
| JP | 58069812 | 4/1983 |
| JP | 61205937 | 9/1986 |
| JP | 62158252 | 7/1987 |
| JP | 04300832 | 10/1992 |
| JP | 04300874 | 10/1992 |
| JP | 06027025 | 2/1994 |
| JP | 08143565 | 6/1996 |
| JP | 08173525 | 7/1996 |
| JP | 08301760 | 11/1996 |
| JP | 09040557 | 2/1997 |
| JP | 09202786 | 8/1997 |
| JP | 10101671 | 4/1998 |
| JP | 10101672 | 4/1998 |
| JP | 10212271 | 8/1998 |
| JP | 11029480 | 2/1999 |
| JP | 11171848 | 6/1999 |
| JP | 11222435 | 8/1999 |
| JP | 11292879 | 10/1999 |
| JP | 2000086657 | 3/2000 |
| WO | WO 91/09017 | 6/1991 |
| WO | WO 94/04525 | 3/1994 |
| WO | WO 94/12461 | 6/1994 |
| WO | WO 95/20578 | 8/1995 |
| WO | WO 95/35298 | 12/1995 |
| WO | WO 96/11902 | 4/1996 |
| WO | WO 96/19455 | 6/1996 |
| WO | WO 96/22293 | 6/1996 |
| WO | WO 96/22295 | 6/1996 |
| WO | WO 96/22282 | 7/1996 |
| WO | WO 96/22294 | 7/1996 |
| WO | WO 96/36619 | 11/1996 |
| WO | WO 96/41795 | 12/1996 |
| WO | WO 97/24355 | 7/1997 |
| WO | WO 97/36480 | 10/1997 |
| WO | WO 97/46560 | 12/1997 |
| WO | WO 97/49707 | 12/1997 |
| WO | WO 97/49708 | 12/1997 |
| WO | WO 98/24771 | 6/1998 |
| WO | WO 98/34632 | 8/1998 |
| WO | WO 98/45242 | 10/1998 |
| WO | WO 99/00359 | 1/1999 |
| WO | WO 99/00372 | 1/1999 |
| WO | WO 99/17777 | 4/1999 |
| WO | WO 99/20611 | 4/1999 |
| WO | WO 99/24415 | 5/1999 |
| WO | WO 99/26944 | 6/1999 |
| WO | WO 99/32477 | 7/1999 |
| WO | WO 99/38845 | 8/1999 |
| WO | WO 99/54301 | 10/1999 |
| WO | WO 99/62901 | 12/1999 |
| WO | WO 00/02850 | 1/2000 |
| WO | WO 00/26202 | 5/2000 |
| WO | WO 00/39118 | 7/2000 |
| WO | WO 00/46203 | 8/2000 |
| WO | WO 00/58293 | 10/2000 |
| WO | WO 01/00579 | 1/2001 |
| WO | WO 01/12621 | 2/2001 |
| WO | WO 01/16097 | 3/2001 |
| WO | WO 01/19788 | 3/2001 |
| WO | WO 01/20327 | 3/2001 |
| WO | WO 01/26652 | 4/2001 |
| WO | WO 01/32639 | 5/2001 |
| WO | WO 01/44216 | 6/2001 |
| WO | WO 01/64642 | 9/2001 |
| WO | WO 01/64643 | 9/2001 |
| WO | WO 01/74791 | 10/2001 |
| WO | WO 01/83465 | 11/2001 |
| WO | WO 01/83478 | 11/2001 |
| WO | WO 01/85706 | 11/2001 |
| WO | WO 01/85707 | 11/2001 |
| WO | WO 02/00633 | 1/2002 |
| WO | WO 02/08209 | 1/2002 |
| WO | WO 02/14312 | 2/2002 |
| WO | WO 02/24682 | 3/2002 |
| WO | WO 02/26718 | 4/2002 |
| WO | WO 02/26731 | 4/2002 |
| WO | WO 02/28835 | 4/2002 |
| WO | WO 02/42270 | 5/2002 |
| WO | WO 02/46173 | 6/2002 |

| | | |
|---|---|---|
| WO | WO 02/48106 | 6/2002 |
| WO | WO 02/051831 | 7/2002 |
| WO | WO 02/064545 | 8/2002 |
| WO | WO 02/079145 | 10/2002 |
| WO | WO 03/000262 | 1/2003 |
| WO | WO 03/000267 | 1/2003 |
| WO | WO 03/015518 | 2/2003 |
| WO | WO 03/015774 | 2/2003 |
| WO | WO 03/022856 | 3/2003 |
| WO | WO 03/024222 | 3/2003 |
| WO | WO 03/026652 | 4/2003 |
| WO | WO 03/028641 | 4/2003 |
| WO | WO 03/047626 | 6/2003 |
| WO | WO 03/048152 | 6/2003 |
| WO | WO 03/051366 | 6/2003 |
| WO | WO 03/055482 | 7/2003 |
| WO | WO 03/066613 | 8/2003 |
| WO | WO 03/080585 | 10/2003 |
| WO | WO 03/082838 | 10/2003 |
| WO | WO 03/095438 | 11/2003 |
| WO | WO 03/097824 | 11/2003 |
| WO | WO 2004/002481 | 1/2004 |
| WO | WO 2004/007472 | 1/2004 |
| WO | WO 2004/022536 | 3/2004 |
| WO | WO 2004/031179 | 4/2004 |
| WO | WO 2004/045614 | 6/2004 |
| WO | WO 2004/046139 | 6/2004 |
| WO | WO 2004/050645 | 6/2004 |
| WO | WO 2004/052869 | 6/2004 |
| WO | WO 2004/063179 | 7/2004 |
| WO | WO 2004/063194 | 7/2004 |
| WO | WO 2004/072031 | 8/2004 |
| WO | WO 2004/072066 | 8/2004 |
| WO | WO 2004/076420 | 9/2004 |
| WO | WO 2004/080966 | 9/2004 |
| WO | WO 2004/081001 | 9/2004 |
| WO | WO 2004/085385 | 10/2004 |
| WO | WO 2004/085406 | 10/2004 |
| WO | WO 2004/110350 | 12/2004 |
| WO | WO 2004/110375 | 12/2004 |
| WO | WO 2005/042513 | 5/2005 |
| WO | WO 2005/044801 | 5/2005 |
| WO | WO 2005/048953 | 6/2005 |
| WO | WO 2005/049019 | 6/2005 |
| WO | WO 2005/054200 | 6/2005 |
| WO | WO 2005/054233 | 6/2005 |
| WO | WO 2005/056530 | 6/2005 |
| WO | WO 2005/063738 | 7/2005 |
| WO | WO 2005/066145 | 7/2005 |
| WO | WO 2005/080359 | 9/2005 |
| WO | WO 2005/080360 | 9/2005 |
| WO | WO 2005/090332 | 9/2005 |
| WO | WO 2005/095417 | 10/2005 |
| WO | WO 2005/095418 | 10/2005 |
| WO | WO 2005/103021 | 11/2005 |
| WO | WO 2005/121110 | 12/2005 |
| WO | WO 2005/123132 | 12/2005 |
| WO | WO 2006/016174 | 2/2006 |
| WO | WO 2006/016178 | 2/2006 |
| WO | WO 2006/016194 | 2/2006 |
| WO | WO 2006/030925 | 3/2006 |
| WO | WO 2006/040527 | 4/2006 |
| WO | WO 2006/040528 | 4/2006 |
| WO | WO 2006/040529 | 4/2006 |
| WO | WO 2006/066613 | 6/2006 |
| WO | WO 2006/114180 | 11/2006 |
| WO | WO 2006/125958 | 11/2006 |
| WO | WO 2006/125972 | 11/2006 |
| WO | WO 2007/007040 | 1/2007 |
| WO | WO 2007/007041 | 1/2007 |
| WO | WO 2007/007042 | 1/2007 |
| WO | WO 2007/017649 | 2/2007 |
| WO | WO 2007/028135 | 3/2007 |
| WO | WO 2007/030567 | 3/2007 |
| WO | WO 2007/031739 | 3/2007 |
| WO | WO 2007/053657 | 5/2007 |
| WO | WO 2007/060448 | 5/2007 |
| WO | WO 2007/105637 | 9/2007 |
| WO | WO 2008/050101 | 5/2008 |
| WO | WO 2008/050117 | 5/2008 |
| WO | WO 2008/075073 | 6/2008 |

OTHER PUBLICATIONS

Sarabu, R. Expert Opin. Ther. Patents, 18(7), 2008, 759-768.*
Hackam, et al. JAMA, 296(14), 2006, 1731-1732.*
Boucherle et al. "Recherches dans la serie des cetones polyphenoliques IV. Thiazoles" Chimica Therapeutica. 3(5):360-363 (1968) (Translation enclosed).
Bowden et al. "Structure-activity relations. Part 10. Metal-ion-complexation studies of a series of substituted benzamidotetrazoles" J. Chem. Research (Synopses) 11:304 (1991).
Bowden et al. "Structure-activity relations. Part 13. Inhibitors of cyclic nucleotide phosphodiesterase and anaphylaxis. Inhibition by a series of substituted benzamidotetrazoles" J. Chem. Research (Synopses) 6:206 (1992).
Brenner et al. "Imino-bridged heterocycles. VII. (1) N-aminobenzocycloheptapyridinimines" J. Heterocyclic Chem. 23:1331-1332 (1986).
Brocklehurst et al. "Stimulation of hepatocyte glucose metabolism by novel small molecule glucokinase activators" Diabetes 53:535-541 (2004).
Caro et al. "Liver glucokinase: Decreased activity in patients with type II diabetes" Horm. Metab. Res. 27(1):19-22 (1995).
Carroll et al. "The in vitro characterisation of a novel Glucokinase activator" Stress, Signalling and Control, Biochemical Society Meeting 679, University of Essex, UK (Jul. 2-4, 2003).
Caulfield et al. "The first potent and selective inhibitors of the glycine transporter type 2" J. Med. Chem. 44(17):2679-2682 (2001).
Cavier et al. "Recherches sur les derives nitres d'interet biologique. XVI. Relations entre structures et activites protozoocides, anthelminthiques et molluscicides dans la serie du benzamido-2 nitro-5 thiazole" European Journal of Medicinal Chemistry, Chimica Therapeutica 13(6): 539-543 (1978) (Translation enclosed).
Chemical Abstracts Service, Columbus, Ohio, US: CAS Registry No. 438028-05-8 (Nov. 15, 2001); CAS Registry No. 438024-90-9 (Nov. 15, 2001), [XP002272448].
Chemical Abstracts Service, Columbus, Ohio, US: CAS Registry No. 445284-93-5 (Jul. 9, 2002); CAS Registry No. 445250-52-2 (Jul. 9, 2002); CAS Registry No. 445030-98-8 (Jul. 9, 2002); CAS Registry No. 445017-74-3 (Jul. 9, 2002); CAS Registry No. 444935-78-8 (Jul. 9, 2002); CAS Registry No. 444923-81-3 (Jul. 9, 2002); CAS Registry No. 438222-80-1 (Jul. 9, 2002); CAS Registry No. 438221-01-3 (Jul. 9, 2002); CAS Registry No. 354550-59-7 (Jul. 9, 2002); CAS Registry No. 438537-80-5 (Jul. 9, 2002); CAS Registry No. 353770-14-6 (Jul. 9, 2002); CAS Registry No. 352690-95-0 (Jul. 9, 2002); CAS Registry No. 353478-21-4 (Jul. 9, 2002); CAS Registry No. 353477-20-0 (Jul. 9, 2002); CAS Registry No. 353474-36-9 (Jul. 9, 2002); CAS Registry No. 362473-72-1 (Jul. 9, 2002); CAS Registry No. 303140-37-6 (Jul. 9, 2002); [XP002272449].
Chemical Abstracts Service, Columbus, Ohio, US: CAS Registry No. 354767-51-4 (Sep. 5, 2001).
Chemical Abstracts Service, Columbus, Ohio, US: CAS Registry No. 354767-66-1 (Sep. 5, 2001).
Christesen et al. "The second activating glucokinase mutation (A456V): Implications for glucose homeostasis and diabetes therapy" Diabetes 51(4):1240-1246 (2002).
Ciaceri et al. "Analgesic, antipyretic and anti-inflammatory action of some new acids of the phenylethylenethiazole series" Minerva Medica 63(42):2409-2413 (1972).
Coburn et al. "Mesoionic purinone analogs IV: Synthesis and in vitro antibacterial properties of mesoionic thiazolo(3,2-α)pyrimidin-5,7-diones and mesoionic 1,3,4-thiadizolo(3,2-α)pyrimidin-5,7-diones" J. Pharm. Sciences. 62(11):1785-1789 (1973).
Coghlan "Small molecule Glucokinase Activators (GKAs) as novel anti-diabetic agents" CIDEM seminar (May 2005).

Coghlan "Small molecule Glucokinase Activators (GKAs) as novel anti-diabetic agents" Society for Medicines Research Seminar (Jun. 2004).

Coope et al. "Predictive blood glucose lowering efficacy by Glucokinase activators in high fat fed female Zucker rats" British Journal of Pharmacology 149(3):328-335 (2006).

Corbett "Glucokinase activators: Discovery of novel, orally active glucose lowering agents" Abstract, Cambridge Healthtech Institute's Eleventh Annual Molecular Medicine Tri-Conference, Moscone West Convention Center, San Francisco, CA (Mar. 24-26, 2004).

Corbett "Glucokinase activators: Discovery of novel, orally active glucose lowering agents" Presentation Slides, Cambridge Healthtech Institute's Eleventh Annual Molecular Medicine Tri-Conference, Moscone West Convention Center, San Francisco, CA (Mar. 24-26, 2004).

Cushman et al. "Synthesis and evaluation of new protein-tyrosine kinase inhibitors. Part 1. Pyridine-containing stilbenes and amides" Bioorganic & Medicinal Chemistry Letters 1(4):211-214 (1991).

De Paulis et al. "Potential antipsychotic agents. 6. Synthesis and antidopaminergic properties of substituted N-(1-benzyl-4-piperidinyl)salicylamides and related compounds. QSAR based design of more active members" Eur. J. Med. Chem. 25:507-517 (1990).

DeFronzo et al. "The triumvirate: β-cell, muscle, liver. A collusion responsible for NIDDM" Diabetes 37:667-687 (1988).

DeJohn et al. "Functionalization of Substituted 2(1H)- and 4(1H)-Pyridones. III. The preparation of substituted 6-vinyl-1,2-dihydro-2-oxo- and 1,4-dihydro-4-oxo-3-pyridinecarboxylic acids through the chemistry of pyridone dianions" J. Heterocyclic Chem. 20(5):1295-1302 (1983).

Desai et al. "Phenotypic correction of diabetic mice by adenovirus-mediated glucokinase expression" Diabetes 50:2287-2295 (2001).

Edmont et al. "Synthesis and evaluation of quinoline carboxyguanidines as antidiabetic agents" Bioorg. Med. Chem. Lett. 10(16):1831-1834 (2000).

Elpern et al. "Iodinated Benzamidotetrazoles" J. Org. Chem. 22:1686 (1957).

Ferre et al. "Correction of diabetic alterations by glucokinase" PNAS USA 93(14):7225-7230 (1996).

Ford et al. "Synthesis and quantitative structure-activity relationships of antiallergic 2-hydroxy-N-1H-tetrazol-5-ylbenzamides and N-(2-hydroxyphenyl)-1H-tetrazole-5-carboxamides" J. Med. Chem. 29(4):538-549 (1986).

Froguel et al. "Familial hyperglycemia due to mutations in glucokinase—Definition of a subtype of diabetes mellitus" New Engl. J. Med. 328:697-702 (1993).

Fujimoto et al. "Administration of D-glucosamine into the third cerebroventricle induced feeding accompanied by hyperglycemia in rats" Life Sciences 37(26):2475-2482 (1985).

Gill et al. "Stimulation of insulin release by a small molecule glucokinase activator" EASD Islet Study Group, Abstract (Nov. 2005).

Gill et al. "Stimulation of Insulin Release in MIN6 Cells and Isolated Rodent Islets by a Small Molecule Glucokinase Activator (GKA50)" Poster presented at 42nd EASD Meeting Copenhagen (2006) and Diabetologia vol. 49 (Supplement 1) 0501 (2006).

Gill et al. "Upregulation of key β-cell genes and improvement of function in rodent islets following chronic in vitro treatment with a glucokinase activator" Poster presented at 43rd EASD Meeting, Amsterdam (Sep. 17-21, 2007) and Diabetologia vol. 50 (Supplement 1) S218 (2007).

Glaser et al. "Familial hyperinsulinism caused by an activating glucokinase mutation" The New England Journal of Medicine 338(4):226-230 (1998).

Gorman et al. "Effect of high-fat diet on glucose homeostasis and gene expression in Glucokinase (GK) heterozygous knock-outs" 67th Annual Scientific Sessions, American Diabetes Association, Chicago, IL (Jun. 22-26, 2007).

Grimsby "Glucokinase activators: Potential treatment for type 2 diabetes" Roche, SMi Diabetes, London, UK (Oct. 28-29, 2002).

Grimsby et al. "Allosteric activators of glucokinase: Potential role in diabetes therapy" Science 301(5631):370-373 (2003).

Guertin et al. "Small molecule glucokinase activators as glucose lowering agents: A new paradigm for diabetes therapy" Current Medicinal Chemistry 13(15):1839-1843 (2006).

Hashimoto et al. "Evaluation of differentiation-inducing activity of retinoids on human leukemia cell lines HL-60 and NB4" Biol. Pharm. Bull. 19(10):1322-1328 (1996).

Hirst et al. "Molecular recognition of phosphate esters: A balance of hydrogen bonding and proton transfer interactions" Israel Journal of Chemistry 32:105-111 (1992).

Horsak et al. "Method of evaluation of the phase diagram of a system with formation of a compound" Chem. Zvesti. 36(3):311-320 (1982).

Isomura et al. "Z-type deposition of a polymerizable amphiphile to fabricate an immobilized LB film showing strong second harmonic generation" Thin Solid Films 244:939-942 (1994).

Johnson et al. "Glucose-dependent modulation of insulin secretion and intracellular calcium ions by GKA50—a glucokinase activator" 67th Annual Scientific Sessions, American Diabetes Association, Chicago, IL (Jun. 22-26, 2007).

Julia et al. "Synthesis of a 2,3,4,4a,5,6-hexahydrobenzo[f]quinoline system by "aryne substitution"" Bull Chem Soc France 11:4463-4467 (1968) (Translation enclosed).

Kamata et al. "Pyroelectricity of noncentrosymmetric Langmuir-Blodgett films of phenylpyrazine derivatives" Japan J. Appl. Phys. 33(2):1074-1078 (1994).

Kar "Cinchophen analogues as potential CNS agents" J Pharm Sci. 72(9):1082-1084 (1983).

Knoppova et al. "Synthesis and properties of 5-styryl-2-furancarboxlic acids" Collection Czechoslovak Chem. Commun. 46:2716-2728 (1981).

Konig et al. "Binding of heptanedioic acid to a threefold pyridine arylamide receptor. Enhancement of the stability of supramolecular solution structures by multiple binding sites" J. Org. Chem. 60(13):4291-4293 (1995).

Kunishima et al. "4-(4,6-Dimethoxy-1,3,5-triazin-2-yl)-4-methylmorpholinium chloride: An efficient condensing agent leading to the formation of amides and esters" Tetrahedron 55:13159-13170 (1999).

Kurata et al. "D-Glucose suppression of eating after intra-third ventricle infusion in rat" Physiology & Behavior 37:615-620 (1986).

Kurata et al. "Structural evaluation of glucose analogues on feeding elicitation in rat" Metabolism 38(1):46-51 (1989).

Lai et al. "Formation of columnar arrangements in copper(ii) complexes of 2-phenylazomethinopyridine derivatives" J. Materials Chemistry 8(11):2379-2383 (1998).

Leighton et al. "Improved glycemic control after sub-acute administration of a Glucokinase activator to male zucker (fa/fa) rats" 67th Annual Scientific Sessions, American Diabetes Association, Chicago, IL (Jun. 22-26, 2007).

Leighton et al. "Small molecule glucokinase activators as novel antidiabetic agents" Biochemical Society Transactions 33(Part 2):371-374 (2005).

Levin "Glucosensing neurons do more than just sense glucose" International Journal of Obesity 25(Suppl 5): S68-S72 (2001).

Levin et al. "Brain glucose sensing and body energy homeostasis: role in obesity and diabetes" Am. J. Physiol. 276(5 Pt 2):R1223-R1231 (1999).

Levin et al. "Differential effects of diet and obesity on high and low affinity sulfonylurea binding sites in the rat brain" Brain Research 739(1-2):293-300 (1996).

Alvarez et al. "Evidence that glucokinase regulatory protein is expressed and interacts with glucokinase in rat brain" J. Neurochem. 80(1):45-53 (2002).

Alvarez et al. "Expression of the glucagon-like peptide-1 receptor gene in rat brain" J. Neurochem. 66(3):920-927 (1996).

Anderson et al "Pyridopyrimidines. 6. Nucleophilic substitutions in the pyrido[2,3-d]pyrimidine series" J. Org. Chem. 42(6):993-996 (1977).

Ando et al. "Fluoride salts on alumina as reagents for alkylation of phenols and alcohols" Bull. Chem. Soc. Jpn. 55(8):2504-2507 (1982).

Atwell et al. "Potential antitumor agents. VI. Bisquaternary salts" J. Med. Chem. 11(2):295-300 (1968).

Baker et al. "Structure and synthesis of Pallescansin E utilising a modified Wadsworth-Emmons reaction" J. Chem. Soc., Perkin Trans. 1, 12:3087-3091 (1981).

Baker et al. "Synthesis of Pallescensin-E: Use of crown ether in the Wadsworth procedure for olefin founation" Tetrahedron Letters 22:161-162 (1981).

Balant et al. "Metabolic considerations in prodrug desing" Chapter twenty-three, Burger's Medicinal Chemistry and Drug Discovery, 5th Edition, vol. 1, NY: John Wiley & Sons, Inc. 949-982 (1995).

Beilstein Registry No. 6511458 (Apr. 18, 1994) [XP002272206].

Bell et al. "Glucokinase mutations, insulin secretion, and diabetes mellitus" Annu. Rev. Physiol. 58:171-186 (1996).

Beller et al. "Photochemical synthesis of benzo[f]quinolines" J Org Chem. 42(22):3514-3518 (1977).

Berl et al. "Induced fit selection of a barbiturate receptor from a dynamic structural and conformational/ configurational library" European J. Org. Chem. (11):3089-3094 (1999).

Berl et al. "Template-induced and molecular recognition directed hierarchical generation of supramolecular assemblies from molecular strands" Chem. Eur. J. 6(11):1938-1946 (2000).

Bonina et al. "Synthesis and pharmacologic activity of 20arylethenylthiazol-4-acetic and 4-carboxylic acids" II Farmaco 40(11):875-884 (1985).

Levin et al. "In vivo and in vitro regulation of [3H]glyburide binding to brain sulfonylurea receptors in obesity-prone and resistant rats by glucose" Brain Research 776(1-2):146-153 (1997).

Levin et al. "Reduced glucose-induced neuronal activation in the hypothalamus of diet-induced obese rats" Brain Research 808(2):317-319 (1998).

Levkoev et al. "Research on cyanide dyes 11. 7,7'-Dimethylthiacarbocyanines" Zhurnal Obshchei Khimii 27:3097-3107 (1957) (Translation enclosed).

Lynch et al. "Localization of glucokinase gene expression in the rat brain" Diabetes 49(5):693-700 (2000).

Mastafanova et al. "Features of the catalytic reduction of 4-(3-oxoquinuclidyl-2-methylene)-6-methoxyquinoline and its ethyleneketal" Khimiya Geterotsiklicheskikh Soedinenii (1):86-94 (1989) (Translation enclosed).

Mastafanova et al. "Synthesis and study of the antihypertensive activity of substituted N-acetylmercaptopropionyl-6-[2'-phenylethyl]pipecolinic acids" Khimiko Farmatsevticheskii Zhurnal 22(3):294-302 (1988).

Mastafanova et al. "Synthesis, Anti-Inflammatory and Analgesic Activity of 1,6-Disubstituted Pipecolic and 6-Substituted Picolinic Acids" Khimiko Farmatsevticheskii Zhurnal 22(4) 428-431 (1988).

Mazik et al. "Molecular recognition of carbohydrates by artificial receptors: systematic studies towards recognition motifs for carbohydrates" Chem. Eur. J. 7(3):664-670 (2001).

Mazik et al. "Molecular recognition of carbohydrates by artificial polypyridine and polypyrimidine receptors" Angewandte Chemie International Edition 39(3):551-554 (2000).

McKerrecher "Design and synthesis of novel glucokinase activators" 13th RSC-SCI Medicinal Chemistry Symposium, Churchill College, Cambridge (Sep. 4-7, 2005).

McKerrecher et al. "Design & synthesis of novel glucokinase activators as potential treatments for type 2 diabetes" 233rd ACS National Meeting, Chicago, IL (Mar. 25-29, 2007).

McKerrecher et al. "Design and synthesis of novel glucokinase activators as potential treatment for type 2 diabetes" Frontiers in Medicinal Chemistry, Frankfurt (Mar. 12-15, 2006).

McKerrecher et al. "Design of a potent, soluble glucokinase activator with excellent in vivo efficacy" Bioorg. Med. Chem. Lett. 16(10):2705-2709 (May 15, 2006) Epub Feb. 28, 2006.

McKerrecher et al. "Discovery, synthesis and biological evaluation of novel glucokinase activators" Bioorg Med Chem Lett. 15(8):2103-2106 (2005).

McKerrecher et al. "Identification of orally bioavailable small molecule activators of glucokinase" Abstract, 12th SCI-RSC Medicinal Chemistry Symposium, Cambridge, UK, Sep. 7-10, 2003 (poster 21) and 227th American Chemical Society National Meeting and Exposition, San Francisco, California, Mar. 28-Apr. 1, 2004 (paper 341).

McKerrecher et al. "Identification of orally bioavailable small molecule activators of glucokinase" Abstract, Anglo-Swedish Medicinal Chemistry Meeting (Mar. 2005).

Meijer et al "Chiral amplification in supramolecular stacks" Polymer Preprints 41(1):902-903 (2000).

Mobbs et al. "Brain glucose-sensing mechanisms: ubiquitous silencing by aglycemia vs. hypothalamic neuroendocrine responses" Am. J. Physiol. Endocrinol. Metab. 281(4):E649-E654 (2001).

Moore et al. "Acute fructose administration improves oral glucose tolerance in adults with type 2 diabetes" Diabetes Care 24(11):1882-1887 (2001).

Motesharei et al. "Molecular recognition in membrane mimics: A fluorescence probe" J. Am. Chem. Soc. 116(16):7413-7414 (1994).

Motesharei et al. "Molecular recognition on functionalized self-assembled monolayers of alkanethiols on gold" J. Am. Chem. Soc. 120(29): 7328-7336 (1998).

Palmans "Extended-core discotic liquid crystals based on the intramolecular H-bonding in N-acylated 2,2'-bipyridine3,3'-diamine moieties" Chem. Eur. J. 3(2):300-307 (1997).

Plieninger et al. "Synthesis of 7,8-dihydro-5,6-benzoquinoline-(3)-carboxylic acid" Chemische Berichte 87:882-887 (1954) (Translation enclosed).

Printz et al. "Mammalian glucokinase" Annu. Rev. Nutr. 13:463-496 (1993).

Prousek et al. "Preparation and electron transfer-induced cis-trans isomerization reactions of 1-(5-nitro-2-furyl)-, 1-(5-nitro-2-thienyl)-, and 1-(4-nitrophenyl)-2-R ethylenes" Collect. Czech. Chem. Commun. 54:1675-1682 (1989).

Qian-Cutrone et al. "Glucolipsin A and B, two new glucokinase activators produced by *Streptomyces purpurogeniscleroticus* and *Nocardia vaccinii*" Journal of Antibiotics (Tokyo), 52(3):245-255 (1999).

Rivalle et al. "2,3 Disubstituted furans and pyrroles—XVIII: Synthesis amid rearrangement of 4H-dihydro-9,10 benzo[4,5]cyclohepta[1,2-b]furannones-4" Tetrahedron 32(7):829-834 (1976).

Rogers et al. "Mesoionic purinone analogues as inhibitors of cyclic-AMP phosphodiesterase: a comparison of several ring systems" J. Med. Chem. 24(11):1284-1287 (1981).

Roncero et al. "Functional glucokinase isoforms are expressed in rat brain" J. Neurochem. 74(5):1848-1857 (2000).

Rowe et al. "Potassium channel dysfunction in hypothalamic glucose-receptive neurones of obese Zucker rats" Journal of Physiology 497.2:365-377 (1996).

Schuit et al. "Glucose sensing in pancreatic β-Cells. A model for the study of other glucose-regulated cells in gut, pancreas, and hypothalamus" Diabetes 50:1-11(2001).

Sekera et al. "No. 69.—Recherches sur les anesthesiques locaux (XI memoire) Synthese de quelques nouveaux β-alcoxyethoxycarbanilates et β-alcoxyethoxycinchonamides amines" Soc. Chim., 5th Series, Memoires 401-404 (1959) (Translation enclosed).

Seoane et al. "Glucokinase overexpression restores glucose utilization and storage in cultured hepatocytes from male Zucker diabetic fatty rats" J Biol Chem. 274(45):31833-31838 (1999).

Shiota et al. "Glucokinase gene locus transgenic mice are resistant to the development of obesity-induced type 2 diabetes" Diabetes 50(3):622-629 (2001).

Spanswick et al. "Insulin activates ATP-sensitive K+ channels in hypothalamic neurons of lean, but not obese rats" Nature Neuroscience 3(8):757-758 (2000).

Spanswick et al. "Leptin inhibits hypothalamic neurons by activation of ATP-sensitive potassium channels" Nature 390(6659):521-525 (1997).

Stout et al. "Synthesis and antiarrhythmic and parasympatholytic properties of substituted phenols. 3. Modifications to the linkage region (region 3)" J. Med. Chem. 28(3):295-298 (1985).

Suhua et al. "Synthesis and biological activity of tyrosine protein kinase inhibitors" Acta Pharmaceutica Sinica 32(7): 515-523 (1997).

Tecilla et al. "Hydrogen-bonding self-assembly of multichromophore structures" J. Am. Chem. Soc. 112:9408-9410 (1990).

Tecilla et al. "Synthetic hydrogen bonding receptors as models of transacylase enzymes" Tetrahedron 51(2):435-448 (1995).

Tecilla et al. "Transition-state stabilization and molecular recognition: acceleration of phosphoryl-transfer reactions by an artificial receptor" J. Am. Chem. Soc. 112:9586-9590 (1990).

Tornetta et al. "Arylvinylthiazole derivatives with anti-inflammatory, analgesic and anti-pyretic activity" Bollettino Delle Sedute Accad. Giovenia Sci. Nat. Catanica. Series 6, 11(9-10):89-95 (1973) (Translation enclosed).

Tucker et al. "Novel Inhibitors of prolyl 4-hydroxylase. 2. 5-amide substituted pyridine-2-carboxylic acids" J. Med. Chem. 3(5)5:804-807 (1992).

Van Gorp et al. "C3-symmetrical supramolecular architectures: fibers and organic gels from discotic trisamides and trisureas" J Am. Chem. Soc. 124(49):14759-14769 (2002).

Vanderstelt et al. "Synthesis and pharmacological properties of some derivatives of 5H-benzo[4,5] cyclohepta[1,2-b] pyridine and of 11H-benzo[5,6] cyclohepta[1,2-c] pyridine III" Arzneim. Forsch. 22(1):133-137 (1972).

Velho et al. "Impaired hepatic glycogen synthesis in glucokinase-deficient (MODY-2) subjects" J. Clin. Invest. 98(8):1755-1761 (1996).

Vertigan et al. "Impact of cell glycogen content on modulation of hepatocyte glucose metabolism by pharmacological agents" Diabetologia, 47 Supp 1, A 214, 589 (2004).

Williams et al. "Meeting the needs of type 2 diabetes patients" Highlights from the society for medicines research symposium type II diabetes: Mechanisms and emerging therapeutic targets, held Jun. 17, 2004, in London, United Kingdom, Drug News and Perspectives, 17(8) 1-4 (Oct. 2004).

Winzell et al. "Glucokinase Activation Reduces Glycemia and Improves Glucose Tolerance in Mice with High-fat Diet-induced Insulin Resistance" 67th Annual Scientific Sessions, American Diabetes Association, Chicago, IL (Jun. 22-26, 2007) and Diabetes vol. 56 (Supplement 1) 1482-P (2007).

Yakushijin et al. "Intramolecular ring formation of phenyl azide and furan" Heterocycles 12(8):1021-1026 (1979).

Yakushijin et al. "Intramolecular ring formation of phenyl azide and furan moieties" Chem. Pharm. Bull. 30(1):140-151 (1982).

Yang et al. "Hypothalamic glucose sensor similarities to and differences from pancreatic beta-cell mechanisms" Diabetes 48(9):1763-1772 (1999).

Yoshina et al. "Studies of heterocyclic compounds. II. Synthesis of 2-furylvinyl-benzenes and studies of polarography" Yakugaku Zasshi 88(4):398-404 (1968).

Yoshina et al. "Studies of heterocyclic compounds. III. Synthesis of methyl 5-(2-phenylvinyl)2-furoate" Yakugaku Zasshi 88(4):405-409 (1968).

Yoshina et al. "Studies of heterocyclic compounds. IV. Ultraviolet specta of 2-(2-furyl)vinylbenzenes and 2-(2-furyl)vinylfurans" Yakugaku Zasshi 88(4):410-416 (1968).

Yoshina et al. "Studies of heterocyclic compounds. VI. 2-(Carbomethoxy-2-furyl)vinyl benzenes and their utraviolet specta" Yakugaku Zasshi 88(4):977-983 (1968).

Youssefyeh et al. "Development of high-affinity 5-HT3 receptor antagonists. 1. Initial structure-activity relationship of novel benzamides" J. Med. Chem. 35(5): 895-903 (1992).

Zhang et al. "Synthesis based on affinity separation (SAS): separation of products having barbituric acid tag from untagged compounds by using hydrogen bond interaction" Synlett 5:590-596 (2001).

Coghlan et al. "Glucokinase activators in diabetes management" Expert Opin. Investig. Drugs 17(2):145-167 (2008).

Coghlan et al., "Glucokinase activators in diabetes management" Expert Opin. Investig. Drugs 17(2):145-167 (2008).

Leighton, "Pre-clinical disease models—challenges and success stories" 44th Drug Information Association Annual Meeting, Boston, MA, US (2008).

Lith, "Evaluation of the effects on whole body glucose metabolism after single doses of X2000—A glucose lowering agent" Poster presentation, Master thesis in Pharmaceutical Bioscience, Goteborgs University (2008).

Ralph et al. "Glucose Modulation of Glucokinase Activation by Small Molecules" Biochemistry 47(17):5028-5036 (2008).

Sarabu et al., "Glucokinase activators as new type 2 diabetes therapeutic agents" Expert Opinion on Therapeutic Patents 18(7):759-768 (2008).

Shorvon, "Pyrrolidone derivatives" Lancet 358(9296):1885-1892 (2001).

Eycken et al., Synthesis of (E)-5-(2-arylvinyl)-2-(hetero)arylpyridines, (E)-2-(2-arylvinyl)-5-methoxycarbonylpyridines and (E,E)-2,5-bis(2-arylvinyl)pyridines as polarity and pH probes, 2002, J. Chem. Soc., Perkin. Trans. 2, p. 929.

Robertson et al. "Structure-activity relationships of arylimidazopyridine cardiotonics: discovery and inotropic activity of 2-[2-methoxy-4-(methylsulfinyl)phenyl]-1H-imidazo[4,5-c]pyridine" Journal of Medicinal Chemistry 28:717-727 (1985).

West, Anthony R., "Solid State Chemistry and its Applications" Wiley, New York, pp. 358 and 365 (1988).

Wolff, Manfred E. "Burger's Medicinal Chemistry", 5th Edition, Part I, John Wiley & Sons, pp. 975-977 (1995).

Takagi et al. "Studies on metabolic fate of 3,4,5-trimethoxy-N-(3-piperidyl)benzamide(KU-54). (2). Metabolism in rats" Accession No. 1984:503556 HCAPLUS, Abstract of Oyo Yakuri 27(6):1167-1174 (1984).

* cited by examiner

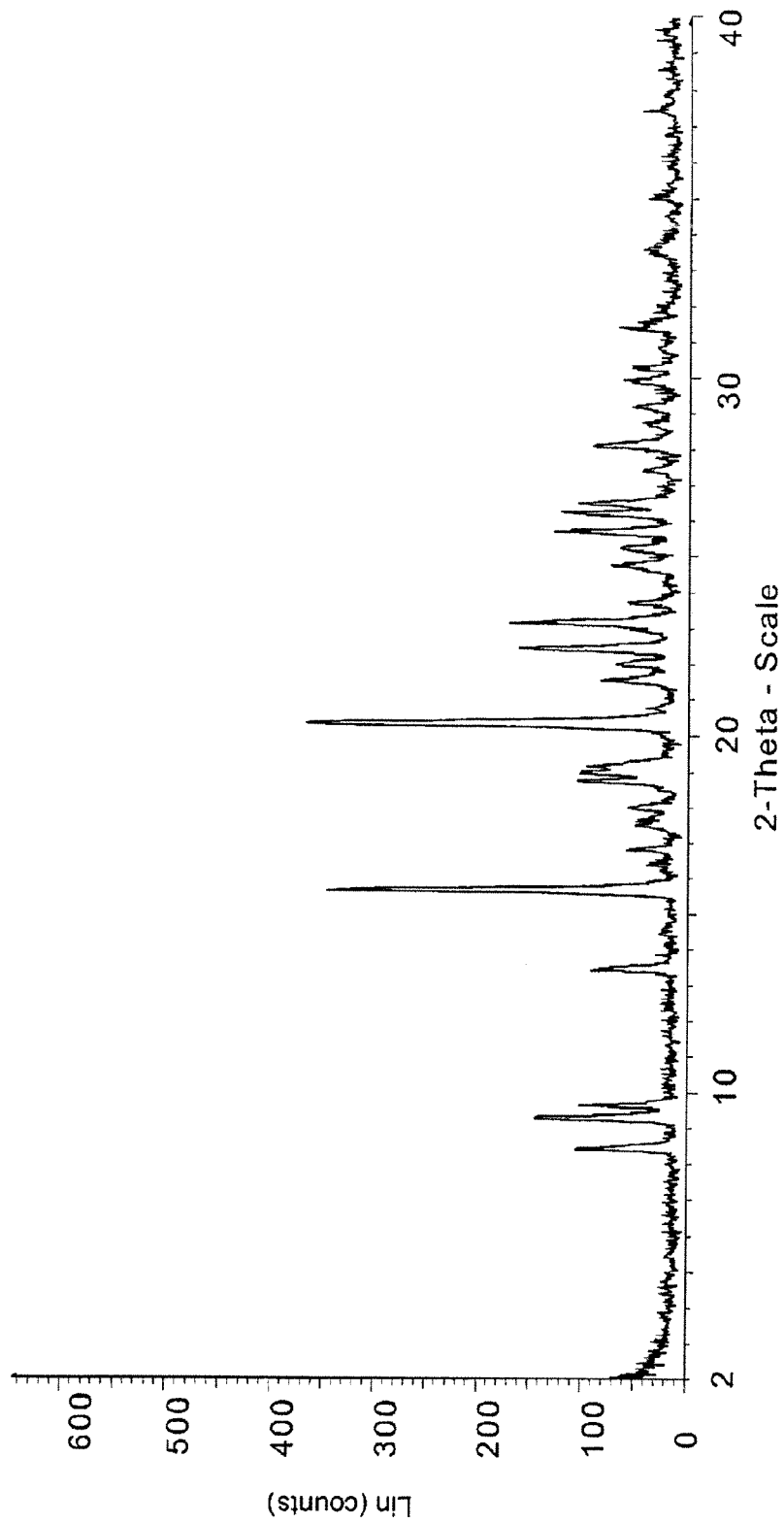
Figure A: X-Ray Powder Diffraction Pattern 5-[3-[(2S)-1-(difluoromethoxy)propan-2-yl]oxy-5-[(5-methylpyrazin-2-yl)carbamoyl]phenoxy]-N,N-dimethyl-pyrazine-2-carboxamide Form A

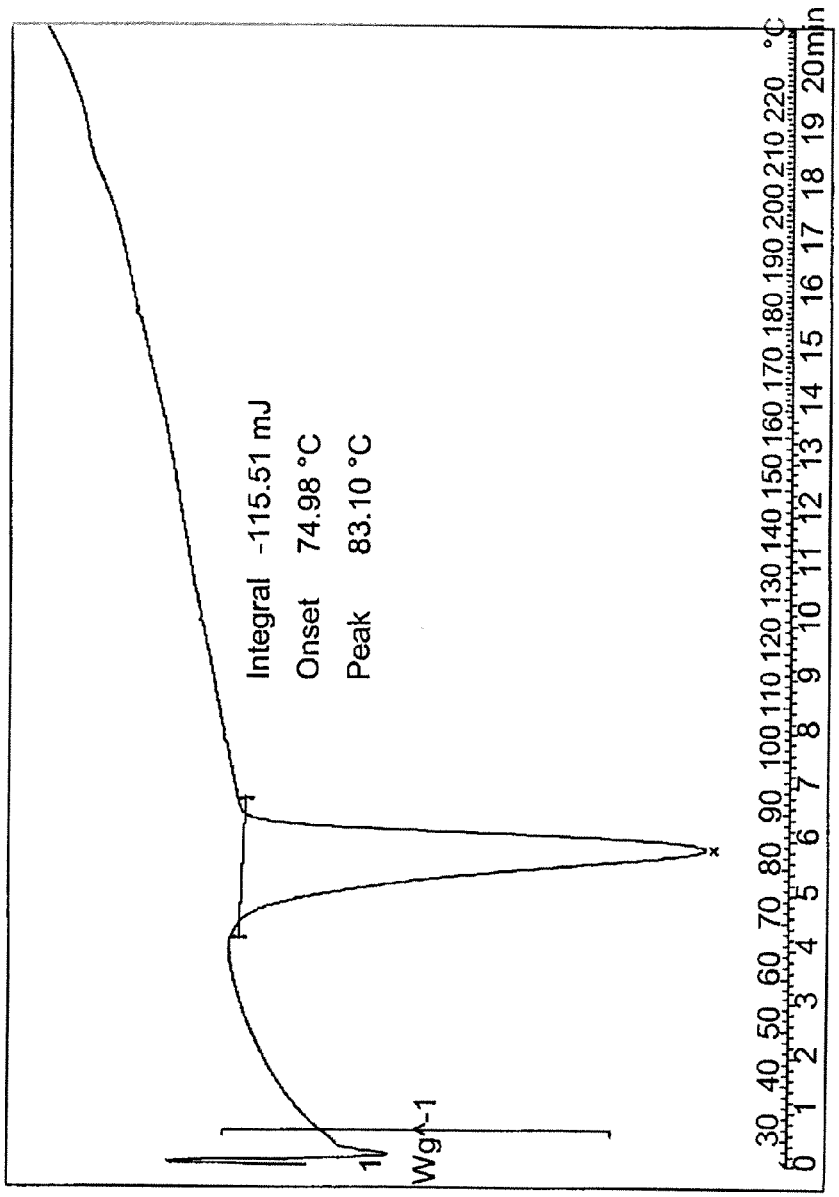
Figure B: DSC Thermogram 5-[3-[(2S)-1-(difluoromethoxy)propan-2-yl]oxy-5-[(5-methylpyrazin-2-yl)carbamoyl]phenoxy]-N,N-dimethyl-pyrazine-2-carboxamide Form A

HETEROARYL BENZAMIDE DERIVATIVES

This application claims the benefit under 35 U.S.C §119(e) of Application No. 60/863,056, U.S. filed on 26 Oct. 2007 and of Application No. 60/957,370 filed on 22 Aug. 2006.

The present invention relates to a group of benzoyl amino heterocyclyl compounds which are useful in the treatment or prevention of a disease or medical condition mediated through glucokinase (GLK or GK), leading to a decreased glucose threshold for insulin secretion. In addition the compounds are predicted to lower blood glucose by increasing hepatic glucose uptake. Such compounds may have utility in the treatment of Type 2 diabetes and obesity. The invention also relates to pharmaceutical compositions comprising said compounds and to methods of treatment of diseases mediated by GLK using said compounds.

In the pancreatic β-cell and liver parenchymal cells the main plasma membrane glucose transporter is GLUT2. Under physiological glucose concentrations the rate at which GLUT2 transports glucose across the membrane is not rate limiting to the overall rate of glucose uptake in these cells. The rate of glucose uptake is limited by the rate of phosphorylation of glucose to glucose-6-phosphate (G-6-P) which is catalysed by glucokinase (GLK) [1]. GLK has a high (6-10 mM) Km for glucose and is not inhibited by physiological concentrations of G-6-P [1]. GLK expression is limited to a few tissues and cell types, most notably pancreatic β-cells and liver cells (hepatocytes) [1]. In these cells GLK activity is rate limiting for glucose utilisation and therefore regulates the extent of glucose induced insulin secretion and hepatic glycogen synthesis. These processes are critical in the maintenance of whole body glucose homeostasis and both are dysfunctional in diabetes [2].

In one sub-type of diabetes, Maturity-Onset Diabetes of the Young Type 2 (MODY-2), the diabetes is caused by GLK loss of function mutations [3,4]. Hyperglycaemia in MODY-2 patients results from defective glucose utilisation in both the pancreas and liver [5]. Defective glucose utilisation in the pancreas of MODY-2 patients results in a raised threshold for glucose stimulated insulin secretion. Conversely, rare activating mutations of GLK reduce this threshold resulting in familial hyperinsulinism [6, 6a, 7]. In addition to the reduced GLK activity observed in MODY-2 diabetics, hepatic glucokinase activity is also decreased in type 2 diabetics [8]. Importantly, global or liver selective overexpression of GLK prevents or reverses the development of the diabetic phenotype in both dietary and genetic models of the disease [9-12]. Moreover, acute treatment of type 2 diabetics with fructose improves glucose tolerance through stimulation of hepatic glucose utilisation [13]. This effect is believed to be mediated through a fructose induced increase in cytosolic GLK activity in the hepatocyte by the mechanism described below [13].

Hepatic GLK activity is inhibited through association with GLK regulatory protein (GLKRP). The GLK/GLKRP complex is stabilised by fructose-6-phosphate (F6P) binding to the GLKRP and destabilised by displacement of this sugar phosphate by fructose-1-phosphate (F1P). F1P is generated by fructokinase mediated phosphorylation of dietary fructose. Consequently, GLK/GLKRP complex integrity and hepatic GLK activity is regulated in a nutritionally dependent manner as F6P is dominant in the post-absorptive state whereas F1P predominates in the post-prandial state. In contrast to the hepatocyte, the pancreatic β-cell expresses GLK in the absence of GLKRP. Therefore, β-cell GLK activity is regulated extensively by the availability of its substrate, glucose. Small molecules may activate GLK either directly or through destabilising the GLK/GLKRP complex. The former class of compounds are predicted to stimulate glucose utilisation in both the liver and the pancreas whereas the latter are predicted to act selectively in the liver. However, compounds with either profile are predicted to be of therapeutic benefit in treating Type 2 diabetes as this disease is characterised by defective glucose utilisation in both tissues.

GLK, GLKRP and the $K_{ATP}$ channel are expressed in neurones of the hypothalamus, a region of the brain that is important in the regulation of energy balance and the control of food intake [14-18]. These neurones have been shown to express orectic and anorectic neuropeptides [15, 19, 20] and have been assumed to be the glucose-sensing neurones within the hypothalamus that are either inhibited or excited by changes in ambient glucose concentrations [17, 19, 21, 22]. The ability of these neurones to sense changes in glucose levels is defective in a variety of genetic and experimentally induced models of obesity [23-28]. Intracerebroventricular (icv) infusion of glucose analogues, that are competitive inhibitors of glucokinase, stimulate food intake in lean rats [29, 30]. In contrast, icv infusion of glucose suppresses feeding [31]. Thus, small molecule activators of GLK may decrease food intake and weight gain through central effects on GLK. Therefore, GLK activators may be of therapeutic use in treating eating disorders, including obesity, in addition to diabetes. The hypothalamic effects will be additive or synergistic to the effects of the same compounds acting in the liver and/or pancreas in normalising glucose homeostasis, for the treatment of Type 2 diabetes. Thus the GLK/GLKRP system can be described as a potential "Diabesity" target (of benefit in both Diabetes and Obesity).

GLK is also expressed in specific entero-endocrine cells where it is believed to control the glucose sensitive secretion of the incretin peptides GIP (glucose-dependent insulinotropic polypeptide) and GLP-1 (Glucagon-Like Peptide-1) from gut K-cells and L-cells respectively (32, 33, 34). Therefore, small molecule activators of GLK may have additional beneficial effects on insulin secretion, b-cell function and survival and body weight as a consequence of stimulating GIP and GLP-1 secretion from these entero-endocrine cells.

In WO00/58293 and WO01/44216 (Roche), a series of benzylcarbamoyl compounds are described as glucokinase activators. The mechanism by which such compounds activate GLK is assessed by measuring the direct effect of such compounds in an assay in which GLK activity is linked to NADH production, which in turn is measured optically—see details of the in vitro assay described hereinafter. Compounds of the present invention may activate GLK directly or may activate GLK by inhibiting the interaction of GLKRP with GLK.

Further GLK activators have been described in WO03/095438 (substituted phenylacetamides, Roche), WO03/055482 (carboxamide and sulphonamide derivatives, Novo Nordisk), WO2004/002481 (arylcarbonyl derivatives, Novo Nordisk), and in WO03/080585 (amino-substituted benzoylaminoheterocycles, Banyu).

Our International application Number: WO03/000267 describes a group of benzoyl amino pyridyl carboxylic acids which are activators of the enzyme glucokinase (GLK).

Our International application Number: WO03/015774 describes compounds of the Formula (A):

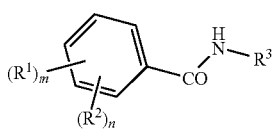

wherein R³ is phenyl or a substituted heterocycle other than a carboxylic acid substituted pyridyl.

International application WO2004/076420 (Banyu) describes compounds which are generally a subset of those described in WO03/015774, wherein for example R¹ is an (substituted) alkyl ether and R² is (substituted) phenoxy.

We have surprisingly found a small group of compounds, generally a selected subgroup of those described in WO 03/015774, which have generally superior potency for the GLK enzyme, and more advantageous physical properties, including, for example, higher aqueous solubility, higher permeability, and/or lower plasma protein binding. Consequently, such compounds having a balance of these properties would be expected to display higher plasma free drug levels and superior in vivo efficacy after oral dosing as determined, for example, by activity in Oral Glucose Tolerance Tests (OGTTs). Therefore this group of compounds would be expected to provide superior oral exposure at a lower dose and thereby be particularly suitable for use in the treatment or prevention of a disease or medical condition mediated through GLK. The compounds of the invention may also have superior potency and/or advantageous physical properties (as described above) and/or favourable toxicity profiles and/or favourable metabolic profiles in comparison with other GLK activators known in the art, as well as those described in WO 03/015774.

Thus, according to the first aspect of the invention there is provided a compound of Formula (I):

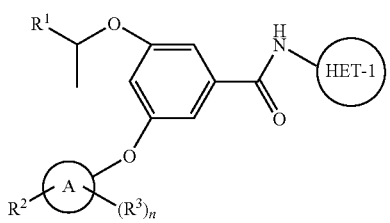

wherein:
R¹ is selected from fluoromethoxymethyl, difluoromethoxymethyl and trifluoromethoxymethyl;
R² is a substituent on a carbon atom of Ring A and is selected from —C(O)NR⁴R⁵, —SO₂NR⁴R⁵, —S(O)$_p$R⁴ and HET-2;
HET-1 is a 5-or 6-membered, C-linked heteroaryl ring containing a nitrogen atom in the 2-position relative to the amide nitrogen to which the ring is attached and optionally 1 or 2 further ring heteroatoms independently selected from O, N and S; which ring is optionally substituted on an available carbon atom, or on a ring nitrogen atom provided it is not thereby quaternised, with 1 or 2 substituents independently selected from R⁶;
HET-2 is a 4-, 5-or 6-membered, C-or N-linked heterocyclyl ring containing 1, 2, 3 or 4 heteroatoms independently selected from O, N and S, wherein a —CH₂— group can optionally be replaced by a —C(O)—, and wherein a sulphur atom in the heterocyclic ring may optionally be oxidised to a S(O) or S(O)₂ group, which ring is optionally substituted on an available carbon or nitrogen atom by 1 or 2 substituents independently selected from R⁷;
R³ is a substituent on a carbon atom of Ring A and is selected from halo;
R⁴ is selected from hydrogen, (1-4C)alkyl [optionally substituted by 1 or 2 substituents independently selected from HET-2, —OR⁵, —SO₂R⁵, (3-6C)cycloalkyl (optionally substituted with 1 group selected from R⁷) and —C(O)NR⁵R⁵], (3-6C)cycloalkyl (optionally substituted with 1 group selected from R⁷) and HET-2;
R⁵ is hydrogen or (1-4C)alkyl;
R⁶ is independently selected from (1-4C)alkyl, hydroxy(1-4C)alkyl, (1-4C)alkoxy(1-4C)alkyl, (1-4C)alkylS(O)$_p$(1-4C)alkyl, amino(1-4C)alkyl, (1-4C)alkylamino(1-4C)alkyl, di(1-4C)alkylamino(1-4C)alkyl, and/or (for R⁶ as a substituent on carbon) halo;
R⁷ is selected from (1-4C)alkyl, —C(O)(1-4C)alkyl, —C(O)NR⁴R⁵, (1-4C)alkoxy(1-4C)alkyl, hydroxy(1-4C)alkyl, —S(O)$_p$R⁵ and/or (for R⁷ as a substituent on carbon) hydroxy and (1-4C)alkoxy;
Ring A is a 5-or 6-membered heteroaryl ring, containing 1, 2 or 3 ring hetereoatoms independently selected from O, S and N; which ring optionally further substituted on an available nitrogen atom (provided it is not thereby quaternised) by a substituent selected from R⁸;
R⁸ is selected from (1-4C)alkyl, (3-6C)cycloalkyl, hydroxy(1-4C)alkyl, (1-4C)alkoxy(1-4C)alkyl, —C(O)(1-4C)alkyl, benzyl, and (1-4C)alkylsulfonyl;
p is (independently at each occurrence) 0, 1 or 2;
n is 0, 1 or 2;
or a salt thereof.

It will be understood that when R⁴ is (1-4C)alkyl substituted with —C(O)NR⁵R⁵, each R⁵ is independently selected from hydrogen and (1-4C)alkyl, and therefore this definition of R⁴ includes (but is not limited to) (1-4C)alkyl substituted with —CONH₂, —CONHMe, —CONMe₂ or —CONMeEt.

It will be understood that where a compound of the formula (I) contains more than one HET-2 ring, they may be the same or different.

It will be understood that where a compound of the formula (I) contains more than one group R⁴, they may be the same or different.

It will be understood that where a compound of the formula (I) contains more than one group R⁵, they may be the same or different.

It will be understood that where a compound of the formula (I) contains more than one group R³, they may be the same or different.

A similar convention applies for all other groups and substituents on a compound of formula (I) as hereinbefore defined.

Compounds of Formula (I) may form salts which are within the ambit of the invention. Pharmaceutically-acceptable salts are preferred although other salts may be useful in, for example, isolating or purifying compounds.

In another aspect, the invention relates to compounds of formula (I) as hereinabove defined or to a pharmaceutically-acceptable salt.

In another aspect, the invention relates to compounds of formula (I) as hereinabove defined or to a pro-drug thereof. Suitable examples of pro-drugs of compounds of formula (I) are in-vivo hydrolysable esters of compounds of formula (I).

Therefore in another aspect, the invention relates to compounds of formula (I) as hereinabove defined or to an in-vivo hydrolysable ester thereof.

In this specification the generic term "alkyl" includes both straight-chain and branched-chain alkyl groups. However references to individual alkyl groups such as "propyl" are specific for the straight chain version only and references to individual branched-chain alkyl groups such as t-butyl are specific for the branched chain version only. For example, "(1-4C)alkyl" includes methyl, ethyl, propyl, isopropyl and t-butyl. An analogous convention applies to other generic terms.

For the avoidance of doubt, reference to the group HET-1 containing a nitrogen in the 2-position, is intended to refer to the 2-position relative to the amide nitrogen atom to which the group is attached. For example, the definition of formula (I) encompasses (but is not limited to) the following structures:

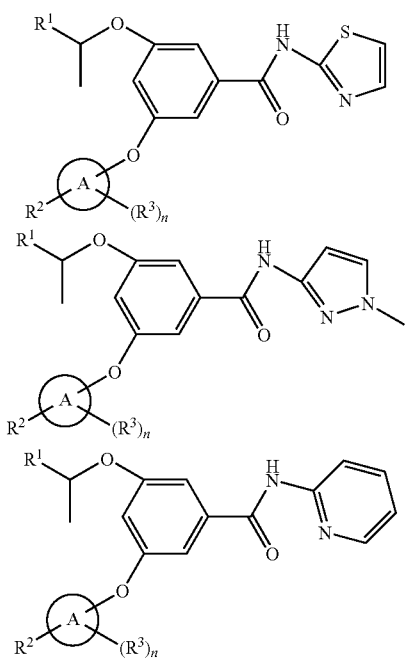

Suitable examples of HET-1 as a 5-or 6-membered, C-linked heteroaryl ring as hereinbefore defined, include thiazolyl, isothiazolyl, thiadiazolyl, pyridyl, pyrazinyl, pyridazinyl, pyrazolyl, imidazolyl, pyrimidinyl, oxazolyl, isoxazolyl, oxadiazolyl and triazolyl.

It will be understood that HET-2 can be a saturated, or partially or fully unsaturated ring.

Suitable examples of HET-2 include azetidinyl, furyl, thienyl, thiazolyl, isothiazolyl, thiadiazolyl, pyridyl, pyrazinyl, pyridazinyl, pyrazolyl, imidazolyl, pyrimidinyl, oxazolyl, isoxazolyl, oxadiazolyl, morpholino, morpholinyl, piperidinyl, piperazinyl, morpholinyl, thiomorpholinyl, pyrrolyl, pyrrolidinyl, pyrrolidonyl, 2,5-dioxopyrrolidinyl, 1,1-dioxotetrahydrothienyl, 2-oxoimidazolidinyl, 2,4-dioxoimidazolidinyl, 2-oxo-1,3,4-(4-triazolinyl), 2-oxazolidinonyl, 2-oxotetrahydrofuranyl, tetrahydrofuranyl, tetrahydropyranyl, 1,1-dioxothiomorpholino, 1,3-dioxolanyl, 1,2,4-triazolyl, 1,2,3-triazolyl, pyranyl, and 4-pyridonyl.

It will be understood that HET-2 may be linked by any appropriate available C or N atom, therefore for example, for HET-2 as "imidazolyl" includes 1-, 2-, 4-and 5-imidazolyl.

Suitable examples of Ring A as hereinbefore defined include thienyl, furyl, thiazolyl, isothiazolyl, thiadiazolyl, pyridyl, pyrazinyl, pyridazinyl, pyrazolyl, imidazolyl, pyrimidinyl, oxazolyl, isoxazolyl, oxadiazolyl and triazolyl. Further suitable examples of Ring A include aromatic heterocycles where a ring nitrogen or sulfur atom has been oxidised but aromaticity has been preserved, for example a pyridine N-oxide. Further suitable examples of Ring A include thiazolyl, pyridyl, pyrazinyl, pyridazinyl and pyrimidinyl.

It will be appreciated that the above suitable values for HET-1, HET-2 and Ring A may all be optionally substituted as defined hereinbefore.

It will be appreciated that, where definitions of heterocyclyl groups HET-1, HET-2 and Ring A encompass heteroaryl or heterocyclyl rings which may be substituted on nitrogen, such substitution may not result in charged quaternary nitrogen atoms or unstable structures (such as N-halo compounds). It will be appreciated that the definitions of HET-1, HET-2 and Ring A are not intended to include any O—O, O—S or S—S bonds. It will be appreciated that the definitions of HET-1, HET-2 and Ring A are not intended to include unstable structures.

Examples of (1-4C)alkyl include methyl, ethyl, propyl, isopropyl, butyl and tert-butyl; examples of (1-4C)alkoxy include methoxy, ethoxy, propoxy, isopropoxy and tertbutoxy; examples of (3-6C)cycloalkyl include cyclopropyl, cyclobutyl, cyclopentyl and cyclohexyl; examples of halo include fluoro, chloro, bromo and iodo; examples of hydroxy (1-4C)alkyl include hydroxymethyl, 1-hydroxyethyl, 2-hydroxyethyl, 2-hydroxypropyl, 3-hydroxypropyl, 1-hydroxyisopropyl and 4-hydroxybutyl; examples of (1-4C)alkoxy(1-4C)alkyl include methoxymethyl, ethoxymethyl, tert-butoxymethyl, 2-methoxyethyl, 2-ethoxyethyl, methoxypropyl, 2-methoxypropyl and methoxybutyl; examples of (1-4C)alkylS(O)$_p$(1-4C)alkyl include methylsulfinylmethyl, ethylsulfinylmethyl, ethylsulfinylethyl, methylsulfinylpropyl, methylsulfinylbutyl, methylsulfonylmethyl, ethylsulfonylmethyl, ethylsulfonylethyl, methylsulfonylpropyl, methylsulfonylbutyl, methylthiomethyl, ethylthiomethyl, ethylthioethyl, methylthiopropyl, and methylthiobutyl; examples of amino(1-4C)alkyl include aminomethyl, aminoethyl, 2-aminopropyl, 3-aminopropyl, 1-aminoisopropyl and 4-aminobutyl; examples of (1-4C) alkylamino(1-4C)alkyl include (N-methyl)aminomethyl, (N-ethyl)aminomethyl, 1-((N-methyl)amino)ethyl, 2-((N-methyl)amino)ethyl, (N-ethyl)aminoethyl, (N-methyl)aminopropyl, and 4-((N-methyl)amino)butyl; examples of di(1-4C)alkylamino(1-4C)alkyl include dimethylaminomethyl, methyl(ethyl)aminomethyl, methyl(ethyl)aminoethyl, (N,N-diethyl)aminoethyl, (N,N-dimethyl)aminopropyl and (N,N-dimethyl)aminobutyl; examples of (1-4C)alkylamino include methylamino, ethylamino, propylamino, isopropylamino, butylamino and tert-butylamino; examples of di(1-4C)alkylamino include dimethylamino, methyl(ethyl)amino, diethylamino, dipropylamino, di-isopropylamino and dibutylamino; examples of —C(O)(1-4C)alkyl include methylcarbonyl, ethylcarbonyl, propylcarbonyl and tert-butyl carbonyl; examples of (1-4C)alkylsulfonyl include methylsulfonyl, ethylsulfonyl, isopropylsulfonyl and tert-butylsulfonyl.

It is to be understood that, insofar as certain of the compounds of Formula (I) defined above may exist in optically active or racemic forms by virtue of one or more asymmetric carbon atoms, the invention includes in its definition any such optically active or racemic form which possesses the property of stimulating GLK directly or inhibiting the GLK/GLKRP interaction. The synthesis of optically active forms may be carried out by standard techniques of organic chemistry well known in the art, for example by synthesis from optically active starting materials or by resolution of a racemic form. It is also to be understood that certain compounds may exist in tautomeric forms and that the invention also relates to any and all tautomeric forms of the compounds of the invention which activate GLK.

It is also to be understood that certain compounds of the formula (I) and salts thereof can exist in solvated as well as unsolvated forms such as, for example, hydrated forms. It is to be understood that the invention encompasses all such solvated forms which activate GLK.

In one embodiment of the invention are provided compounds of formula (I), in an alternative embodiment are provided pharmaceutically-acceptable salts of compounds of formula (I), in a further alternative embodiment are provided in-vivo hydrolysable esters of compounds of formula (I), and in a further alternative embodiment are provided pharmaceutically-acceptable salts of in-vivo hydrolysable esters of compounds of formula (I).

Preferred values of each variable group are as follows. Such values may be used where appropriate with any of the values, definitions, claims, aspects or embodiments defined hereinbefore or hereinafter. In particular, each may be used as an individual limitation on the broadest definition of formula (I). Further, each of the following values may be used in combination with one or more of the other following values to limit the broadest definition of formula (I).

(1) $R^1$ is fluoromethoxymethyl or difluoromethoxymethyl
(2) $R^1$ is fluoromethoxymethyl and the configuration is preferably (S), that is the sidechain is:

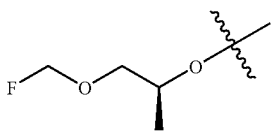

(3) $R^1$ is difluoromethoxymethyl and the configuration is preferably (S), that is the sidechain is:

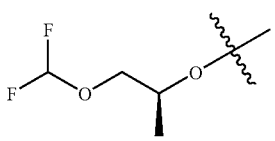

(4) $R^2$ is —C(O)NR$^4$R$^5$
(5) $R^2$ is —SO$_2$NR$^4$R$^5$
(6) $R^2$ is —S(O)$_p$R$^4$
(7) $R^2$ is HET-2
(8) $R^2$ is —C(O)NR$^4$R$^5$ or —SO$_2$NR$^4$R$^5$
(9) $R^2$ is in the para position relative to the ether linkage
(10) n is 0 or 1
(11) n is 0
(12) n is 1, $R^2$ is in the para position relative to the ether linkage, $R^3$ is in the ortho position relative to the ether linkage
(13) n is 1, $R^2$ is in the para position relative to the ether linkage, $R^3$ is in the meta position relative to the ether linkage
(14) n is 1
(15) n is 2
(16) n is 2 and both $R^3$ are halo
(17) n is 2 and each $R^3$ is independently fluoro or chloro
(18) n is 2, $R^2$ is in the para position relative to the ether linkage and each $R^3$ is in an ortho position relative to the ether linkage
(19) n is 2, both $R^3$ are halo, $R^2$ is in the para position relative to the ether linkage and each $R^3$ is in an ortho position relative to the ether linkage
(20) n is 2, both $R^3$ are halo, $R^2$ is in the para position relative to the ether linkage and one $R^3$ is in an ortho position relative to the ether linkage and the other $R^3$ is in a meta position relative to the ether linkage
(21) $R^3$ is chloro or fluoro
(22) $R^3$ is fluoro
(23) $R^3$ is chloro
(24) n is 2 and both $R^3$ are fluoro
(25) n is 2 and one $R^3$ is fluoro and the other is chloro
(26) p is 0
(27) p is 1
(28) p is 2
(29) HET-1 is a 5-membered heteroaryl ring
(30) HET-1 is a 6-membered heteroaryl ring
(31) HET-1 is substituted with 1 or 2 substituents independently selected from $R^6$
(32) HET-1 is substituted with 1 substituent selected from $R^6$
(33) HET-1 is unsubstituted
(34) HET-1 is selected from thiazolyl, isothiazolyl, thiadiazolyl, pyridyl, pyrazinyl, pyridazinyl, pyrazolyl, imidazolyl, pyrimidinyl, oxazolyl, isoxazolyl, oxadiazolyl, and triazolyl
(35) HET-1 is selected from thiazolyl, isothiazolyl, thiadiazolyl, pyrazolyl, imidazolyl, oxazolyl, isoxazolyl and oxadiazolyl
(36) HET-1 is selected from pyridyl, pyrazinyl, pyridazinyl and pyrimidinyl
(37) HET-1 is optionally substituted pyrazolyl, for example pyrazolyl or N-methylpyrazolyl
(38) HET-1 is pyridyl or pyrazinyl
(39) HET-1 is pyrazinyl
(40) HET-1 is selected from pyrazolyl, N-methylpyrazolyl and methylpyrazinyl (such as 5-methylpyrazin-2-yl)
(41) HET-1 is pyrazolyl (optionally substituted with ethyl, isopropyl or 1 or 2 methyl), thiazolyl (optionally substituted with methyl), pyrazinyl (optionally substituted with methyl), pyridyl (optionally substituted by fluoro), isoxazolyl (optionally substituted with methyl) and thiadiazolyl (optionally substituted with methyl)
(42) HET-1 is pyrazolyl (optionally substituted with ethyl, isopropyl, difluoromethyl, or 1 or 2 methyl), thiazolyl (optionally substituted with methyl), pyrazinyl (optionally substituted with methyl), pyridyl (optionally substituted by fluoro), isoxazolyl (optionally substituted with methyl) and thiadiazolyl (optionally substituted with methyl)
(43) HET-1 is selected from pyrazinyl (optionally substituted with methyl), pyrazolyl (optionally substituted on carbon by methyl), methylthiadiazolyl (particularly 1,2,4-thiadiazol-5-yl, more particularly 3-methyl-1,2,4-thiadiazol-5-yl), thiazolyl (optionally substituted with methyl), pyridyl (optionally substituted by fluoro) and isoxazolyl
(44) $R^6$ is selected from (1-4C)alkyl, halo, hydroxy(1-4C)alkyl, di(1-4C)alkylamino(1-4C)alkyl
(45) $R^6$ is selected from methyl, ethyl, chloro, fluoro, hydroxymethyl, methoxymethyl, aminomethyl, N-methylaminomethyl, dimethylaminomethyl
(46) $R^6$ is selected from methyl, ethyl, chloro, fluoro, hydroxymethyl and methoxymethyl
(47) $R^6$ is selected from methyl or ethyl
(48) $R^6$ is methyl

(49) $R^6$ is selected from (1-4C)alkyl and (1-4C)alkoxy(1-4C)alkyl
(50) $R^6$ is selected from methyl, ethyl, isopropyl and methoxymethyl
(51) when 2 substituents $R^6$ are present, both are selected from methyl, ethyl, bromo, chloro and fluoro; preferably both are methyl and at least one is on an available nitrogen atom
(52) $R^4$ is hydrogen
(53) $R^4$ is (1-4C)alkyl [substituted by 1 or 2 substituents independently selected from HET-2, —$OR^5$, —$SO_2R^5$, (3-6C)cycloalkyl (optionally substituted with 1 group selected from $R^7$) and —$C(O)NR^5R^5$]
(54) $R^4$ is (1-4C)alkyl [substituted by 1 substituent selected from HET-2, —$OR^5$, —$SO_2R^5$, (3-6C)cycloalkyl and —$C(O)NR^5R^5$]
(55) $R^4$ is (1-4C)alkyl
(56) $R^4$ is (1-4C)alkyl substituted by —$OR^5$
(57) $R^4$ is (1-4C)alkyl substituted by HET-2
(58) $R^4$ is (3-6C)cycloalkyl, particularly cyclopropyl or cyclobutyl
(59) $R^4$ is (3-6C)cycloalkyl substituted by a group selected from $R^7$
(60) $R^4$ is (3-6C)cycloalkyl substituted by a group selected from —$OR^5$ and (1-4C)alkyl
(61) $R^4$ is selected from (1-4C)alkyl and (3-6C)cycloalkyl
(62) $R^4$ is selected from methyl, ethyl, cyclopropyl and cyclobutyl
(63) $R^4$ is HET-2
(64) $R^4$ is selected from hydrogen, (1-4C)alkyl, and (1-4C)alkyl substituted with —$OR^5$
(65) HET-2 is unsubstituted
(66) HET-2 is substituted with 1 or 2 substituents independently selected from (1-4C)alkyl, hydroxy and (1-4C)alkoxy
(67) HET-2 is a fully saturated ring system
(68) HET-2 is a fully unsaturated ring system
(69) HET-2 is selected from azetidinyl, morpholino, morpholinyl, piperidinyl, piperazinyl, 3-oxopiperazinyl, thiomorpholinyl, pyrrolidinyl, pyrrolidonyl, 2,5-dioxopyrrolidinyl, 1,1-dioxotetrahydrothienyl, 2-oxazolidinonyl, 2-oxotetrahydrofuranyl, tetrahydrofuranyl, tetrahydropyranyl, 1,1-dioxothiomorpholino, 1,3-dioxolanyl, 2-oxoimidazolidinyl, 2,4-dioxoimidazolidinyl, pyranyl and 4-pyridonyl
(70) HET-2 is selected from azetidinyl, morpholino, morpholinyl, piperidinyl, piperazinyl, pyrrolidinyl, thiomorpholinyl, tetrahydrofuranyl, and tetrahydropyranyl
(71) HET-2 is selected from furyl, thienyl, thiazolyl, isothiazolyl, thiadiazolyl, pyridyl, pyrazinyl, pyridazinyl, pyrazolyl, imidazolyl, pyrimidinyl, oxazolyl, isoxazolyl, oxadiazolyl, pyrrolyl, 1,2,4-triazolyl and 1,2,3-triazolyl
(72) HET-2 is selected from furyl, thienyl, thiazolyl, isothiazolyl, thiadiazolyl, pyridyl, imidazolyl, pyrimidinyl, oxazolyl, isoxazolyl, oxadiazolyl, piperidinyl, piperazinyl, 3-oxopiperazinyl, pyrrolidinyl, pyrrolidonyl, 2-oxazolidinonyl, tetrahydrofuranyl, tetrahydropyranyl, 1,1-dioxotetrahydrothienyl, and 2-oxoimidazolidinyl
(73) HET-2 is selected from morpholino, furyl, imidazolyl, oxazolyl, isoxazolyl, oxadiazolyl, piperidinyl, piperazinyl, 3-oxopiperazinyl, pyrrolidinyl, 2-pyrrolidonyl, 2-oxazolidinonyl, tetrahydrofuranyl, tetrahydropyranyl, 1,1-dioxotetrahydrothienyl, and 2-oxoimidazolidinyl
(74) HET-2 is selected from morpholino, furyl, imidazolyl, isoxazolyl, oxadiazolyl, piperidinyl, piperazinyl, 3-oxopiperazinyl, pyrrolidinyl, 2-pyrrolidonyl, tetrahydropyranyl, 1,1-dioxotetrahydrothienyl, and 2-oxoimidazolidinyl
(75) HET-2 is oxadiazolyl or pyrazolyl
(76) $R^5$ is hydrogen
(77) $R^5$ is (1-4)alkyl, preferably methyl
(78) $R^5$ is hydrogen or methyl
(79) $R^7$ is a substituent on carbon and is selected from hydroxy, (1-4C)alkoxy, (1-4C)alkyl, —C(O)(1-4C)alkyl, —$C(O)NR^4R^5$, (1-4C)alkoxy(1-4C)alkyl, and hydroxy(1-4C)alkyl
(80) $R^7$ is a substituent on carbon and is selected from hydroxy, (1-4C)alkoxy, (1-4C)alkyl, —C(O)(1-4C)alkyl, —$C(O)NR^4R^5$, and hydroxy(1-4C)alkyl
(81) $R^7$ is a substituent on carbon and is selected from hydroxy, methoxy, —COMe, —$CONH_2$, —CONHMe, —$CONMe_2$, and hydroxymethyl
(82) $R^7$ is a substituent on carbon and is selected from (1-4C)alkyl, hydroxy and (1-4C)alkoxy
(83) $R^7$ is a substituent on carbon and is selected from methyl, ethyl, methoxy and hydroxy
(84) $R^7$ is a substituent on nitrogen and is selected from (1-4C)alkyl, —C(O)(1-4C)alkyl, —$C(O)NR^4R^5$, (1-4C)alkoxy(1-4C)alkyl, and hydroxy(1-4C)alkyl
(85) $R^7$ is a substituent on nitrogen and is selected from (1-4C)alkyl, hydroxy and (1-4C)alkoxy
(86) $R^7$ is methyl
(87) $R^8$ is selected from methyl, hydroxy, methoxy, —$CONH_2$, —CONHMe, —$CONMe_2$, hydroxymethyl, hydroxyethyl, —NHMe and —$NMe_2$ (88) $R^8$ is selected from methyl, —$CONH_2$, hydroxyethyl and hydroxy
(89) $R^8$ is selected from (1-4C)alkyl and (1-4C)alkoxy
(90) $R^8$ is selected from methyl, methoxy and isopropoxy
(91) $R^8$ is methyl
(92) $R^9$ is selected from methyl, hydroxy, methoxy, —$CONH_2$, —CONHMe, —$CONMe_2$, hydroxymethyl, hydroxyethyl, —NHMe and —$NMe_2$ (93) $R^9$ is methyl
(94) HET-2 is a 5-membered ring
(95) HET-2 is a 6-membered ring
(96) HET-2 is selected from thienyl, furyl, thiazolyl, isothiazolyl, thiadiazolyl, pyridyl, pyrazinyl, pyridazinyl, pyrazolyl, imidazolyl, pyrimidinyl, oxazolyl, isoxazolyl and oxadiazolyl
(97) HET-2 is selected from thienyl, furyl, thiadiazolyl, pyridyl, pyrazinyl, pyridazinyl, pyrazolyl, imidazolyl, pyrimidinyl and oxadiazolyl
(98) HET-2 is selected from pyridyl, pyrazinyl, thiazolyl and thienyl
(99) HET-2 is selected from pyridyl, pyrazinyl and thiazolyl
(101) HET-2 is selected from pyridyl, pyrazinyl, pyridazinyl and thiazolyl
(102) HET-2 is selected from pyridyl and pyrazinyl
(103) HET-2 is pyrazinyl
(104) HET-2 is not substituted on nitrogen
(105) HET-2 has one nitrogen substituent selected from $R^8$
(106) $R^8$ is (1-4C)alkyl
(107) $R^8$ is (3-6C)cycloalkyl
(108) $R^8$ is hydroxy(1-4C)alkyl or (1-4C)alkoxy(1-4C)alkyl
(109) $R^8$ is —C(O)(1-4C)alkyl
(110) $R^8$ is benzyl
(111) $R^8$ is (1-4C)alkylsulfonyl
(112) $R^8$ is (1-4C)alkyl or benzyl According to a further feature of the invention there is provided the following preferred groups of compounds of the invention:

In one aspect of the invention there is provided a compound of formula (I), or a salt thereof, wherein $R^1$ is selected from fluoromethoxymethyl and difluoromethoxymethyl (particularly difluoromethoxymethyl);

$R^2$ is selected from —C(O)NR$^4$R$^5$, —SO$_2$NR$^4$R$^5$ and —SO$_p$R$^4$;

Ring A is pyridyl or pyrazinyl;

$R^3$ is selected from fluoro and chloro;

n is 0 or 1;

HET-1 is selected from pyrazolyl (optionally substituted with ethyl, isopropyl, difluoromethyl, or 1 or 2 methyl), thiazolyl (optionally substituted with methyl), pyrazinyl (optionally substituted with methyl), pyridyl (optionally substituted by fluoro), isoxazolyl (optionally substituted with methyl) and thiadiazolyl (optionally substituted with methyl);

$R^4$ is hydrogen or (1-4C)alkyl;

$R^5$ is hydrogen or (1-4C)alkyl;

p is 0, 1 or 2, particularly 2.

In another aspect of the invention there is provided a compound of formula (I), or a salt thereof, wherein $R^1$ is selected from fluoromethoxymethyl and difluoromethoxymethyl (particularly difluoromethoxymethyl);

$R^2$ is selected from —C(O)NR$^4$R$^5$ and —SO$_p$R$^4$;

Ring A is pyridyl or pyrazinyl;

$R^3$ is selected from fluoro and chloro;

n is 0 or 1;

HET-1 is selected from pyrazolyl (optionally substituted with methyl) and pyrazinyl (optionally substituted with methyl);

$R^4$ is (1-4C)alkyl;

$R^5$ is hydrogen or (1-4C)alkyl;

p is 0, 1 or 2, particularly 2.

In another aspect of the invention there is provided a compound of formula (I), or a salt thereof, wherein $R^1$ is selected from fluoromethoxymethyl and difluoromethoxymethyl (particularly difluoromethoxymethyl);

$R^2$ is selected from —C(O)NR$^4$R$^5$ and —SO$_p$R$^4$;

Ring A is pyridyl or pyrazinyl;

$R^3$ is selected from fluoro and chloro;

n is 0 or 1;

HET-1 is selected from pyrazolyl (optionally substituted with methyl) and pyrazinyl (optionally substituted with methyl);

$R^4$ is methyl;

$R^5$ is hydrogen or methyl;

p is 0, 1 or 2, particularly 2.

Further preferred compounds of the invention are each of the Examples, each of which provides a further independent aspect of the invention. In further aspects, the present invention also comprises any two or more compounds of the Examples.

Particular compounds of the invention include any one or more of:

3-[(2S)-1-(difluoromethoxy)propan-2-yl]oxy-N-(5-methylpyrazin-2-yl)-5-(6-methylsulfonylpyridin-3-yl)oxybenzamide;

5-[3-[(2S)-1-(difluoromethoxy)propan-2-yl]oxy-5-[(5-methylpyrazin-2-yl)carbamoyl]phenoxy]-N,N-dimethylpyrazine-2-carboxamide;

5-[3-[(2S)-1-(difluoromethoxy)propan-2-yl]oxy-5-(1H-pyrazol-3-ylcarbamoyl)phenoxy]-N,N-dimethyl-pyrazine-2-carboxamide;

3-[(2S)-1-(difluoromethoxy)propan-2-yl]oxy-5-(6-methylsulfonylpyridin-3-yl)oxy-N-(1H-pyrazol-3-yl)benzamide;

5-[3-[(2S)-1-(difluoromethoxy)propan-2-yl]oxy-5-[(1-methylpyrazol-3-yl)carbamoyl]phenoxy]-N,N-dimethylpyrazine-2-carboxamide;

3-[(2S)-1-(difluoromethoxy)propan-2-yl]oxy-N-(1-methylpyrazol-3-yl)-5-(6-methylsulfonylpyridin-3-yl)oxybenzamide;

or a salt thereof.

The compounds of the invention may be administered in the form of a pro-drug. A pro-drug is a bioprecursor or pharmaceutically acceptable compound being degradable in the body to produce a compound of the invention (such as an ester or amide of a compound of the invention, particularly an in-vivo hydrolysable ester). Various forms of prodrugs are known in the art. For examples of such prodrug derivatives, see:

a) Design of Prodrugs, edited by H. Bundgaard, (Elsevier, 1985) and Methods in Enzymology, Vol. 42, p. 309-396, edited by K. Widder, et al. (Academic Press, 1985);

b) A Textbook of Drug Design and Development, edited by Krogsgaard-Larsen;

c) H. Bundgaard, Chapter 5 "Design and Application of Prodrugs", by H. Bundgaard p. 113-191 (1991);

d) H. Bundgaard, Advanced Drug Delivery Reviews, 8, 1-38 (1992);

e) H. Bundgaard, et al., Journal of Pharmaceutical Sciences, 77, 285 (1988); and f) N. Kakeya, et al., Chem Pharm Bull, 32, 692 (1984).

The contents of the above cited documents are incorporated herein by reference.

Examples of pro-drugs are as follows. An in-vivo hydrolysable ester of a compound of the invention containing a carboxy or a hydroxy group is, for example, a pharmaceutically-acceptable ester which is hydrolysed in the human or animal body to produce the parent acid or alcohol. Suitable pharmaceutically-acceptable esters for carboxy include $C_1$ to $C_6$alkoxymethyl esters for example methoxymethyl, $C_1$ to $C_{16}$alkanoyloxymethyl esters for example pivaloyloxymethyl, phthalidyl esters, $C_3$ to $C_8$cycloalkoxycarbonyloxy$C_1$ to $C_6$alkyl esters for example 1-cyclohexylcarbonyloxyethyl; 1,3-dioxolen-2-onylmethyl esters, for example 5-methyl-1,3-dioxolen-2-onylmethyl; and $C_{1-16}$alkoxycarbonyloxyethyl esters.

An in-vivo hydrolysable ester of a compound of the invention containing a hydroxy group includes inorganic esters such as phosphate esters (including phosphoramidic cyclic esters) and α-acyloxyalkyl ethers and related compounds which as a result of the in-vivo hydrolysis of the ester breakdown to give the parent hydroxy group/s. Examples of α-acyloxyalkyl ethers include acetoxymethoxy and 2,2-dimethylpropionyloxy-methoxy. A selection of in-vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

Under certain conditions, compounds of Formula (I) may form pharmaceutically acceptable salts. A suitable pharmaceutically-acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. It will be understood that an acid addition salt may be formed with any sufficiently basic group which may for example be in HET-1 or may for example be a substituent $R^2$. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

A further feature of the invention is a pharmaceutical composition comprising a compound of Formula (I) as defined above, or a pharmaceutically-acceptable salt thereof, together with a pharmaceutically-acceptable diluent or carrier.

According to another aspect of the invention there is provided a compound of Formula (I) as defined above or a pharmaceutically-acceptable salt thereof for use as a medicament.

According to another aspect of the invention there is provided a compound of Formula (I), or a pharmaceutically-acceptable salt thereof as defined above for use as a medicament for treatment of a disease mediated through GLK, in particular type 2 diabetes.

Further according to the invention there is provided the use of a compound of Formula (I) or a pharmaceutically-acceptable salt thereof in the preparation of a medicament for treatment of a disease mediated through GLK, in particular type 2 diabetes.

The compound is suitably formulated as a pharmaceutical composition for use in this way.

According to another aspect of the present invention there is provided a method of treating GLK mediated diseases, especially diabetes, by administering an effective amount of a compound of Formula (I) or a pharmaceutically-acceptable salt thereof, to a mammal in need of such treatment.

According to another aspect of the present invention there is provided the use of a compound of Formula (I), or a pharmaceutically-acceptable salt thereof, for treatment of a disease mediated through GLK.

According to another aspect of the present invention there is provided the use of a compound of Formula (I), or a pharmaceutically-acceptable salt thereof, for treatment of type 2 diabetes.

Specific diseases which may be treated by a compound or composition of the invention include: blood glucose lowering in Type 2 Diabetes Mellitus without a serious risk of hypoglycaemia (and potential to treat 1), dyslipidemia, obesity, insulin resistance, metabolic syndrome X, impaired glucose tolerance.

As discussed above, thus the GLK/GLKRP system can be described as a potential "Diabesity" target (of benefit in both Diabetes and Obesity). Thus, according to another aspect of the invention there is provided the use of a compound of Formula (I) or a pharmaceutically-acceptable salt thereof, in the preparation of a medicament for use in the combined treatment or prevention, particularly treatment, of diabetes and obesity.

According to another aspect of the invention there is provided the use of a compound of Formula (I) or a pharmaceutically-acceptable salt thereof, in the preparation of a medicament for use in the treatment or prevention of obesity.

According to a further aspect of the invention there is provided a method for the combined treatment of obesity and diabetes by administering an effective amount of a compound of Formula (I) or a pharmaceutically-acceptable salt thereof, to a mammal in need of such treatment.

According to another aspect of the invention there is provided a compound of Formula (I) or a pharmaceutically-acceptable salt thereof as defined above for use as a medicament for treatment or prevention, particularly treatment of obesity.

According to a further aspect of the invention there is provided a method for the treatment of obesity by administering an effective amount of a compound of Formula (I) or a pharmaceutically-acceptable salt thereof, to a mammal in need of such treatment.

Compounds of the invention may be particularly suitable for use as pharmaceuticals, for example because of favourable physical and/or pharmacokinetic properties and/or toxicity profile.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing). Dosage forms suitable for oral use are preferred.

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the dose for therapeutic or prophylactic purposes of a compound of the Formula (I) will naturally vary according to the nature and severity of the conditions, the age and sex of the animal or patient and the route of administration, according to well known principles of medicine.

In using a compound of the Formula (I) for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used. Oral administration is however preferred.

The elevation of GLK activity described herein may be applied as a sole therapy or in combination with one or more other substances and/or treatments for the indication being treated. Such conjoint treatment may be achieved by way of the simultaneous, sequential or separate administration of the individual components of the treatment. Simultaneous treatment may be in a single tablet or in separate tablets. For example in the treatment of diabetes mellitus, chemotherapy may include the following main categories of treatment:

1) Insulin and insulin analogues;
2) Insulin secretagogues including sulphonylureas (for example glibenclamide, glipizide), prandial glucose regulators (for example repaglinide, nateglinide);
3) Agents that improve incretin action (for example dipeptidyl peptidase IV inhibitors, and GLP-1 agonists);
4) Insulin sensitising agents including PPARgamma agonists (for example pioglitazone and rosiglitazone), and agents with combined PPARalpha and gamma activity;
5) Agents that modulate hepatic glucose balance (for example metformin, fructose 1, 6 bisphosphatase inhibitors, glycogen phopsphorylase inhibitors, glycogen synthase kinase inhibitors);
6) Agents designed to reduce the absorption of glucose from the intestine (for example acarbose);
7) Agents that prevent the reabsorption of glucose by the kidney (SGLT inhibitors);
8) Agents designed to treat the complications of prolonged hyperglycaemia (for example aldose reductase inhibitors);
9) Anti-obesity agents (for example sibutramine and orlistat);
10) Anti-dyslipidaemia agents such as, HMG-CoA reductase inhibitors (eg statins); PPARα agonists (fibrates, eg gemfibrozil); bile acid sequestrants (cholestyramine); cholesterol absorption inhibitors (plant stanols, synthetic inhibitors); bile acid absorption inhibitors (IBATi) and nicotinic acid and analogues (niacin and slow release formulations);
11) Antihypertensive agents such as, β blockers (eg atenolol, inderal); ACE inhibitors (eg lisinopril); Calcium antagonists (eg. nifedipine); Angiotensin receptor antagonists (eg candesartan), α antagonists and diuretic agents (eg. furosemide, benzthiazide);
12) Haemostasis modulators such as, antithrombotics, activators of fibrinolysis and antiplatelet agents; thrombin antagonists; factor Xa inhibitors; factor VIIa inhibitors); antiplatelet agents (eg. aspirin, clopidogrel); anticoagulants (heparin and Low molecular weight analogues, hirudin) and warfarin;
13) Agents which antagonise the actions of glucagon; and
14) Anti-inflammatory agents, such as non-steroidal anti-inflammatory drugs (eg. aspirin) and steroidal anti-inflammatory agents (eg. cortisone).

According to another aspect of the present invention there is provided individual compounds produced as end products in the Examples set out below and salts thereof.

A compound of the invention, or a salt thereof, may be prepared by any process known to be applicable to the preparation of such compounds or structurally related compounds. Functional groups may be protected and deprotected using conventional methods. For examples of protecting groups such as amino and carboxylic acid protecting groups (as well as means of formation and eventual deprotection), see T. W. Greene and P. G. M. Wuts, "Protective Groups in Organic Synthesis", Second Edition, John Wiley & Sons, New York, 1991.

Processes for the synthesis of compounds of Formula (I) are provided as a further feature of the invention. Thus, according to a further aspect of the invention there is provided a process for the preparation of a compound of Formula (I), which comprises a process a) to e) (wherein the variables are as defined hereinbefore for compounds of Formula (I) unless otherwise defined):

(a) reaction of an acid of Formula (III) or activated derivative thereof with a compound of Formula (IV), wherein $R^1$ is as defined for formula (I) or is a precursor thereof;

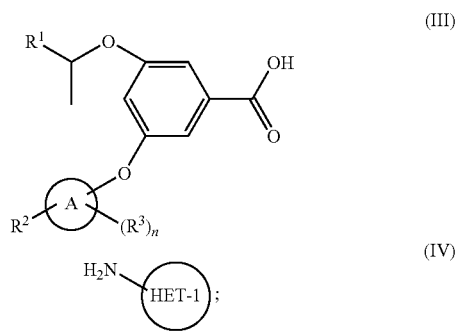

or (b) reaction of a compound of Formula (V) with a compound of Formula (VI),

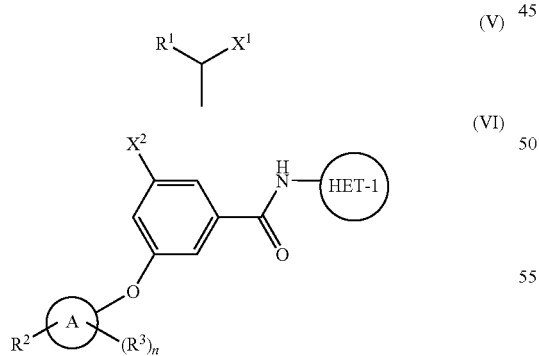

wherein $X^1$ is a leaving group and $X^2$ is a hydroxyl group or $X^1$ is a hydroxyl group and $X^2$ is a leaving group, and wherein $R^1$ is as defined for formula (I) or is a precursor thereof;

process (b) could also be accomplished using the intermediate ester Formula (VII), wherein $P^1$ is a protecting group as hereinafter described, followed by ester hydrolysis and amide formation by procedures described elsewhere and well known to those skilled in the art;

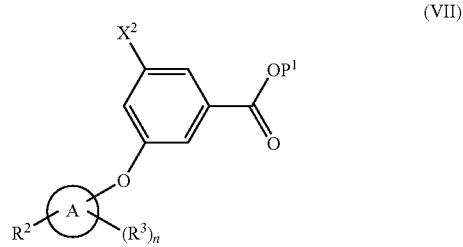

or (c) reaction of a compound of Formula (VIII) with a compound of Formula (IX)

wherein $X^3$ is a leaving group or an organometallic reagent and $X^4$ is a hydroxyl group or $X^3$ is a hydroxyl group and $X^4$ is a leaving group or an organometallic reagent, and wherein $R^1$ is as defined for formula (I) or is a precursor thereof;

process (c) could also be accomplished using the intermediate ester Formula (X), followed by ester hydrolysis and amide formation by procedures described elsewhere and well known to those skilled in the art;

or (d) reaction of a compound of Formula (XI) with a compound of Formula (XII),

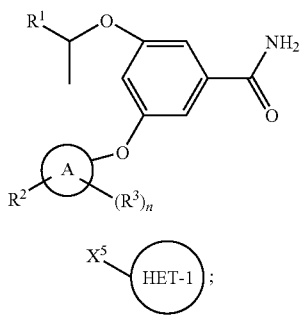

(XI)

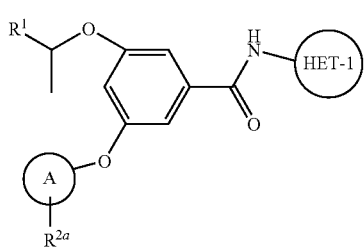

(XII)

wherein $X^5$ is a leaving group; and wherein $R^1$ is as defined for formula (I) or is a precursor thereof; or e) reaction of a compound of formula (XIII)

(XIII)

wherein $R^{2a}$ is a precursor to $R^2$ as —$CONR^4R^5$ or —$SO_2R^4R^5$, such as a carboxylic acid, ester or anhydride (for $R^2$=—$CONR^4R^5$) or the sulfonic acid equivalents (for $R^2$ is —$SO^2NR^4R^5$); with an amine of formula —$NR^4R^5$; and thereafter, if necessary:

i) converting a compound of Formula (I) into another compound of Formula (I);
ii) converting a precursor of $R^1$ into $R^1$;
iii) removing any protecting groups; and/or
iv) forming a salt thereof.

Suitable leaving groups $X^1$ to $X^5$ for processes b) to d) are any leaving group known in the art for these types of reactions, for example halo, alkoxy, trifluoromethanesulfonyloxy, methanesulfonyloxy, or p-toluenesulfonyloxy; or a group (such as a hydroxy group) that may be converted into a leaving group (such as an oxytriphenylphosphonium group) in situ.

Suitable precursors to $R^1$ include a hydroxy group or a protected hydroxy group, such as any suitable protected hydroxy group known in the art, for example simple ethers such as a methyl ether, or silylethers such as —$OSi[(1-4C)alkyl]_3$ (wherein each (1-4C)alkyl group is independently selected from methyl, ethyl, propyl, isopropyl, and tertbutyl). Examples of such trialkylsilyl groups are trimethylsilyl, triethylsilyl, triisopropylsilyl and tert-butyldimethylsilyl. Further suitable silyl ethers are those containing phenyl and substituted phenyl groups, such as —$Si(PhMe_2)$ and —$Si(TolMe_2)$ (wherein Tol=methylbenzene). Further suitable values for hydroxy protecting groups are given hereinafter. $R^1$ itself may then be generated by removing the hydroxy protecting group if present, and then by reacting with, for example 2-(fluorosulphonyl)difluoroacetic acid in the presence of copper (I) iodide to give the compound wherein $R^1$ is difluoromethoxymethyl. This reaction is illustrated in Scheme 1. Other values of $R^1$ may be generated similarly or by methods well known in the art, see for example Bull. Chem. Soc. Japan, 73 (2000), 471-484, 471-484, International Patent application WO 2002/050003 and Bioorganic and Medicinal Chemistry Letters, (2001), 11, 407.

Compounds of Formulae (III) to (XII) are commercially available, or are known in the art, or may be made by processes known in the art, for example as shown in the accompanying Examples. For further information on processes for making such compounds, we refer to our PCT publications WO 03/000267, WO 03/015774, WO 03/000262, WO 2004/076420, WO 2005/054200, WO 2005/054233, WO 2005/044801 and WO 2005/056530 and references therein. In general it will be appreciated that any aryl-O or alkyl-O bond may be formed by nucleophilic substitution or metal catalysed processes, optionally in the presence of a suitable base.

Compounds of Formula (XIII) may be made by processes such as those shown in processes a) to d) and/or by those processes mentioned above for compounds of formulae (III) to (XII).

Compounds of formulae (III), (IX), (X), (XI) and (XIII) may be made by reaction of suitable precursors with compounds of formula (V) or derivatives thereof, depending on the nature of the $R^1$ group or its precursor, for example, by nucleophilic displacement of a leaving group $X^1$ in a compound of formula (V). Compounds of formula (V) are generally commercially available or may be made by simple functional group interconversions from commercially available compounds, or by literature methods. Where the compound of formula (V) contains a precursor to $R^1$, the $R^1$ group may be generated in the compound of formula (III), (IX), (X), (XI) or (XIII) as appropriate using reactions such as those illustrated in Schemes 1 and 2 below. Illustrative examples are shown in Schemes 1 and 2 below, and/or in the accompanying examples.

Scheme 1

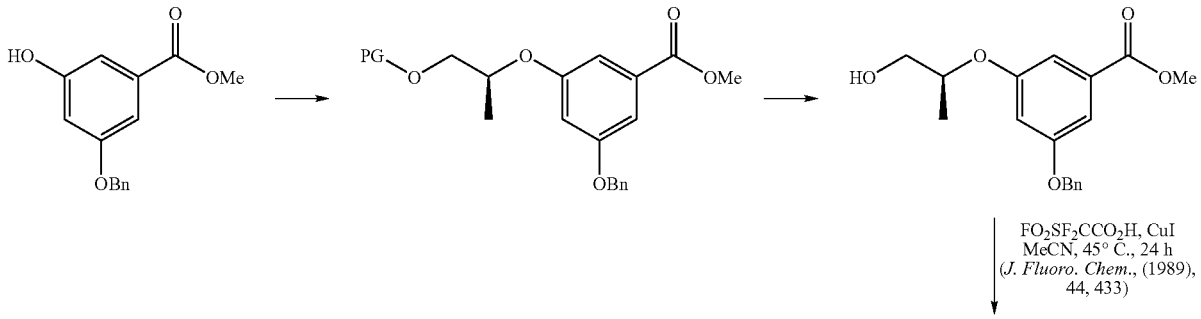

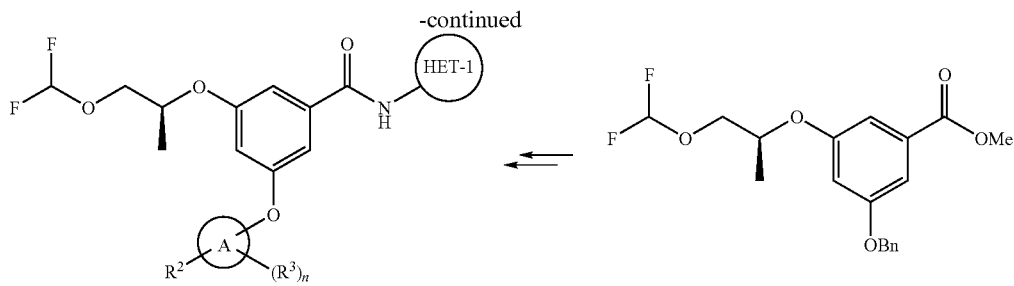

wherein:
PG is protecting group and $R^2$, $R^3$, A, n and HET-1 are as defined for Formula (I).

Scheme 2

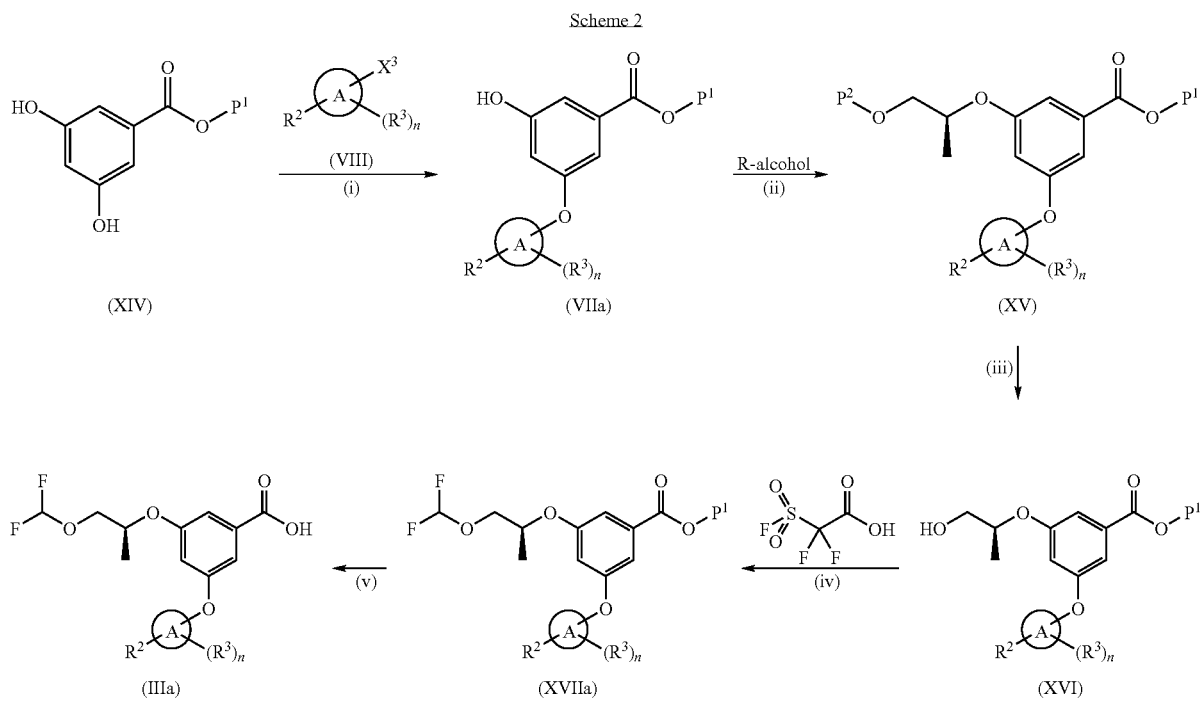

wherein:
$R^2$, $R^3$, A and n are as defined for Formula (I), $P^1$ and $P^2$ are suitable protecting groups, for example (1-4C)alkyl, and $X^3$ is a leaving group, for example chloro. Suitable reaction conditions for steps (i) to (v) of Scheme 2 are as follows:

Step (i) involves the reaction of Formula (XIV) with a compound of Formula (VIII), for example 5-chloro-N,N-dimethyl-pyrazine-2-carboxamide, in the presence of a suitable base, for example cesium carbonate, in a suitable solvent, for example DMSO, and at a suitable temperature, for example 0 to 60° C., more suitably about 50° C.

Step (ii) involves the reaction of a compound of Formula (VII) with an R-alcohol, for example (2R)-1-[(2-methylpropan-2-yl)oxy]propan-2-ol, in the presence of a suitable phosphine, for example triphenylphosphine, and an azodicarboxylate, for example diethylazodicarboxylate, in a suitable solvent, for example THF, and at a suitable temperature, for example 0 to 10° C., more suitably about 0° C.

Step (iii) involves heating a solution of Formula (XV) in a suitable acid, for example formic acid, at a suitable temperature, for example 0 to 50 to 100° C., more suitably about 90° C.

Step (iv) involves the reaction of a compound of Formula (XVI) with 2,2-difluoro-2-fluorosulfonyl-acetic acid, in the presence of a suitable catalyst, for example copper (I) iodide, in a suitable solvent, for example acetonitrile, and at a suitable temperature, for example 0 to 100° C., more suitably about 55° C.

Step (v) involves the reaction of a compound of Formula (XVIIa) with a suitable base, for example NaOH, in a suitable solvent, for example NMP and water, and at a suitable temperature, for example 0 to 25° C., more suitably about 0° C.

Alternatively, compounds of Formula (IIIa) where $R^1$ represents difluoromethoxymethyl may be made according to Scheme 3 as shown below.

Scheme 3

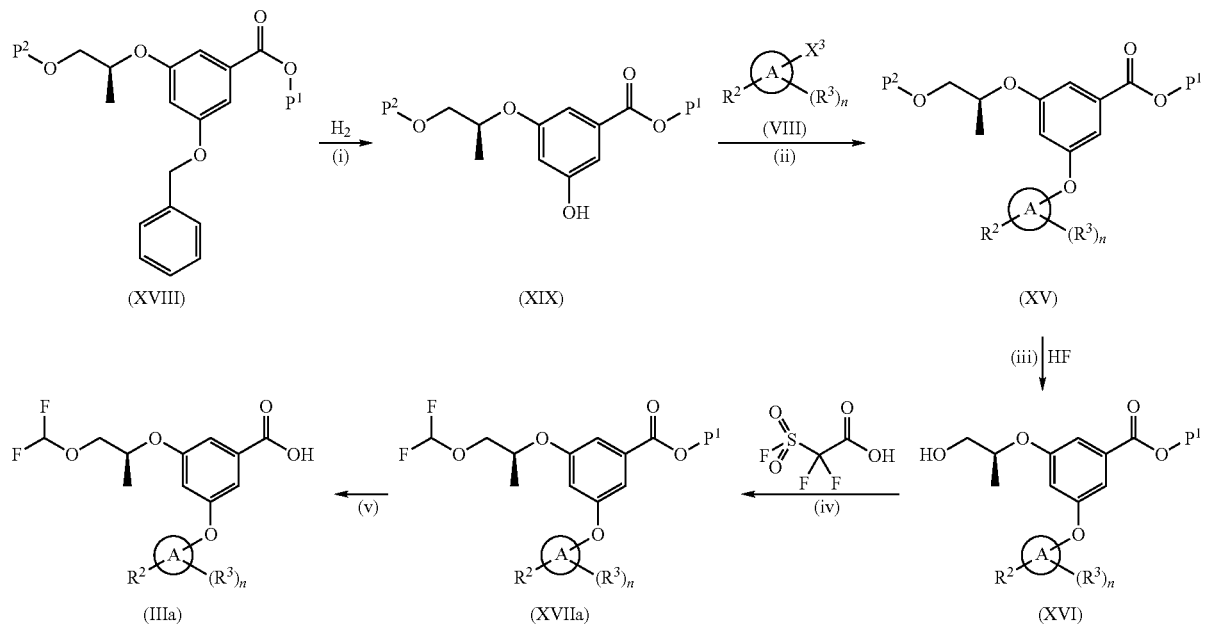

wherein:
R², R³, A and n are as defined for Formula (I), P¹ and P² are suitable protecting groups, for example (1-4C)alkyl and TIPS respectively, and X³ is a leaving group, for example chloro. Suitable reaction conditions for steps (i) to (v) of Scheme 2 are as follows:

Step (i) involves the reaction of a compound of Formula (XVIII) with hydrogen in the presence of a suitable catalyst, for example 10% palladium on activated carbon, and at a suitable temperature, for example 0 to 25° C., more suitably about 21° C.

Step (ii) involves the reaction of a compound of Formula (XIX) with a compound of Formula (VIII), for example 5-chloro-N,N-dimethyl-pyrazine-2-carboxamide, in the presence of a suitable base, for example potassium carbonate, in a suitable solvent, for example acetonitrile, and at a suitable temperature, for example 0 to 200° C., more suitably about reflux temperature.

Step (iii) involves the reaction of a compound of Formula (XV) with hydrogen fluoride in a suitable solvent, for example THF, and at a suitable temperature, for example 0 to 25° C., more suitably about 21° C.

Step (iv) involves the reaction of a compound of Formula (XVI) with 2,2-difluoro-2-fluorosulfonyl-acetic acid, in the presence of a suitable catalyst, for example copper (I) iodide, in a suitable solvent, for example acetonitrile, and at a suitable temperature, for example 0 to 100° C., more suitably about 55° C.

Step (v) involves the reaction of a compound of Formula (XVIIa) with a suitable base, for example LiOH, in a suitable solvent, for example THF and methanol, and at a suitable temperature, for example 0 to 25° C., more suitably about 21° C.

Examples of conversions of a compound of Formula (I) into another compound of Formula (I) well known to those skilled in the art, include functional group interconversions such as hydrolysis, hydrogenation, hydrogenolysis, oxidation or reduction, and/or further functionalisation by standard reactions such as amide or metal-catalysed coupling, or nucleophilic displacement reactions. An example would be removal of an R³=chloro substituent, for example by reaction with hydrogen at atmospheric or elevated pressure, in a suitable solvent such as THF/methanol or ethanol.

It will be understood that substituents R², R³ and/or R⁶ may be introduced into the molecule at any convenient point in the synthetic sequence or may be present in the starting materials. A precursor to one of these substituents may be present in the molecule during the process steps a) to e) above, and then be transformed into the desired substituent as a final step to form the compound of formula (I); followed where necessary by
i) converting a compound of Formula (I) into another compound of Formula (I);
ii) converting a precursor of R¹ into R¹;
iii) removing any protecting groups; and/or
iv) forming a salt thereof.

Specific reaction conditions for the above reactions are as follows, wherein when P¹ is a protecting group P¹ is preferably (1-4C)alkyl, for example methyl or ethyl:

Process a)—coupling reactions of amino groups with carboxylic acids to form an amide are well known in the art. For example,
(i) using an appropriate coupling reaction, such as a carbodiimide coupling reaction performed with EDAC (1-(3-dimethylaminopropyl)-3-ethylcarbodiimide hydrochloride) in the presence of dimethylaminopyridine (DMAP) in a suitable solvent such as dichloromethane (DCM), chloroform or dimethylformamide (DMF) at room temperature; or
(ii) reaction in which the carboxylic group is activated to an acid chloride by reaction with oxalyl chloride or 1-chloro-N,N,2-trimethyl-1-propenylamine in the presence of a suitable solvent such as DCM or DMF. The acid chloride can then be reacted with a compound of Formula (IV) in the presence of a base, such as triethylamine or pyridine, in a suitable solvent such as chloroform or DCM at a temperature between 0° C. and 80° C.

Process b)—compounds of Formula (V) and (VI) can be reacted together in a suitable solvent, such as DMF or tetrahydrofuran (THF), with a base such as sodium hydride or potassium tert-butoxide, at a temperature in the range 0 to 200° C., optionally using microwave heating or metal catalysis such as palladium(II) acetate, palladium on carbon, copper(II) acetate or copper(I) iodide; alternatively, compounds of Formula (V) and (VI) can be reacted together in a suitable solvent, such as THF or DCM, with a suitable phosphine such as triphenylphosphine, and an azodicarboxylate such as diethylazodicarboxylate; process b) could also be carried out using a precursor to the ester of formula (VII) such as an aryl-nitrile or trifluoromethyl derivative, followed by conversion to a carboxylic acid and amide formation as previously described;

Process c)—compounds of Formula (VIII) and (IX) can be reacted together in a suitable solvent, such as DMF or THF, with a base such as sodium hydride or potassium tert-butoxide, at a temperature in the range 0 to 200° C., optionally using microwave heating or metal catalysis such as palladium(II) acetate, palladium on carbon, copper(II) acetate, copper(I) iodide or bromotris(triphenylphosphine) copper(I); process c) could also be carried out using a precursor to the ester of formula (X) such as an aryl-nitrile or trifluoromethyl derivative, followed by conversion to a carboxylic acid and amide formation as previously described;

Process d)—reaction of a compound of Formula (XI) with a compound of Formula (XII) can be performed in a polar solvent, such as DMF or a non-polar solvent such as THF with a strong base, such as sodium hydride or potassium tert-butoxide at a temperature between 0 and 200° C., optionally using microwave heating or metal catalysis, such as palladium(II) acetate, palladium on carbon, copper (II) acetate or copper(I) iodide;

Process e)—coupling reactions of amino groups with carboxylic or sulfonic acids or acid derivatives to form an amide are well known in the art and are described above for Process a).

Certain intermediates of formula (III), (VI), (VII), (IX) and/or (XI) are believed to be novel and comprise an independent aspect of the invention.

Certain intermediates of formula (III), (IX) and/or (XI) wherein $R^1$ is as defined herein, are believed to be novel and comprise an independent aspect of the invention.

Certain intermediates of formula (XIII) are believed to be novel and comprise an independent aspect of the invention.

During the preparation process, it may be advantageous to use a protecting group for a functional group within the molecule. Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower" signifies that the group to which it is applied preferably has 1-4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxy protecting group may be the residue of an ester-forming aliphatic or araliphatic alcohol or of an ester-forming silanol (the said alcohol or silanol preferably containing 1-20 carbon atoms). Examples of carboxy protecting groups include straight or branched chain (1-12C)alkyl groups (e.g. isopropyl, t-butyl); lower alkoxy lower alkyl groups (e.g. methoxymethyl, ethoxymethyl, isobutoxymethyl; lower aliphatic acyloxy lower alkyl groups, (e.g. acetoxymethyl, propionyloxymethyl, butyryloxymethyl, pivaloyloxymethyl); lower alkoxycarbonyloxy lower alkyl groups (e.g. 1-methoxycarbonyloxyethyl, 1-ethoxycarbonyloxyethyl); aryl lower alkyl groups (e.g. p-methoxybenzyl, o-nitrobenzyl, p-nitrobenzyl, benzhydryl and phthalidyl); tri(lower alkyl) silyl groups (e.g. trimethylsilyl and t-butyldimethylsilyl); tri (lower alkyl)silyl lower alkyl groups (e.g. trimethylsilylethyl); and (2-6C)alkenyl groups (e.g. allyl and vinylethyl).

Methods particularly appropriate for the removal of carboxyl protecting groups include for example acid-, metal-or enzymically-catalysed hydrolysis.

Examples of hydroxy protecting groups include methyl, t-butyl, lower alkenyl groups (e.g. allyl); lower alkanoyl groups (e.g. acetyl); lower alkoxycarbonyl groups (e.g. t-butoxycarbonyl); lower alkenyloxycarbonyl groups (e.g. allyloxycarbonyl); aryl lower alkoxycarbonyl groups (e.g. benzyloxycarbonyl, p-methoxybenzyloxycarbonyl, o-nitrobenzyloxycarbonyl, p-nitrobenzyloxycarbonyl); tri lower alkyl/arylsilyl groups (e.g. trimethylsilyl, t-butyldimethylsilyl, t-butyldiphenylsilyl); tetrahydropyran-2-yl; aryl lower alkyl groups (e.g. benzyl) groups; and triaryl lower alkyl groups (e.g. triphenylmethyl).

Examples of amino protecting groups include formyl, aralkyl groups (e.g. benzyl and substituted benzyl, e.g. p-methoxybenzyl, nitrobenzyl and 2,4-dimethoxybenzyl, and triphenylmethyl); di-p-anisylmethyl and furylmethyl groups; lower alkoxycarbonyl (e.g. t-butoxycarbonyl); lower alkenyloxycarbonyl (e.g. allyloxycarbonyl); aryl lower alkoxycarbonyl groups (e.g. benzyloxycarbonyl, p-methoxybenzyloxycarbonyl, o-nitrobenzyloxycarbonyl, p-nitrobenzyloxycarbonyl; trialkylsilyl (e.g. trimethylsilyl and o-butyldimethylsilyl); alkylidene (e.g. methylidene); benzylidene and substituted benzylidene groups.

Methods appropriate for removal of hydroxy and amino protecting groups include, for example, nucleophilic displacement, acid-, base, metal-or enzymically-catalysed hydrolysis, catalytic hydrogenolysis/hydrogenation or photolytically for groups such as o-nitrobenzyloxycarbonyl, or with fluoride ions for silyl groups. For example, methylether protecting groups for hydroxy groups may be removed by trimethylsilyliodide. A tert-butyl ether protecting group for a hydroxy group may be removed by hydrolysis, for example by use of hydrochloric acid in methanol.

Examples of protecting groups for amide groups include aralkoxymethyl (e.g. benzyloxymethyl and substituted benzyloxymethyl); alkoxymethyl (e.g. methoxymethyl and trimethylsilylethoxymethyl); tri alkyl/arylsilyl (e.g. trimethylsilyl, t-butyldimethylsily, t-butyldiphenylsilyl); tri alkyl/arylsilyloxymethyl (e.g. t-butyldimethylsilyloxymethyl, t-butyldiphenylsilyloxymethyl); 4-alkoxyphenyl (e.g. 4-methoxyphenyl); 2,4-di(alkoxy)phenyl (e.g. 2,4-dimethoxyphenyl); 4-alkoxybenzyl (e.g. 4-methoxybenzyl); 2,4-di(alkoxy)benzyl (e.g. 2,4-di(methoxy)benzyl); and alk-1-enyl (e.g. allyl, but-1-enyl and substituted vinyl e.g. 2-phenylvinyl).

Aralkoxymethyl, groups may be introduced onto the amide group by reacting the latter group with the appropriate aralkoxymethyl chloride, and removed by catalytic hydrogenation. Alkoxymethyl, tri alkyl/arylsilyl and tri alkyl/silyloxymethyl groups may be introduced by reacting the amide with the appropriate chloride and removing with acid; or in the case of the silyl containing groups, fluoride ions. The alkoxyphenyl and alkoxybenzyl groups are conveniently introduced by arylation or alkylation with an appropriate halide and removed by oxidation with ceric ammonium nitrate. Finally alk-1-enyl groups may be introduced by reacting the amide with the appropriate aldehyde and removed with acid.

In the above other pharmaceutical composition, process, method, use and medicament manufacture features, the alternative and preferred aspects and embodiments of the compounds of the invention described herein also apply.

BRIEF DESCRIPTION OF THE DRAWINGS

FIG. A shows the x-ray powder diffraction, pattern of 5-[3-[(2S)-1 -(difluoromethoxy)propan-2-yl]oxy-S5-[(5-methylpyrazin-2-yl)carbamoyl]phenoxy]-N,N-dimethyl-pyrazine-2-carboxamide Form A.

FIG. B shows the DSC thermogram of 5-[3-[(2S)-1-(difluoromethoxy)propan-2-yl]oxy-5-[(5-methylpyrazin-2-yl)carbamoyl]phenoxy]-N,N-dimethyl-pyrazine-2-carboxamide Form A.

The following examples are for illustration purposes and are not intended to limit the scope of this application. Each exemplified compound represents a particular and independent aspect of the invention. In the following non-limiting Examples, unless otherwise stated:

(i) evaporations were carried out by rotary evaporation under reduced pressure and work-up procedures were carried out after removal of residual solids such as drying agents by filtration;

(ii) operations were carried out at room temperature, that is in the range 18-25° C. and under an atmosphere of an inert gas such as argon or nitrogen;

(iii) yields are given for illustration only and are not necessarily the maximum attainable;

(iv) the structures of the end-products of the Formula (I) were confirmed by nuclear (generally proton) magnetic resonance (NMR) and mass spectral techniques; proton magnetic resonance chemical shift values were measured on the delta scale and peak multiplicities are shown as follows: s, singlet; d, doublet; t, triplet; m, multiplet; br, broad; q, quartet; quin, quintet; sextet (v) intermediates were not generally fully characterised and purity was assessed by thin layer chromatography (TLC), high-performance liquid chromatography (HPLC), infra-red (IR) or NMR analysis;

(vi) flash chromatography was carried out on silica unless otherwise stated.

Abbreviations
DCM dichloromethane;
DEAD diethylazodicarboxylate;
DIAD diisopropylazodicarboxylate;
DIPEA N,N-diisopropylethylamine;
DMA dimethylacetamide;
DMSO dimethyl sulfoxide;
DMF dimethylformamide;
EDAC 1-(3-dimethylaminopropyl)-3-ethylcarbodiimide hydrochloride;
HATU 0-(7-azabenzotriazol-1-yl)-N,N,N',N'-tetramethyluronium hexofluorophosphate;
HPLC high pressure liquid chromatography;
HPMC hydroxypropylmethylcellulose;
LCMS liquid chromatography/mass spectroscopy;
NMP N-methyl-2-pyrrolidone;
NMR nuclear magnetic resonance spectroscopy;
RT room temperature;
THF tetrahydrofuran;
TFA trifluoroacetic acid;
CDCl$_3$ deuterochloroform;
MgSO$_4$ magnesium sulfate;
PTFE polytetrafluoroethylene;
TIPS triisopropylsilyl.

EXAMPLE 1

3-[(2S)-1-(difluoromethoxy)propan-2-yl]oxy-N-(5-methylpyrazin-2-yl)-5-(6-methylsulfonylpyridin-3-yl)oxy-benzamide

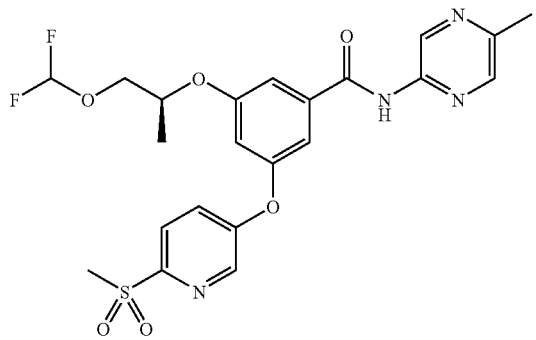

A mixture of 3-[(2S)-1-(difluoromethoxy)propan-2-yl]oxy-5-hydroxy-N-(5-methylpyrazin-2-yl)benzamide (190 mg, 0.54 mmol), 5-bromo-2-methylsulfonyl-pyridine (CAS no. 98626-95-0) (140 mg, 0.59 mmol), cesium carbonate (350 mg, 1.08 mmol) and bromotris(triphenylphosphine)copper(I) (101 mg, 0.11 mmol) in DMA (5 mL) was stirred in a microwave reactor at 160° C. for 6 hours. Ethyl acetate (50 mL) was added and the mixture washed with water (50 mL), brine (50 mL), dried (MgSO$_4$) and reduced in vacuo. The crude residue was chromatographed on silica, eluting with 10-100% ethyl acetate in isohexane, to give the desired compound (19 mg).

$^1$H NMR δ (CDCl$_3$): 1.40 (d, 3H), 2.56 (s, 3H), 3.23 (s, 3H), 3.96-4.05 (m, 2H), 4.65-4.72 (m, 1H), 6.26 (t, 1H), 6.86 (t, 1H), 7.21 (t, 1H), 7.36 (t, 1H), 7.46-7.49 (m, 1H), 8.08 (d, 1H), 8.15 (s, 1H), 8.30 (s, 1H), 8.49 (d, 1H), 9.52 (d, 1H); m/z 509 (M+H)$^+$

The preparation of 3-[(2S)-1-(difluoromethoxy)propan-2-yl]oxy-5-hydroxy-N-(5-methylpyrazin-2-yl)benzamide is described below.

3-[(2S)-1-(Difluoromethoxy)propan-2-yl]oxy-5-hydroxy-N-(5-methylpyrazin-2-yl)benzamide

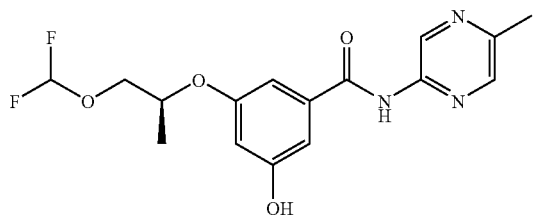

3-[(2S)-1-(difluoromethoxy)propan-2-yl]oxy-N-(5-methylpyrazin-2-yl)-5-phenylmethoxy-benzamide (0.48 g, 1.08 mmol) was dissolved in ethanol (10 mL) and THF (10 mL)

and the flask evacuated and purged with argon (3 times). 10% Palladium on carbon (48 mg) was added and the flask further evacuated and finally purged with hydrogen gas. The reaction mixture was stirred at RT for 20 hours. The reaction mixture was evacuated and purged with argon (3 times) and the catalyst removed by filtration through Celite®. The filtrate was concentrated in vacuo to give the desired compound (0.38 g).

$^1$H NMR δ (d$_6$-DMSO): 1.19 (d, 3H), 2.39 (s, 3H), 3.85-3.95 (m, 2H), 4.65-4.72 (m, 1H), 6.46 (s, 1H), 6.65 (t, 1H), 6.93 (s, 1H), 7.06 (s, 1H), 8.27 (s, 1H), 9.16 (s, 1H), 9.74 (s, 1H), 10.82 (s, 1H); m/z 354 (M+H)$^+$

3-[(2S)-1-(difluoromethoxy)propan-2-yl]oxy-N-(5-methylpyrazin-2-yl)-5-phenylmethoxy-benzamide

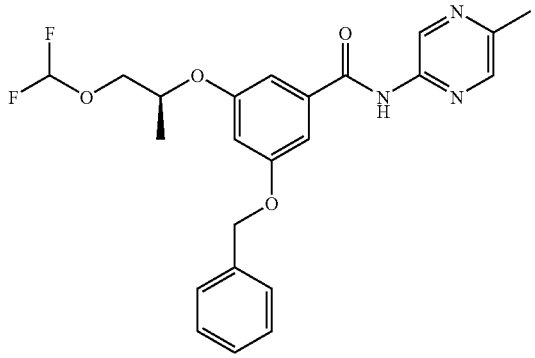

1-Chloro-N,N,2-trimethyl-prop-1-en-1-amine (0.26 mL, 2.0 mmol) was added to a solution of 3-[(2S)-1-(difluoromethoxy)propan-2-yl]oxy-5-phenylmethoxy-benzoic acid (0.54 g, 1.5 mmol) in DCM (20 mL) and stirred for 1 hour. 5-Methylpyrazin-2-amine (CAS no. 5521-58-4) (335 mg, 3.1 mmol) then pyridine (0.25 mL, 3.1 mmol) were added and the reaction stirred for a further 30 minutes before being reduced in vacuo and partitioned between ethyl acetate (50 mL) and water (50 mL). The aqueous layer was further extracted into ethyl acetate (50 mL) and the combined organics washed with water (50 mL), brine (50 mL), dried (MgSO$_4$), and reduced in vacuo. The crude residue was chromatographed on silica, eluting with 40-100% ethyl acetate in isohexane, to give the desired compound (0.48 g).

$^1$H NMR δ (CDCl$_3$): 1.39 (d, 3H), 2.58 (s, 3H), 3.96-4.05 (m, 2H), 4.63-4.70 (m, 1H), 5.13 (s, 2H), 6.30 (t, 1H), 6.78 (t, 1H), 7.09 (t, 1H), 7.16 (t, 1H), 7.35-7.48 (m, 5H), 8.17 (s, 1H), 8.39 (s, 1H), 9.58 (d, 1H); m/z 444 (M+H)$^+$

3-[(2S)-1-(difluoromethoxy)propan-2-yl]oxy-5-phenylmethoxy-benzoic acid

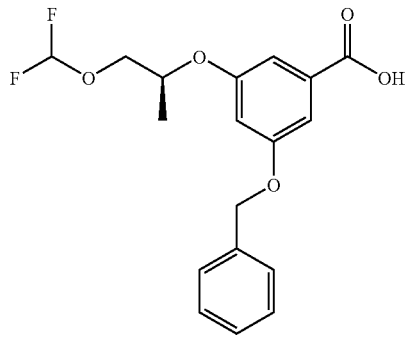

Lithium hydroxide monohydrate (19 mg, 0.45 mmol) in water (2 mL) was added to methyl 3-[(2S)-1-(difluoromethoxy)propan-2-yl]oxy-5-phenylmethoxy-benzoate (0.11 g, 0.3 mmol) in THF (4 mL) and the mixture stirred at RT for 20 hours. The THF was removed in vacuo and the aqueous layer adjusted to pH 3 with citric acid then extracted into ethyl actetate (2×30 mL). The organics were washed with water (30 mL), brine (30 mL), dried (MgSO$_4$), filtered and the solvent removed in vacuo to give the desired compound (0.1 g).

$^1$H NMR δ (d$_6$-DMSO): 1.27 (d, 3H), 4.00 (m, 2H), 4.75 (sextet, 1H), 5.15 (s, 2H), 6.72 (t, 1H), 6.87 (t, 1H), 7.08 (t, 1H), 7.16 (t, 1H), 7.41 (m, 5H), 12.95 (s, 1H); m/z 351 (M+H)$^+$ Methyl 3-[(2S)-1-(difluoromethoxy)propan-2-yl]oxy-5-phenylmethoxy-benzoate

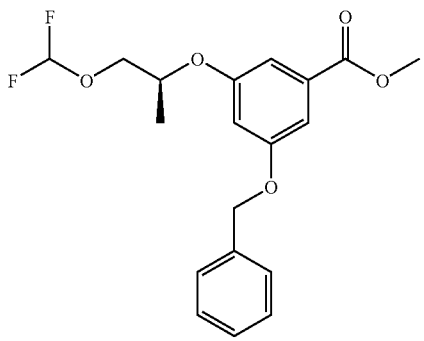

2,2-Difluoro-2-fluorosulfonyl-acetic acid (CAS no. 1717-59-5) (0.239 mL, 2.31 mmol) was added dropwise, with stirring, to a degassed mixture of methyl 3-[(2S)-1-hydroxypropan-2-yl]oxy-5-phenylmethoxy-benzoate (0.73 g, 2.31 mmol) and copper (I) iodide (88 mg, 0.46 mmol) in acetonitrile (10 mL) at 45° C. The reaction was stirred at 45° C. for 24 hours. The solvent was removed in vacuo and ethyl acetate (30 mL) added. The organics were washed with water (30 mL), brine (30 mL), dried (MgSO$_4$), filtered and the solvent removed in vacuo. The residue was chromatographed on silica, eluting with a gradient of 0-30% ethyl acetate in isohexane, to give the desired compound (0.11 g).

$^1$H NMR δ (CDCl$_3$): 1.37 (d, 3H), 3.93 (s, 3H), 4.00 (m, 2H), 4.63 (sextet, 1H), 5.10 (s, 2H), 6.28 (t, 1H), 6.77 (t, 1H), 7.28 (t, 1H), 7.41 (m, 6H); m/z 367 (M+H)$^+$ Methyl 3-[(2S)-1-hydroxypropan-2-yl]oxy-5-phenylmethoxy-benzoate

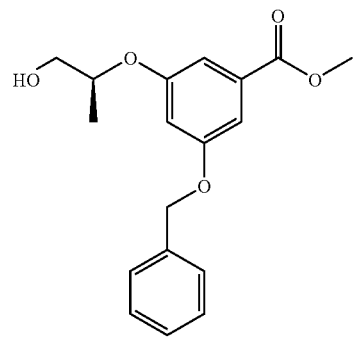

Bromomethylbenzene (1.89 g, 7.20 mmol) was added to a mixture of methyl 3-hydroxy-5-[(2S)-1-hydroxypropan-2- yl]oxy-benzoate (1.55 g, 6.86 mmol) and potassium carbonate (1.89 g, 0.014 mol) in DMF (16 mL) and the reaction stirred at RT for 20 hours. Ethyl acetate (40 mL) was added and the mixture washed with water (40 mL), saturated sodium bicarbonate solution (40 mL), brine (40 mL), dried (MgSO$_4$), filtered and the solvent removed in vacuo. The residue was chromatographed on silica, eluting with a gradient of 0-100% ethyl acetate in isohexane, to give the desired compound (1.7 g).

$^1$H NMR δ (CDCl$_3$): 1.30 (d, 3H), 1.95 (m, 1H), 3.76 (m, 2H), 3.92 (s, 3H), 4.53 (m, 1H), 5.11 (s, 2H), 6.78 (t, 1H), 7.25 (m, 1H), 7.32 (m, 1H), 7.45 (m, 5H); m/z 317 (M+H)$^+$

Methyl 3-hydroxy-5-[(2S)-1-hydroxypropan-2-yl]oxy-benzoate

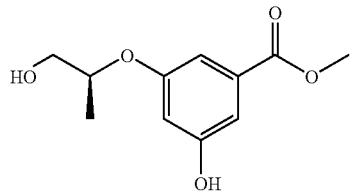

Iodo-trimethyl-silane (CAS no. 16029-98-4) (115 mL, 0.79 mol) was added to a solution of methyl 3-hydroxy-5-[(2S)-1-methoxypropan-2-yl]oxy-benzoate (CAS no. 863504-77-2) (38.01 g, 0.158 mol) in acetonitrile (500 mL) and stirred for 24 hours. Methanol (300 mL) was added and the reaction stirred for 10 minutes. 10% w/v Aqueous sodium thiosulfate pentahydrate (100 mL) was added to the mixture and stirred for 20 minutes. The reaction mixture was neutralised with saturated aqueous sodium bicarbonate solution, the organic solvents removed in vacuo, and the product extracted into ethyl acetate (4×100 mL). The combined organic layers were dried (MgSO$_4$), filtered and the solvents removed in vacuo. The crude material was crystallised from ethyl acetate to give the desired compound (16.8 g).

$^1$H NMR δ (d$_6$-DMSO): 1.18 (d, 3H), 3.40-3.55 (m, 2H), 3.80 (s, 3H), 4.35 (sextet, 1H), 4.80 (t, 1H), 6.57 (m, 1H), 6.90 (m, 2H), 9.75 (s, 1H); m/z 304 (M+H)$^+$ Methyl 3-hydroxy-5-[(2S)-1-methoxypropan-2-yl]oxy-benzoate

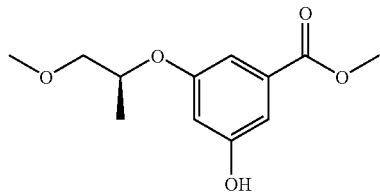

Methyl 3-[(2S)-1-methoxypropan-2-yl]oxy-5-phenylmethoxy-benzoate (CAS no. 851885-42-2) (50.0 g, 0.152 mmol) was dissolved in a mixture of THF:ethanol (600 mL) and the flask evacuated and purged with nitrogen (3 times). 10% Palladium on carbon (5.0 g) was added and the flask further evacuated and finally purged with hydrogen gas. The reaction mixture was stirred at ambient temperature for 20 hours until completion. The reaction mixture was evacuated and purged with nitrogen (3 times). The catalyst was filtered off, and the filtrate concentrated in vacuo to give the desired compound (36.7 g).

$^1$H NMR δ (d$_6$-DMSO): 1.2 (d, 3H), 3.25 (s, 3H), 3.44 (m, 2H), 3.82 (s, 3H), 4.55 (m, 1H), 6.6 (s, 1H), 6.9 (s, 1H), 6.95 (s, 1H), 9.8 (s, 1H)

EXAMPLE 2

5-[3-[(2S)-1-(difluoromethoxy)propan-2-yl]oxy-5-[(5-methylpyrazin-2-yl)carbamoyl]phenoxy]-N,N-dimethyl-pyrazine-2-carboxamide

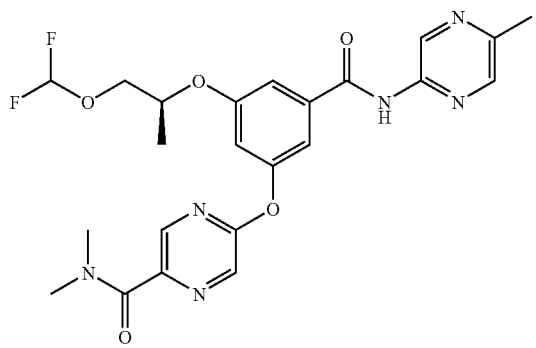

A mixture of 3-[(2S)-1-(difluoromethoxy)propan-2-yl]oxy-5-hydroxy-N-(5-methylpyrazin-2-yl)benzamide (0.19 g, 0.54 mmol), 5-chloro-N,N-dimethyl-pyrazine-2-carboxamide (100 mg, 0.54 mmol) and potassium carbonate (149 mg, 1.08 mmol) in acetonitrile (5 mL) was stirred in a microwave reactor at 140° C. for 5 hours and the mixture reduced in vacuo. Ethyl acetate (50 mL) was added and the mixture washed with water (50 mL), brine (50 mL), dried (MgSO$_4$), and reduced in vacuo. The crude residue was chromatographed on silica, eluting with 0-5% methanol in DCM, to give the desired compound (150 mg).

$^1$H NMR δ (CDCl$_3$): 1.40 (d, 3H), 2.55 (s, 3H), 3.15 (s, 3H), 3.18 (s, 3H), 3.95-4.05 (m, 2H), 4.64-4.71 (m, 1H), 6.26 (t, 1H), 6.97 (t, 1H), 7.32 (t, 1H), 7.40 (t, 1H), 8.13 (s, 1H), 8.38 (d, 1H), 8.41 (s, 1H), 8.53 (d, 1H), 9.53 (d, 1H); m/z 503 (M+H)$^+$

The preparation of 3-[(2S)-1-(difluoromethoxy)propan-2-yl]oxy-5-hydroxy-N-(5-methylpyrazin-2-yl)benzamide was described previously.

The preparation of 5-chloro-N,N-dimethyl-pyrazine-2-carboxamide is described below.

5-Chloro-N,N-dimethyl-pyrazine-2-carboxamide

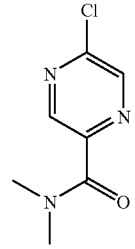

Oxalyl chloride (1.7 mL, 19 mmol) was added to a suspension of 5-chloropyrazine-2-carboxylic acid (CAS no. 36070-80-1) (2.53 g, 16.0 mmol) in dichloromethane (25 mL) and DMF (4 drops) at RT and under argon. The mixture was allowed to stir for 1.5 h, concentrated in vacuo to and the residue was re-dissolved in dichloromethane (25 mL). Dimethylamine (2M in THF, 8.77 mL, 17.6 mmol) was then added dropwise followed by triethylamine (4.9 mL, 35 mmol) and allowed to stir for a further 5.5 hours. The reaction mixture was concentrated in vacuo and the residue was re-dissolved in dichloromethane and filtered. The filtrate was chromatographed on silica, eluting with a gradient of 50-100% ethyl acetate in isohexanes to give the desired compound (1.88 g).

$^1$H NMR δ (CD$_3$OD): 3.34 (s, 3H), 3.38 (s, 3H), 8.90 (s, 1H), 8.92 (s, 1H); m/z 186 (M+H)$^+$

An alternative method for the preparation of 5-[3-[(2S)-1-(difluoromethoxy)propan-2-yl]oxy-5-[(5-methylpyrazin-2-yl)carbamoyl]phenoxy]-N,N-dimethyl-pyrazine-2-carboxamide is given below:

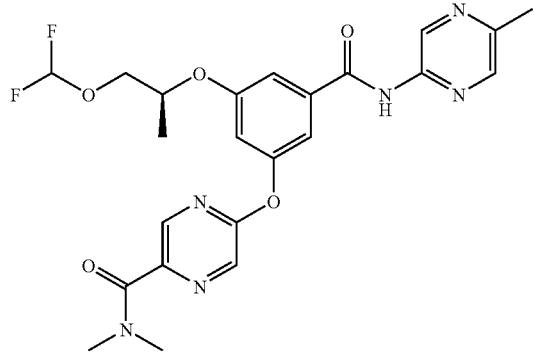

1-Chloro-N,N,2-trimethyl-1-propenylamine (6.9 mL, 52.3 mmol) was added to a solution of 3-[(2S)-1-(difluoromethoxy)propan-2-yl]oxy-5-[5-(dimethylcarbamoyl)pyrazin-2-yl]oxy-benzoic acid (17.2 g, 41.8 mmol) in DCM (250 mL) and stirred at ambient temperature for 30 minutes. 5-Methylpyrazin-2-amine (9.1 g, 83.6 mmol) and pyridine (6.8 mL, 83.6 mmol) were added and the reaction stirred overnight. The solvent was evaporated under reduced pressure. The residue was dissolved in ethyl acetate (200 mL), washed with water (2×100 mL), citric acid (1N, 100 mL), saturated sodium bicarbonate solution (2×100 mL) and saturated brine (10 mL), dried (MgSO$_4$), filtered and evaporated under reduced pressure. The residue was purified by flash chromatography on silica, eluting with a gradient of 25-100% ethyl acetate in isohexane to afford the product as a colourless foam (11.2 g). To a 200 mg sample of this material was added diethyl ether (1 mL) and the resulting suspension slurried overnight with vigorous stirring. The resulting white solid was isolated by filtration and dried under vacuum. X-ray powder diffraction established this material to contain a large degree of crystalline character. The remaining material (9.2 g) was split in to two batches (3.5 g and 5.7 g). To the smaller batch (3.5 g) was added diethyl ether (12.5 mL) and to the larger batch (5.7 g) was added diethyl ether (20 mL). The larger batch was seeded with the crystalline material obtained previously (50 mg). Both batches were stirred for 16 hours at room temperature. The resulting colourless solids were isolated by filtration, combined and dried in vacuum. The resulting material (6.1 g, 29%) had an X-ray powder diffraction pattern consistent with the crystalline material obtained previously and with that described for 5-[3-[(2S)-1-(difluoromethoxy)propan-2-yl]oxy-5-[(5-methylpyrazin-2-yl)carbamoyl]phenoxy]-N,N-dimethyl-pyrazine-2-carboxamide Form A described below. $^1$H NMR and mass spectrometry data were consistent with those obtained using the previous method. 5-[3-[(2S)-1-(difluoromethoxy)propan-2-yl]oxy-5-[(5-methylpyrazin-2-yl)carbamoyl]phenoxy]-N,N-dimethyl-pyrazine-2-carboxamide Form A is characterised in providing at least one of the following 2θ values measured using CuKa radiation: 20.3 and 15.6. 5-[3-[(2S)-1-(difluoromethoxy)propan-2-yl]oxy-5-[(5-methylpyrazin-2-yl)carbamoyl]phenoxy]-N,N-dimethyl-pyrazine-2-carboxamide Form A is characterised in providing an X-ray powder diffraction pattern, substantially as shown in Figure A. The ten most prominent peaks are shown in Table A:

TABLE A

Ten most Prominent X-Ray Powder Diffraction peaks for 5-[3-[(2S)-l-difluoromethoxy)propan-2-yl]oxy-5-[(5-methylpyrazin-2-yl)carbamoyl]phenoxy]-N,N-dimethyl-pyrazine-2-carboxamide Form A

| Angle 2-Theta (2θ) | Intensity % | Relative Intensity |
|---|---|---|
| 20.325 | 100 | vs |
| 15.646 | 94.3 | vs |
| 23.15 | 46.2 | vs |
| 22.424 | 43.8 | vs |
| 9.266 | 39.1 | vs |
| 25.707 | 34.8 | vs |
| 26.21 | 32.9 | vs |
| 18.72 | 28.5 | vs |
| 26.485 | 28.5 | vs |
| 8.425 | 28.5 | vs | vs = very strong

According to the present invention there is provided a crystalline form of 5-[3-[(2S)-1-(difluoromethoxy)propan-2-yl]oxy-5-[(5-methylpyrazin-2-yl)carbamoyl]phenoxy]-N,N-dimethyl-pyrazine-2-carboxamide, Form A, which has an X-ray powder diffraction pattern with at least one specific peak at about 2-theta=20.3θ.

According to the present invention there is provided a crystalline form, Form A, which has an X-ray powder diffraction pattern with at least one specific peak at about 2-theta=15.6°.

According to the present invention there is provided a crystalline form of 5-[3-[(2S)-1-(difluoromethoxy)propan-2-yl]oxy-5-[(5-methylpyrazin-2-yl)carbamoyl]phenoxy]-N,N-dimethyl-pyrazine-2-carboxamide, Form A, which has an X-ray powder diffraction pattern with at least two specific peaks at about 2-theta=20.3θ and 15.6°.

According to the present invention there is provided a crystalline form of 5-[3-[(2S)-1-(difluoromethoxy)propan-2-yl]oxy-5-[(5-methylpyrazin-2-yl)carbamoyl]phenoxy]-N,N-dimethyl-pyrazine-2-carboxamide, Form A, which has an X-ray powder diffraction pattern with specific peaks at about 2-theta=20.3, 15.6, 23.2, 22.4, 9.3, 25.7, 26.2, 18.7, 26.5 and 8.4°.

According to the present invention there is provided crystalline form of 5-[3-[(2S)-1-(difluoromethoxy)propan-2-yl]oxy-5-[(5-methylpyrazin-2-yl)carbamoyl]phenoxy]-N,N-dimethyl-pyrazine-2-carboxamide, Form A, which has an X-ray powder diffraction pattern substantially the same as the X-ray powder diffraction pattern shown in Figure A.

According to the present invention there is provided crystalline form of 5-[3-[(2S)-1-(difluoromethoxy)propan-2-yl]oxy-5-[(5-methylpyrazin-2-yl)carbamoyl]phenoxy]-N,N-dimethyl-pyrazine-2-carboxamide, Form A, which has an X-ray powder diffraction pattern with at least one specific peak at 2-theta=20.3° plus or minus 0.5° 2-theta.

According to the present invention there is provided a crystalline form of 5-[3-[(2S)-1-(difluoromethoxy)propan-2-yl]oxy-5-[(5-methylpyrazin-2-yl)carbamoyl]phenoxy]-N,N-dimethyl-pyrazine-2-carboxamide, Form A, which has an X-ray powder diffraction pattern with at least one specific peak at 2-theta=15.6° plus or minus 0.5° 2-theta.

According to the present invention there is provided a crystalline form of 5-[3-[(2S)-1-(difluoromethoxy)propan-2-yl]oxy-5-[(5-methylpyrazin-2-yl)carbamoyl]phenoxy]-N,N-dimethyl-pyrazine-2-carboxamide, Form A, which has an X-ray powder diffraction pattern with at least two specific peaks at 2-theta=20.3° and 15.6° wherein said values may be plus or minus 0.5° 2-theta.

According to the present invention there is provided a crystalline form of 5-[3-[(2S)-1-(difluoromethoxy)propan-2-yl]oxy-5-[(5-methylpyrazin-2-yl)carbamoyl]phenoxy]-N,N-dimethyl-pyrazine-2-carboxamide, Form A, which has an X-ray powder diffraction pattern with specific peaks at 2-theta=20.3, 15.6, 23.2, 22.4, 9.3, 25.7, 26.2, 18.7, 26.5 and 8.4° wherein said values may be plus or minus 0.5° 2-theta.

According to the present invention there is provided a crystalline form of 5-[3-[(2S)-1-(difluoromethoxy)propan-2-yl]oxy-5-[(5-methylpyrazin-2-yl)carbamoyl]phenoxy]-N,N-dimethyl-pyrazine-2-carboxamide, Form A, which has an X-ray powder diffraction pattern with at least one specific peak at 2-theta=20.3°.

According to the present invention there is provided a crystalline form of 5-[3-[(2S)-1-(difluoromethoxy)propan-2-yl]oxy-5-[(5-methylpyrazin-2-yl)carbamoyl]phenoxy]-N,N-dimethyl-pyrazine-2-carboxamide, Form A, which has an X-ray powder diffraction pattern with at least one specific peak at 2-theta=15.6°.

According to the present invention there is provided a crystalline form of 5-[3-[(2S)-1-(difluoromethoxy)propan-2-yl]oxy-5-[(5-methylpyrazin-2-yl)carbamoyl]phenoxy]-N,N-dimethyl-pyrazine-2-carboxamide, Form A, which has an X-ray powder diffraction pattern with at least two specific peaks at 2-theta=20.3° and 15.6°.

According to the present invention there is provided a crystalline form of 5-[3-[(2S)-1-(difluoromethoxy)propan-2-yl]oxy-5-[(5-methylpyrazin-2-yl)carbamoyl]phenoxy]-N,N-dimethyl-pyrazine-2-carboxamide, Form A, which has an X-ray powder diffraction pattern with specific peaks at 2-theta=20.3, 15.6, 23.2, 22.4, 9.3, 25.7, 26.2, 18.7, 26.5 and 8.4°.

According to the present invention there is provided a crystalline form of 5-[3-[(2S)-1-(difluoromethoxy)propan-2-yl]oxy-5-[(5-methylpyrazin-2-yl)carbamoyl]phenoxy]-N,N-dimethyl-pyrazine-2-carboxamide, Form A, which has an X-ray powder diffraction pattern as shown in Figure A.

DSC analysis shows 5-[3-[(2S)-1-(difluoromethoxy)propan-2-yl]oxy-5-[(5-methylpyrazin-2-yl)carbamoyl]phenoxy]-N,N-dimethyl-pyrazine-2-carboxamide Form A is a low melting solid with an onset of melting at 75.0° C. and a peak at 83.1° C. (Figure B).

According to the present invention there is therefore provided a crystalline form of 5-[3-[(2S)-1-(difluoromethoxy)propan-2-yl]oxy-5-[(5-methylpyrazin-2-yl)carbamoyl]phenoxy]-N,N-dimethyl-pyrazine-2-carboxamide, Form A, with an onset of melting at about 75.0° C. and a peak at about 83.1° C.

According to the present invention there is therefore provided a process for the formation of a crystalline form of 5-[3-[(2S)-1-(difluoromethoxy)propan-2-yl]oxy-5-[(5-methylpyrazin-2-yl)carbamoyl]phenoxy]-N,N-dimethyl-pyrazine-2-carboxamide which comprises crystallisation of 5-[3-[(2S)-1-(difluoromethoxy)propan-2-yl]oxy-5-[(5-methylpyrazin-2-yl)carbamoyl]phenoxy]-N,N-dimethyl-pyrazine-2-carboxamide from a solution of 5-[3-[(2S)-1-(difluoromethoxy)propan-2-yl]oxy-5-[(5-methylpyrazin-2-yl)carbamoyl]phenoxy]-N,N-dimethyl-pyrazine-2-carboxamide in diethyl ether.

When it is stated that the present invention relates to a crystalline form of 5-[3-[(2S)-1-(difluoromethoxy)propan-2-yl]oxy-5-[(5-methylpyrazin-2-yl)carbamoyl]phenoxy]-N,N-dimethyl-pyrazine-2-carboxamide Form A, the degree of crystallinity is conveniently greater than about 60%, more conveniently greater than about 80%, preferably greater than about 90% and more preferably greater than about 95%.

The 5-[3-[(2S)-1-(difluoromethoxy)propan-2-yl]oxy-5-[(5-methylpyrazin-2-yl)carbamoyl]phenoxy]-N,N-dimethyl-pyrazine-2-carboxamide Form A provides X-ray powder diffraction patterns substantially the same as the X-ray powder diffraction patterns shown in Figure A and has substantially the ten most prominent peaks (angle 2-theta values) shown in Table A. It will be understood that the 2-theta values of the X-ray powder diffraction pattern may vary slightly from one machine to another or from one sample to another, and so the values quoted are not to be construed as absolute.

It is known that an X-ray powder diffraction pattern may be obtained which has one or more measurement errors depending on measurement conditions (such as equipment or machine used). In particular, it is generally known that intensities in an X-ray powder diffraction pattern may fluctuate depending on measurement conditions. Therefore it should be understood that the 5-[3-[(2S)-1-(difluoromethoxy)propan-2-yl]oxy-5-[(5-methylpyrazin-2-yl)carbamoyl]phenoxy]-N,N-dimethyl-pyrazine-2-carboxamide Form A of the present invention is not limited to the crystals that provide X-ray powder diffraction patterns identical to the X-ray powder diffraction pattern shown in Figure A, and any crystals providing X-ray powder diffraction patterns substantially the same as those shown in Figure A fall within the scope of the present invention. A person skilled in the art of X-ray powder diffraction is able to judge the substantial identity of X-ray powder diffraction patterns.

Persons skilled in the art of X-ray powder diffraction will realise that the relative intensity of peaks can be affected by, for example, grains above 30 microns in size and non-unitary aspect ratios, which may affect analysis of samples. The skilled person will also realise that the position of reflections can be affected by the precise height at which the sample sits in the diffractometer and the zero calibration of the diffractometer. The surface planarity of the sample may also have a small effect. Hence the diffraction pattern data presented are not to be taken as absolute values. (Jenkins, R & Snyder, R. L. 'Introduction to X-Ray Powder Diffractometry' John Wiley & Sons 1996; Bunn, C. W. (1948), Chemical Crystallography, Clarendon Press, London; Klug, H. P. & Alexander, L. E. (1974), X-Ray Diffraction Procedures).

Generally, a measurement error of a diffraction angle in an X-ray powder diffractogram is about 5% or less, in particular plus or minus 0.5° 2-theta, and such degree of a measurement error should be taken into account when considering the X-ray powder diffraction pattern in Figure A and when reading Table A. Furthermore, it should be understood that intensities might fluctuate depending on experimental conditions and sample preparation (preferred orientation).

Details of Techniques Used

X-Ray Powder Diffraction

TABLE B

| % Relative Intensity* | Definition |
|---|---|
| 25-100 | vs (very strong) |
| 10-25 | s (strong) |

TABLE B-continued

| % Relative Intensity* | Definition |
|---|---|
| 3-10 | m (medium) |
| 1-3 | w (weak) |

*The relative intensities are derived from diffractograms measured with fixed slits
Analytical Instrument: Siemens D5000.

The X-ray powder diffraction spectra were determined by mounting a sample of the crystalline material on a Siemens single silicon crystal (SSC) wafer mount and spreading out the sample into a thin layer with the aid of a microscope slide. The sample was spun at 30 revolutions per minute (to improve counting statistics) and irradiated with X-rays generated by a copper long-fine focus tube operated at 40 kV and 40 mA with a wavelength of 1.5406 angstroms. The collimated X-ray source was passed through an automatic variable divergence slit set at V20 and the reflected radiation directed through a 2 mm antiscatter slit and a 0.2 mm detector slit. The sample was exposed for 1 second per 0.02 degree 2-theta increment (continuous scan mode) over the range 2 degrees to 40 degrees 2-theta in theta-theta mode. The running time was 31 minutes and 41 seconds. The instrument was equipped with a scintillation counter as detector. Control and data capture was by means of a Dell Optiplex 686 NT 4.0 Workstation operating with Diffract+ software. Persons skilled in the art of X-ray powder diffraction will realise that the relative intensity of peaks can be affected by, for example, grains above 30 microns in size and non-unitary aspect ratios that may affect analysis of samples. The skilled person will also realise that the position of reflections can be affected by the precise height at which the sample sits in the diffractometer and the zero calibration of the diffractometer. The surface planarity of the sample may also have a small effect. Hence the diffraction pattern data presented are not to be taken as absolute values.

Differential Scanning Calorimetry

Analytical Instrument: Mettler DSC820e.

Typically less than 5 mg of material contained in a 40 μl aluminium pan fitted with a pierced lid was heated over the temperature range 25° C. to 325° C. at a constant heating rate of 10° C. per minute. A purge gas using nitrogen was used—flow rate 100 ml per minute.

Slurrying of 5-[3-[(2S)-1-(difluoromethoxy)propan-2-yl]oxy-5-[(5-methylpyrazin-2-yl)carbamoyl]phenoxy]-N,N-dimethyl-pyrazine-2-carboxamide The X-ray powder diffraction spectra for 5-[3-[(2S)-1-(difluoromethoxy)propan-2-yl]oxy-5-[(5-methylpyrazin-2-yl)carbamoyl]phenoxy]-N,N-dimethyl-pyrazine-2-carboxamide showed the initial material to be amorphous. In order to produce the crystalline form, Form A, approximately 500 mg of material was placed in a vial with a magnetic follower, and approximately 2 ml of Diethyl Ether added, the vial was then sealed tightly with a cap. The slurry was then left to stir on a magnetic plate at ambient temperature (25° C.). After 2 days, the sample was removed from the plate, the cap taken off and the slurry left to dry under ambient conditions before it was analysed by XRPD and DSC. The resulting material (Form A) was determined to be crystalline by XRPD and seen to be different from the initial amorphous material. This material (Form A) had a melting point of 75.0° C. (onset).

3-[(2S)-1-(Difluoromethoxy)propan-2-yl]oxy-5-[5-(dimethylcarbamoyl)pyrazin-2-yl]oxy-benzoic acid

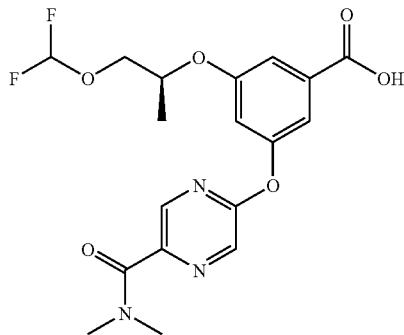

Methyl 3-[(2S)-1-(difluoromethoxy)propan-2-yl]oxy-5-[5-(dimethylcarbamoyl)pyrazin-2-yl]oxy-benzoate (19.8 g, 46.6 mmol) was dissolved in THF (300 mL) and methanol (100 mL) and LiOH (1N, 51.3 mL) was added followed by water dropwise till it went cloudy. The resultant solution was stirred for 16 hours at room temperature. The organics were removed by evaporation under reduced pressure. The aqueous slurry was diluted with water (100 mL), washed with ethyl acetate (200 mL), then acidified by addition of hydrochloric acid (2N) until a solid precipitated. The resulting suspension was extracted with ethyl acetate (2×200 mL). The combined organic extracts were washed with water (200 mL) and brine (200 mL), dried (MgSO$_4$), filtered and concentrated under reduced pressure to afford the product (17.2 g, 90%).
$^1$H NMR δ (CDCl$_3$): 1.39 (d, 3H), 3.17 (s, 3H), 3.19 (s, 3H), 3.93-4.05 (m, 2H), 4.60-4.69 (m, 1H), 6.26 (t, 1H), 6.99 (t, 1H), 7.50-7.55 (m, 2H), 8.38 (d, 1H), 8.55 (d, 1H), 10.17 (s, 1H); m/z 412 (M+H)$^+$ Methyl 3-[(2S)-1-(difluoromethoxy)propan-2-yl]oxy-5-[5-(dimethylcarbamoyl)pyrazin-2-yl]oxy-benzoate

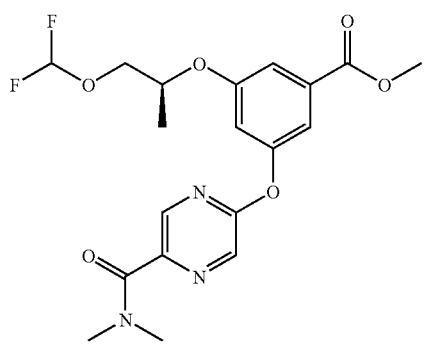

2,2-Difluoro-2-fluorosulfonyl-acetic acid (CAS no. 1717-59-5) (0.84 mL, 8.05 mmol) in acetonitrile (20 mL) was added with a syringe pump dropwise over 90 minutes to a degassed stirring mixture of methyl 3-[5-(dimethylcarbamoyl)pyrazin-2-yl]oxy-5-[(2S)-1-hydroxypropan-2-yl]oxy-benzoate (1.5 g, 22.0 mmol) and copper (I) iodide (154 mg, 4.55 mmol) in acetonitrile (300 mL) at 55° C. The volatiles were removed under reduced pressure and the residue taken up in DCM. The mixture was filtered to and the solvent was removed under reduced pressure. The residue was purified by flash chromatography on silica, eluting with a gradient of 25%-100% ethyl acetate in isohexane to afford the product (16.5 g, 62%). ¹H NMR δ (CDCl₃): 1.38 (3H, d), 3.15 (3H, s), 3.18 (3H, s), 3.91 (3H, s), 3.93-4.05 (2H, m), 4.62-4.68 (1H, m), 6.27 (1H, t), 6.95 (1H, t), 7.44-7.45 (1H, m), 7.49-7.51 (1H, m), 8.36 (1H, s), 8.53 (1H, s); m/z 404 (M+H⁺)

Methyl 3-[5-(dimethylcarbamoyl)pyrazin-2-yl]oxy-5-[(2S)-1-hydroxypropan-2-yl]oxy-benzoate

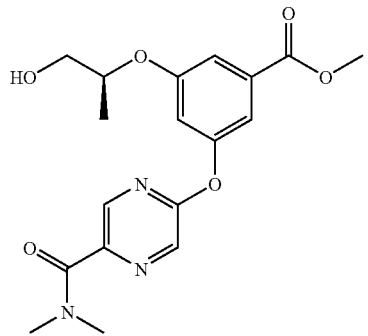

A solution of hydrogen fluoride (70% in pyridine, 3.25 mL) was added to methyl 3-[5-(dimethylcarbamoyl)pyrazin-2-yl]oxy-5-[(2S)-1-tripropan-2-ylsilyloxypropan-2-yl]oxy-benzoate in THF (300 mL) in a PTFE vessel and the resulting solution stirred for 18 hours at room temp. Further hydrogen fluoride solution (70% in pyridine, 3.25 mL) was added and the reaction stirred for an additional 66 hours. The reaction was quenched by the very careful addition of saturated aqueous sodium bicarbonate solution until the solution reached pH 8. The aqueous layer was extracted with ethyl acetate (2×500 mL) and the combined organics dried (MgSO₄). The solvent was removed under reduced pressure and the residue was purified by flash column chromatography on silica eluting with 25 to 100% ethyl acetate in isohexane to afford the product (13.2 g, 98%). ¹H NMR δ (CDCl₃) 1.32 (3H, d), 1.93 (1H, d), 3.17 (6H, d), 3.74-3.79 (1H, m), 3.91 (3H, s), 4.54-4.60 (1H, m), 6.96 (1H, t), 7.43 (1H, d), 7.51 (1H, d), 8.36 (1H, d), 8.53 (1H, d); m/z 376 (M+H⁺)

Methyl 3-[5-(dimethylcarbamoyl)pyrazin-2-yl]oxy-5-[(2S)-1-tripropan-2-ylsilyloxypropan-2-yl]oxy-benzoate

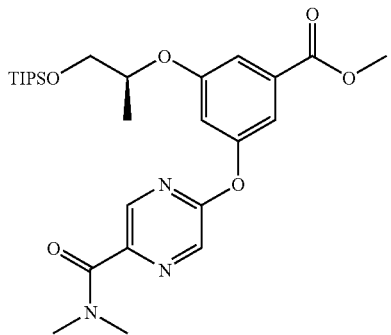

A mixture of methyl 3-hydroxy-5-[(2S)-1-tripropan-2-ylsilyloxypropan-2-yl]oxy-benzoate (40.2 g, 105 mmol), 5-chloro-N,N-dimethyl-pyrazine-2-carboxamide (20.5 g, 110 mmol) and potassium carbonate (36.3 g, 263 mmol) in acetonitrile (500 mL) was stirred at reflux for 6 hours. The volatiles were removed under reduced pressure and ethyl acetate (500 mL) and water (500 mL) were added. The organic layer was separated, the aqueous layer was re-extracted into ethyl acetate (250 mL) and the combined organics washed with water (500 mL), brine (500 mL), dried (MgSO₄), filtered and concentrated under reduced pressure to afford the product (55.6 g, 100%). ¹H NMR δ (CDCl₃) 1.01-1.07 (21H, m), 1.34 (3H, d), 3.14-3.16 (3H, s), 3.17 (3H, s), 3.72-3.77 (1H, m), 3.87-3.92 (4H, m), 4.51 (1H, m), 6.95 (1H, t), 7.39-7.40 (1H, m), 7.50-7.51 (1H, m), 8.34 (1H, d), 8.53 (1H, d); m/z 532 (M+H⁺)

The preparation of 5-chloro-N,N-dimethyl-pyrazine-2-carboxamide was described previously.

Methyl 3-hydroxy-5-[(2S)-1-tripropan-2-ylsilyloxypropan-2-yl]oxy-benzoate

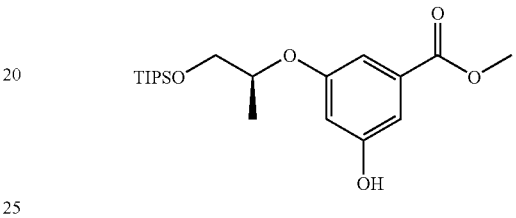

To a solution of methyl 3-phenylmethoxy-5-[(2S)-1-tripropan-2-ylsilyloxypropan-2-yl]oxy-benzoate (CAS no. 871657-71-5) (47.3 g, 0.1 mol) in ethanol (500 mL) was added 10% palladium on activated carbon (5 g) under a blanket of nitrogen. The reaction was stirred under an atmosphere of hydrogen for 16 hours. After this time the catalyst was filtered off and the solvent evaporated under reduced pressure afford the product (38.1 g, 100%). ¹H NMR δ (CDCl₃) 1.01-1.12 (22H, m), 1.32 (3H, d), 3.69-3.77 (2H, m), 3.89 (3H, s), 4.48 (1H, q), 6.62 (1H, t), 7.10 (1H, d), 7.18 (1H, t); m/z 381 (M−H⁻)

A further alternative method for the preparation of 5-[3-[(2S)-1-(difluoromethoxy)propan-2-yl]oxy-5-[(5-methylpyrazin-2-yl)carbamoyl]phenoxy]-N,N-dimethyl-pyrazine-2-carboxamide is given below:

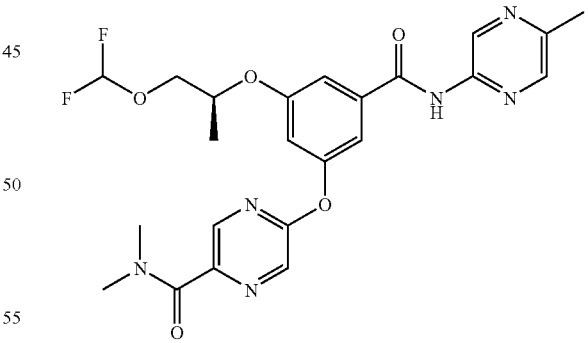

To 3-[(2S)-1-(difluoromethoxy)propan-2-yl]oxy-5-[5-(dimethylcarbamoyl)pyrazin-2-yl]oxy-benzoic acid (74.2 g, 180 mmol) was added DMF (1.4 mL, 18 mmol). Dichloromethane (810 mL) and oxalyl chloride (25.2 mL, 289 mmol) were charged and the reaction left to stir at ambient temperature for 2 hours. The solvent was evaporated under reduced pressure, azeotroped with toluene (2×600 mL) and the resulting oil dissolved in pyridine (392 ml) and dichloromethane (500 ml).

A solution of 5-methylpyrazin-2-amine (CAS no. 5521-58-4) (29.7 g, 272 mmol) in pyridine (549 mL) was charged dropwise to the stirred solution and the reaction stirred at ambient temperature for 20 hours. The solvent was evaporated under reduced pressure and the residue was taken up into ethyl acetate (1200 mL), washed with water (1200 mL), 1M citric acid (2×780 mL), saturated aqueous sodium hydrogen carbonate (2×780 mL), saturated aqueous brine (780 mL) and the combined organic extracts were dried (MgSO$_4$) and evaporated under reduced pressure the residue was purified by flash chromatography to afford the title compound (66 g).

To a sample of this material (64 g, 127 mmol) was added diethyl ether (640 mL) and the resulting slurry stirred overnight.

A solid was filtered, washed with diethyl ether (320 mL) and dried under vacuum at ambient temperature overnight to provide a white crystalline solid (56 g). This material had an X-ray powder diffraction pattern consistent with that described for 5-[3-[(2S)-1-(difluoromethoxy)propan-2-yl]oxy-5-[(5-methylpyrazin-2-yl)carbamoyl]phenoxy]-N,N-dimethyl-pyrazine-2-carboxamide Form A described previously. $^1$H NMR and mass spectrometry data were consistent with those described previously.

The preparation of 3-[(2S)-1-(difluoromethoxy)propan-2-yl]oxy-5-[5-(dimethylcarbamoyl)pyrazin-2-yl]oxy-benzoic acid is described below.

3-[(2S)-1-(difluoromethoxy)propan-2-yl]oxy-5-[5-(dimethylcarbamoyl)pyrazin-2-yl]oxy-benzoic acid

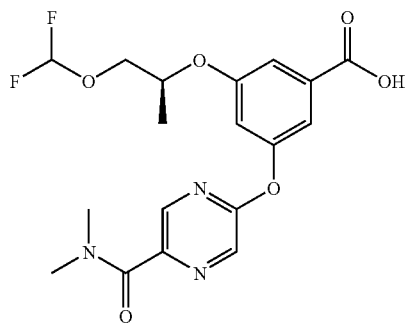

To methyl 3-[(2S)-1-(difluoromethoxy)propan-2-yl]oxy-5-[5-(dimethylcarbamoyl)pyrazin-2-yl]oxy-benzoate (76.3 g, 179 mmol) was added NMP (534 mL), water (305 mL) and the solution was stirred at 0° C. 2N sodium hydroxide (152 mL, 305 mmol) was charged dropwise and the reaction stirred for 4 hours. Acetic acid (41 mL, 718 mmol) was charged dropwise followed by water (1068 mL) and 1N HCl (400 mL) was added until pH 3 was reached and some material oiled out. The aqueous layer was extracted with toluene (3×988 mL) and combined with the material that oiled out which was dissolved in ethyl acetate (988 mL) and the combined organic layers were washed with water (988 mL), saturated aqueous brine (988 mL), dried (MgSO$_4$) and evaporated under reduced pressure. The residue was purified by flash chromatography eluting with 5% MeOH in dichloromethane to afford the title compound (64 g).

$^1$H NMR δ (DMSO-d$_6$) 1.27 (3H, d), 3.03 (6H, s), 3.99-4.04 (2H, m), 4.76-4.80 (1H, m), 6.52-6.91 (1H, t), 7.21 (1H, t), 7.34-7.38 (2H, m), 8.42 (1H, d), 8.56 (1H, d)

Methyl 3-[(2S)-1-(difluoromethoxy)propan-2-yl]oxy-5-[5-(dimethylcarbamoyl)pyrazin-2-yl]oxy-benzoate

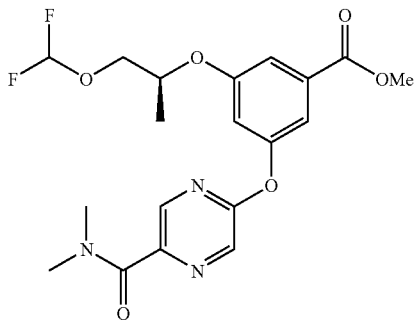

A solution of methyl 3-[5-(dimethylcarbamoyl)pyrazin-2-yl]oxy-5-[(2S)-1-hydroxypropan-2-yl]oxy-benzoate (94 g, 250 mmol) in acetonitrile (1130 mL) was degassed with nitrogen then copper(I) iodide (9.54 g, 50 mmol) was charged and the solution was heated to 55° C. A solution of 2,2-difluoro-2-fluorosulfonyl-acetic acid (CAS no. 1717-59-5) (46.6 mL, 450 mmol) in acetonitrile (188 mL) was charged dropwise. After 3 hours the solvent was evaporated under reduced pressure at 25° C. The residue was taken up in dichloromethane (500 mL) and filtered. The solid was washed further with dichloromethane until the washings were clear. The solvent was evaporated under reduced pressure at 25° C. and the residue was purified by flash chromatography eluting with 100% ethyl acetate to afford the title compound (54 g).

$^1$H NMR δ (DMSO-d$_6$) 1.28 (3H, d), 2.99-3.08 (6H, m), 3.86 (3H, s), 3.98-4.07 (2H, m), 4.78-4.82 (1H, m), 6.50-6.90 (1H, t), 7.25 (1H, t), 7.38-7.40 (2H, m), 8.42 (1H, d), 8.55 (1H, d)

Methyl 3-[5-(dimethylcarbamoyl)pyrazin-2-yl]oxy-5-[(2S)-1-hydroxypropan-2-yl]oxy-benzoate

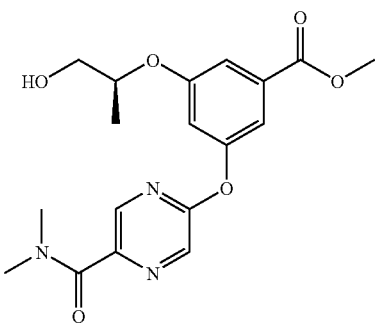

A solution of methyl 3-[5-(dimethylcarbamoyl)pyrazin-2-yl]oxy-5-[(2S)-1-[(2-methylpropan-2-yl)oxy]propan-2-yl]oxy-benzoate (170 g, 0.39 mol) in formic acid (850 mL) was heated to 90° C. for 3 hours. Ethyl acetate (1700 mL), water (1700 mL) and saturated aqueous brine (850 mL) was added and the aqueous layer separated and extracted with ethyl acetate (850 mL) and the combined organic layers were washed with saturated aqueous brine (850 mL), dried (MgSO$_4$) and evaporated under reduced pressure. The residue was dissolved with ethyl acetate (1500 mL), water (1500 mL) and methanol (150 mL). Sodium carbonate (170 g) was added and the biphasic solution heated to reflux for 2 hours. The aqueous layer was separated and the organic layer washed with water (1700 mL). The combined aqueous phases were extracted with ethyl acetate (850 mL) and the combined organic layers dried (MgSO₄) and evaporated under reduced pressure. The residue was purified by flash chromatography eluting with 100% ethyl acetate to obtain a the title compound (148 g).

¹H NMR δ (DMSO-d₆) 1.23 (3H, d), 3.04 (6H, s), 3.47-3.56 (2H, m), 3.86 (3H, s), 4.49-4.53 (1H, m), 4.86 (1H, t), 7.19 (1H, t), 7.34-7.35 (1H, m), 7.38-7.39 (1H, m), 8.42 (1H, d), 8.55 (1H, d)

Methyl 3-[5-(dimethylcarbamoyl)pyrazin-2-yl]oxy-5-[(2S)-1-[(2-methylpropan-2-yl)oxy]propan-2-yl]oxy-benzoate

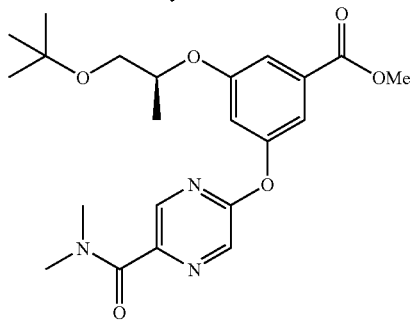

To methyl 3-[5-(dimethylcarbamoyl)pyrazin-2-yl]oxy-5-hydroxy-benzoate (10 g, 32 mmol) was added triphenylphosphine (10.3 g, 39.4 mmol), THF (100 mL) and (2R)-1-[(2-methylpropan-2-yl)oxy]propan-2-ol (CAS no. 136656-73-0) (5.21 g, 39.4 mmol). The resulting slurry was cooled to 0° C. and diethylazodicarboxylate (50% w/v in toluene, 13.7 mL, 39.4 mmol) was charged dropwise keeping the temperature below 10° C. After 2 hours the solvent was evaporated under reduced pressure and taken up with ethyl acetate (23 mL). A solid crashed out which was filtered and the mother liquors were evaporated under reduced pressure, taken up into ethyl acetate (23 mL) and isohexane (53 mL) and the resulting solid filtered, the mother liquors were evaporated under reduced pressure and the resulting residue was purified by flash chromatography eluting with 80% ethyl acetate/20% isohexane to afford the product (13.5 g).

¹H NMR δ (DMSO-d₆) 1.12 (9H, s), 1.25 (3H, d), 3.03 (6H, s), 3.41-3.45 (1H, m), 3.47-3.51 (1H, m), 3.85 (3H, s), 4.55-4.57 (1H, m), 7.20 (1H, t), 7.34-7.35 (1H, m), 7.40-7.41 (1H, m), 8.41 (1H, d), 8.54 (1H, d)

Methyl 3-[5-(dimethylcarbamoyl)pyrazin-2-yl]oxy-5-hydroxy-benzoate

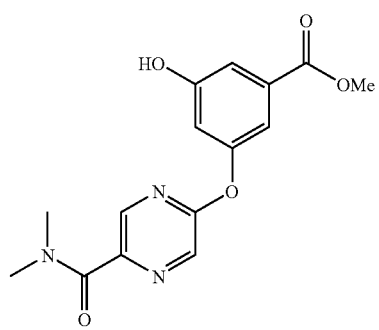

To methyl 3,5-dihydroxybenzoate (CAS no. 2150-44-9) (85 g, 0.49 mol) was added 5-chloro-N,N-dimethyl-pyrazine-2-carboxamide (88.9 g, 0.48 mol), DMSO (1000 mL,) and cesium carbonate (418 g, 1.2 mol) and the mixture was heated to 50° C. for 3 hours. Water (1577 mL,) was charged followed by diethyl ether (540 mL). To the aqueous layer was charged 5M hydrochloric acid solution (395 mL, 1.97 mol) and the resulting white solid was filtered washed with water (2×311 mL) and dried under vacuum at 40° C. over P₂O₅ overnight to give the desired compound (143 g).

¹H NMR δ (DMSO-d₆) 3.03 (6H, s), 3.84 (3H, s), 6.92 (1H, t), 7.21-7.22 (1H, m), 7.28-7.29 (1H, m), 8.41 (1H, d), 8.53 (1H, d), 10.20 (1H, s).

The preparation of 5-chloro-N,N-dimethyl-pyrazine-2-carboxamide was described previously.

EXAMPLE 3

5-[3-[(2S)-1-(Difluoromethoxy)propan-2-yl]oxy-5-(1H-pyrazol-3-ylcarbamoyl)phenoxy]-N,N-dimethyl-pyrazine-2-carboxamide

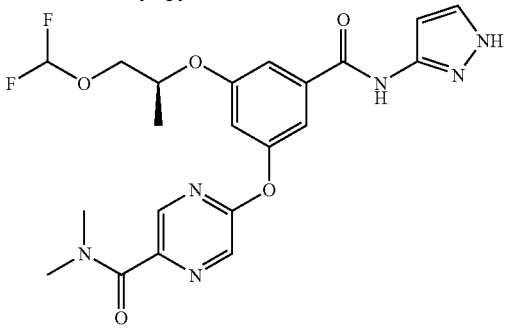

Trifluoroacetic acid (2 mL) was added to a solution of tert-butyl 3-[[3-[(2S)-1-(difluoromethoxy)propan-2-yl]oxy-5-[5-(dimethylcarbamoyl)pyrazin-2-yl]oxy-benzoyl]amino]pyrazole-1-carboxylate (150 mg, 0.26 mmol) in DCM (16 mL) and stirred at RT for 2 hours. The solvent was removed in vacuo, DCM (20 mL) added and the mixture washed with water (20 mL), saturated sodium bicarbonate solution (20 mL), brine (20 mL), dried (MgSO₄) and reduced in vacuo to give the desired compound (94 mg).

¹H NMR δ (CDCl₃): 1.38 (d, 3H), 3.15 (s, 3H), 3.18 (s, 3H), 3.95-4.03 (m, 2H), 4.62-4.69 (m, 1H), 6.25 (t, 1H), 6.84 (s, 1H), 6.92 (t, 1H), 7.31 (s, 1H), 7.37 (s, 1H), 7.44 (d, 1H), 8.39 (d, 1H), 8.49 (d, 1H), 9.71 (s, 1H), 10.04 (s, 1H); m/z 477 (M+H)⁺

EXAMPLE 4

3-[(2S)-1-(difluoromethoxy)propan-2-yl]oxy-5-(6-methylsulfonylpyridin-3-yl)oxy-N-(1H-pyrazol-3-yl)benzamide

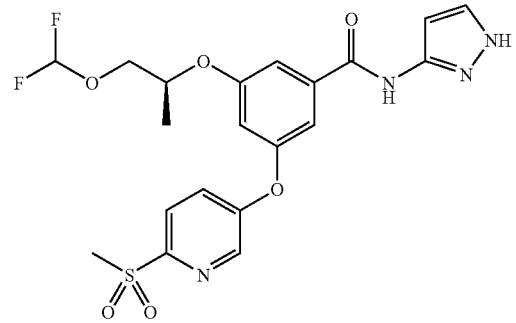

The following compound was prepared in an analogous fashion to example 3 from tert-butyl 3-[[3-[(2S)-1-(difluo romethoxy)propan-2-yl]oxy-5-(6-methylsulfonylpyridin-3-yl)oxy-benzoyl]amino]pyrazole-1-carboxylate.

¹H NMR δ (CDCl₃): 1.39 (d, 3H), 3.23 (s, 3H), 3.95-4.04 (m, 2H), 4.64-4.71 (m, 1H), 6.26 (t, 1H), 6.83-6.86 (m, 2H), 7.19 (s, 1H), 7.35 (s, 1H), 7.45-7.48 (m, 1H), 7.52 (s, 1H), 8.07 (d, 1H), 8.48 (d, 1H), 8.65 (s, 1H); m/z 483 (M+H)⁺

1H), 8.01 (d, 1H), 8.37 (d, 1H), 8.53 (d, 1H), 8.97 (s, 1H); m/z 577 (M+H)⁺ tert-Butyl 3-[[3-[(2S)-1-(difluoromethoxy)propan-2-yl]oxy-5-(6-methylsulfonylpyridin-3-yl)oxy-benzoyl]amino]pyrazole-1-carboxylate, used in the preparation of Example 4, was prepared in an analogous fashion from 3-[(2S)-1-(difluoromethoxy)propan-2-yl]oxy-5-(6-methylsulfonylpyridin-3-yl)oxy-benzoic acid.

| Structure | m/z | NMR |
|---|---|---|
| 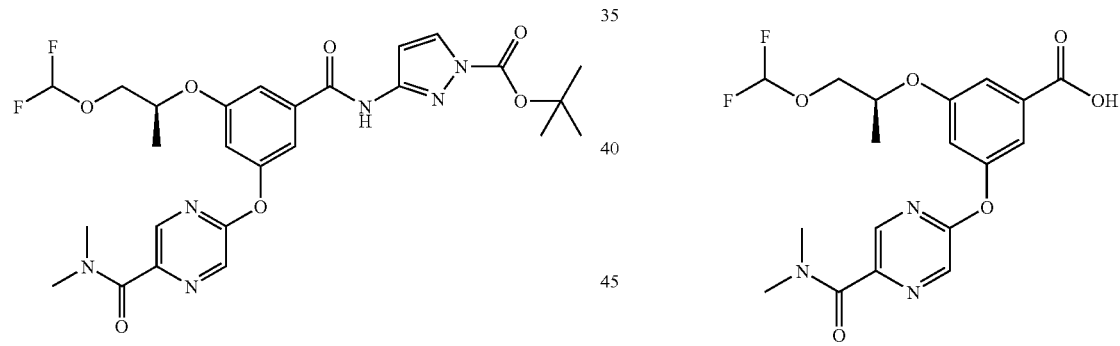 | 583 (M+H)⁺ | ¹H NMR δ (CDCl₃): 1.39(d, 3 H), 1.64(s, 9 H), 3.24(s, 3 H), 3.95-4.04(m, 2 H), 4.64-4.68(m, 1 H), 6.26(t, 1 H), 6.85(t, 1 H), 7.07(d, 1 H), 7.14(t, 1 H), 7.30(t, 1 H), 7.46-7.48(m, 1 H), 8.01 (d, 1 H), 8.09(d, 1 H), 8.48 (d, 1 H), 8.67(s, 1 H) | tert-Butyl 3-[[3-[(2S)-1-(difluoromethoxy)propan-2-yl]oxy-5-(6-methylsulfonylpyridin-3-yl)oxy-benzoyl]amino]pyrazole-1-carboxylate 3-[(2S)-1-(difluoromethoxy)propan-2-yl]oxy-5-[5-(dimethylcarbamoyl)pyrazin-2-yl]oxy-benzoic acid 1-Chloro-N,N,2-trimethyl-prop-1-en-1-amine (0.11 mL, 0.80 mmol) was added to a solution of 3-[(2S)-1-(difluoromethoxy)propan-2-yl]oxy-5-[5-(dimethylcarbamoyl)pyrazin-2-yl]oxy-benzoic acid (0.22 g, 0.53 mmol) in DCM (5 mL) and stirred for 1 hour. tert-Butyl 3-aminopyrazole-1-carboxylate (CAS no. 863504-94-1) (147 mg, 0.80 mmol) then pyridine (0.09 mL, 1.07 mmol) were added and the reaction stirred for a further 45 minutes before being reduced in vacuo and partitioned between ethyl acetate (50 mL) and water (50 mL). The aqueous layer was further extracted into ethyl acetate (50 mL) and the combined organics washed with water (50 mL), brine (50 mL), dried (MgSO₄), and reduced in vacuo. The crude residue was chromatographed on silica, eluting with 20-50% ethyl acetate in isohexane, to give the desired compound (0.15 g).

¹H NMR δ (CDCl₃): 1.38 (d, 3H), 1.60 (s, 9H), 3.16 (s, 3H), 3.19 (s, 3H), 3.93-4.04 (m, 2H), 4.60-4.64 (m, 1H), 6.26 (t, 1H), 6.95 (t, 1H), 7.09 (d, 1H), 7.27-7.28 (m, 1H), 7.34 (t,

Lithium hydroxide monohydrate (45 mg, 1.06 mol) in water (5 mL) was added to a solution of methyl 3-[(2S)-1-(difluoromethoxy)propan-2-yl]oxy-5-[5-(dimethylcarbamoyl)pyrazin-2-yl]oxy-benzoate (0.3 g, 0.71 mmol) in THF (10 mL) and stirred at RT for 20 hours. The THF was removed in vacuo and the aqueous layer was washed with ethyl acetate (50 mL) to remove any impurities. The aqueous layer was acidified and extracted into ethyl acetate (2×50 mL) then the combined organics washed with brine (50 mL), dried (MgSO₄) and the solvent removed in vacuo to give the desired compound (0.22 g).

¹H NMR δ (CDCl₃): 1.39 (d, 3H), 3.17 (s, 3H), 3.19 (s, 3H), 3.93-4.05 (m, 2H), 4.60-4.69 (m, 1H), 6.26 (t, 1H), 6.99 (t, 1H), 7.50-7.55 (m, 2H), 8.38 (d, 1H), 8.55 (d, 1H), 10.17 (s, 1H); m/z 412 (M+H)⁺

Methyl 3-[(2S)-1-(difluoromethoxy)propan-2-yl]oxy-5-[5-(dimethylcarbamoyl)pyrazin-2-yl]oxy-benzoate

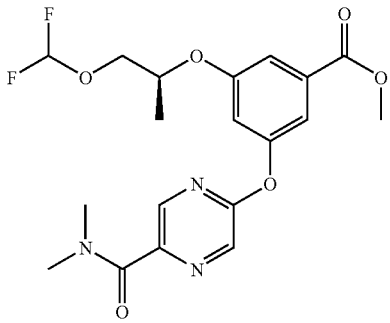

A mixture of methyl 3-[(2S)-1-(difluoromethoxy)propan-2-yl]oxy-5-hydroxy-benzoate (0.25 g, 0.91 mmol), 5-chloro-N,N-dimethyl-pyrazine-2-carboxamide (168 mg, 0.91 mmol) and potassium carbonate (250 mg, 1.81 mmol) in acetonitrile (5 mL) was stirred in a microwave reactor at 140° C. for 5 hours. The mixture was reduced in vacuo and ethyl acetate (50 mL) added. The mixture was washed with water (50 mL), brine (50 mL), dried (MgSO$_4$) and reduced in vacuo. The residue was chromatographed on silica, eluting with 20 to 70% ethyl acetate in isohexane, to give the desired compound (0.3 g).

$^1$H NMR δ (CDCl$_3$): 1.38 (d, 3H), 3.15 (s, 3H), 3.18 (s, 3H), 3.91 (s, 3H), 3.93-4.04 (m, 2H), 4.61-4.69 (m, 1H), 6.26 (t, 1H), 6.96 (t, 1H), 7.44-7.45 (m, 1H), 7.50-7.51 (m, 1H), 8.36 (d, 1H), 8.53 (d, 1H); m/z 426 (M+H)$^+$

The preparation of 5-chloro-N,N-dimethyl-pyrazine-2-carboxamide was described earlier.

Methyl 3-[(2S)-1-(difluoromethoxy)propan-2-yl]oxy-5-hydroxy-benzoate

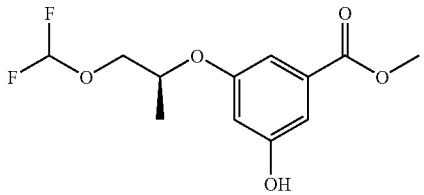

Methyl 3-[(2S)-1-(difluoromethoxy)propan-2-yl]oxy-5-phenylmethoxy-benzoate (0.48 g, 1.1 mmol) was dissolved in ethanol (10 mL) and THF (10 mL) and the flask evacuated and purged with argon (3 times). 10% Palladium on carbon (140 mg) was added and the flask further evacuated and finally purged with hydrogen gas. The reaction mixture was stirred at RT for 20 hours until completion. The reaction mixture was evacuated and purged with argon (3 times) then the catalyst removed by filtration through Celite®. The filtrate was concentrated in vacuo to give the desired compound (1.05 g).

$^1$H NMR δ (CDCl$_3$): 1.35 (d, 3H), 3.90 (s, 3H), 3.90-4.02 (m, 2H), 4.57-4.64 (m, 1H), 5.20 (s, 1H), 6.26 (t, 1H), 6.63 (t, 1H), 7.14-7.15 (m, 1H), 7.17-7.18 (m, 1H); m/z 275 (M−H)$^-$

The preparation of methyl 3-[(2S)-1-(difluoromethoxy)propan-2-yl]oxy-5-phenylmethoxy-benzoate was described earlier.

The preparation of 3-[(2S)-1-(difluoromethoxy)propan-2-yl]oxy-5-(6-methylsulfonylpyridin-3-yl)oxy-benzoic acid is described below. 3-[(2S)-1-(difluoromethoxy)propan-2-yl]oxy-5-(6-methylsulfonylpyridin-3-yl)oxy-benzoic acid

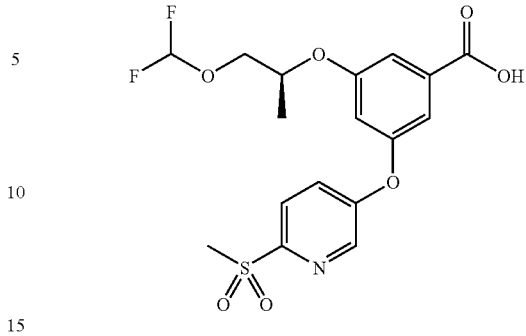

A mixture of methyl 3-[(2S)-1-(difluoromethoxy)propan-2-yl]oxy-5-hydroxy-benzoate (233 mg, 0.84 mmol), 5-bromo-2-methylsulfonyl-pyridine (CAS no. 98626-95-0) (200 mg, 0.84 mmol), cesium carbonate (549 mg, 1.69 mmol) and bromotris(triphenylphosphine)copper(I) (157 mg, 0.17 mmol) in DMA (5 mL) was stirred in a microwave reactor at 160° C. for 6 hours. Ethyl acetate (50 mL) and water were added and the aqueous layer was acidified and extracted with ethyl acetate (2×50 mL). The combined organics were washed with brine, dried (MgSO$_4$) and reduced in vacuo to give the desired compound (0.16 g).

$^1$H NMR δ (d$_6$-DMSO): 1.28 (d, 3H), 3.27 (s, 3H), 3.95-4.04 (m, 2H), 4.78-4.85 (m, 1H), 6.71 (t, 1H), 7.14-7.16 (m, 1H), 7.22-7.23 (m, 1H), 7.37-7.40 (m, 1H), 7.66-7.70 (m, 1H), 8.06 (d, 1H), 8.61 (d, 1H), 12.85 (s, 1H); m/z 418 (M+H)$^+$

The preparation of methyl 3-[(2S)-1-(difluoromethoxy)propan-2-yl]oxy-5-hydroxy-benzoate was described earlier.

EXAMPLE 5

5-[3-[(2S)-1-(difluoromethoxy)propan-2-yl]oxy-5-[(1-methylpyrazol-3-yl)carbamoyl]phenoxy]-N,N-dimethyl-pyrazine-2-carboxamide

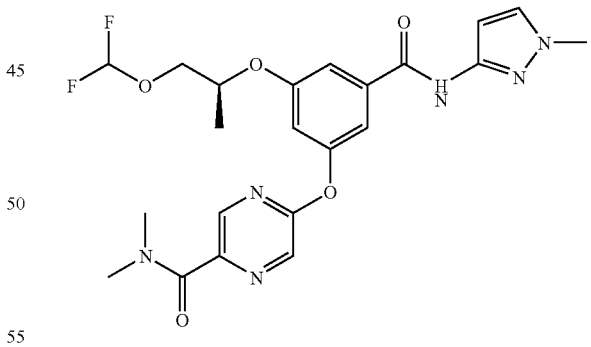

A mixture of 3-[(2S)-1-(difluoromethoxy)propan-2-yl]oxy-5-hydroxy-N-(1-methylpyrazol-3-yl)benzamide (0.1 g, 0.29 mmol), 5-chloro-N,N-dimethyl-pyrazine-2-carboxamide (66 mg, 0.35 mmol) and potassium carbonate (81 mg, 0.59 mmol) in acetonitrile (5 mL) was stirred in a microwave reactor at 160° C. for 6 hours. The resulting mixture was reduced in vacuo and ethyl acetate (50 mL) added. The organics were washed with water (50 mL), brine (50 mL), dried (MgSO$_4$), filtered and reduced in vacuo. The residue was chromatographed on silica, eluting with 10-100% ethyl acetate in isohexane to give the desired compound (52 mg).

$^1$H NMR δ (CDCl$_3$): 1.30 (d, 3H), 3.08 (s, 3H), 3.11 (s, 3H), 3.69 (s, 3H), 3.85-3.97 (m, 2H), 4.56 (sextet, 1H), 6.18 (t, 1H), 6.73 (d, 1H), 6.85 (t, 1H), 7.19-7.21 (m, 2H), 7.27-7.29 (m, 1H), 8.29 (d, 1H), 8.45 (d, 1H), 8.76 (s, 1H); m/z 491 (M+H)$^+$ The synthesis of 5-chloro-N,N-dimethyl-pyrazine-2-carboxamide was described previously.

3-[(2S)-1-(difluoromethoxy)propan-2-yl]oxy-5-hydroxy-N-(1-methylpyrazol-3-yl)benzamide

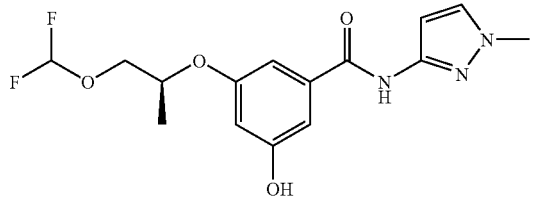

3-[(2S)-1-(difluoromethoxy)propan-2-yl]oxy-N-(1-methylpyrazol-3-yl)-5-phenylmethoxy-benzamide (0.1 g, 0.23 mmol) was dissolved in ethanol (3 mL) and THF (3 mL) and the flask evacuated and purged with argon (3 times). 10% Palladium on carbon (0.01 g) was added and the flask further evacuated and finally purged with hydrogen gas. The reaction mixture was stirred at RT for 20 hours until completion. The reaction mixture was evacuated and purged with nitrogen (3 times). The catalyst was filtered off through celite and the filtrate concentrated in vacuo to give the desired compound (70 mg).
$^1$H NMR δ (CDCl$_3$): 1.28 (d, 3H), 3.71 (s, 3H), 3.80-3.95 (m, 2H), 4.51 (sextet, 1H), 5.96-6.36 (t, 1H), 6.53 (s, 1H), 6.73 (s, 1H), 6.91 (s, 1H), 6.96 (s, 1H), 7.22 (s, 1H), 8.83 (s, 1H); m/z 342 (M+H)$^+$ 3-[(2S)-1-(difluoromethoxy)propan-2-yl]oxy-N-(1-methylpyrazol-3-yl)-5-phenylmethoxy-benzamide

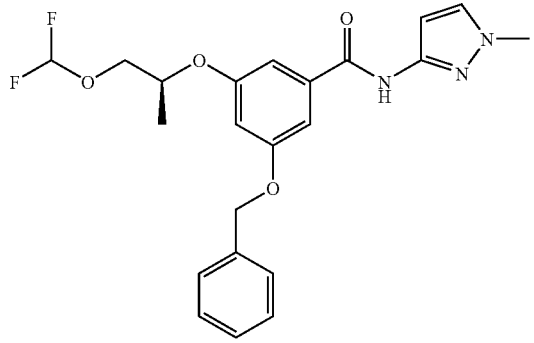

DIPEA (0.198 mL, 1.14 mmol) was added to a mixture of 3-[(2S)-1-(difluoromethoxy)propan-2-yl]oxy-5-phenylmethoxy-benzoic acid (0.10 g, 0.28 mmol), 1-methylpyrazol-3-amine (CAS no. 1904-31-0) (39 mg, 0.4 mmol) and HATU (0.227 g, 0.6 mmol) in DMF (3 mL) and stirred at RT for 20 hours. Ethyl acetate (30 mL) was added and the mixture washed with water (30 mL), brine (30 mL), dried (MgSO$_4$), filtered and reduced in vacuo. The residue was chromatographed on silica, eluting with a gradient of 0-100% ethyl acetate in isohexane, to give the desired compound (0.1 g).
$^1$H NMR δ (CDCl$_3$): 1.36 (d, 3H), 3.68 (s, 3H), 3.82-3.95 (m, 2H), 4.48 (sextet, 1H), 5.00 (s, 2H), 6.19 (t, 1H), 6.63 (s, 1H), 6.73 (s, 1H), 6.93 (s, 1H), 7.03 (s, 1H), 7.28 (m, 1H), 7.35 (m, 5H), 8.59 (s, 1H); m/z 432 (M+H)$^+$ The synthesis of 3-[(2S)-1-(difluoromethoxy)propan-2-yl]oxy-5-phenylmethoxy-benzoic acid was described earlier.

EXAMPLE 6

3-[(2S)-1-(difluoromethoxy)propan-2-yl]oxy-N-(1-methylpyrazol-3-yl)-5-(6-methylsulfonylpyridin-3-yl)oxy-benzamide

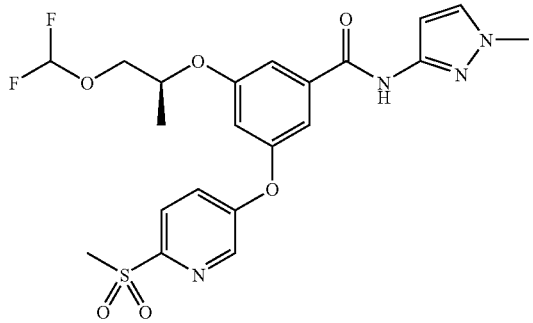

A mixture of 3-[(2S)-1-(difluoromethoxy)propan-2-yl]oxy-5-hydroxy-N-(1-methylpyrazol-3-yl)benzamide (100 mg, 0.29 mmol), 5-bromo-2-methylsulfonyl-pyridine (CAS no. 98626-95-0) (77 mg, 0.32 mmol), cesium carbonate (191 mg, 0.59 mmol) and bromotris(triphenylphosphine)copper(I) (55 mg, 0.06 mmol) in DMA (5 mL) was stirred in a microwave reactor at 160° C. for 6 hours. Ethyl acetate (50 mL) was added and washed with water (50 mL), brine (50 mL), dried (MgSO$_4$), filtered and reduced in vacuo. The residue was chromatographed on silica, eluting with 10-80% ethyl acetate in isohexane to give the desired compound (31 mg).
$^1$H NMR δ (CDCl$_3$): 1.30 (d, 3H), 3.16 (s, 3H), 3.72 (s, 3H), 3.85-3.95 (m, 2H), 4.53-4.59 (m, 1H), 6.18 (t, 1H), 6.71 (d, 1H), 6.75 (t, 1H), 7.09 (t, 1H), 7.22 (d, 1H), 7.25 (t, 1H), 7.37-7.39 (m, 1H), 7.99 (d, 1H), 8.39 (d, 1H), 8.62 (s, 1H); m/z 495 (M−H)$^-$ The synthesis of 3-[(2S)-1-(difluoromethoxy)propan-2-yl]oxy-5-hydroxy-N-(1-methylpyrazol-3-yl)benzamide was described previously.

Biological

Tests:

The biological effects of the compounds of formula (I) may be tested in the following way:

(1) Enzymatic Activity

Enzymatic activity of recombinant human pancreatic GLK may be measured by incubating GLK, ATP and glucose. The rate of product formation may be determined by coupling the assay to a G-6-P dehydrogenase, NADP/NADPH system and measuring the linear increase with time of optical density at 340 nm Brocklehurst et al (Diabetes 2004, 53, 535-541). Activation of GLK by compounds can be assessed using this assay in the presence or absence of GLKRP as described in Brocklehurst et al (Diabetes 2004, 53, 535-541).

Compounds of the invention were assessed in the absence of GLKRP as described by Brocklehurst et al and activated glucokinase with EC$_{50}$ values as shown below.

TABLE C

| Example Number | EC$_{50}$ Value (μM) |
|---|---|
| 1 | 0.069 |
| 2 | 0.055 |
| 3 | 0.065 |

TABLE C-continued

| Example Number | EC$_{50}$ Value (μM) |
|---|---|
| 4 | 0.033 |
| 5 | 0.079 |
| 6 | 0.077 |

Production of Recombinant GLK and GLKRP:

Human GLK and GLKRP cDNA was obtained by PCR from human pancreatic and hepatic mRNA respectively, using established techniques described in Sambrook J, Fritsch EF & Maniatis T, 1989. PCR primers were designed according to the GLK and GLKRP cDNA sequences shown in Tanizawa et al., Proc Natl Acad Sci 1991 Aug. 15; 88(16): 7294-7 and Warner et al., Mamm Genome. 1995 August; 6(8):532-6.

Cloning in Bluescript II Vectors

GLK and GLKRP cDNA was cloned in E. coli using pBluescript II,

Transformations

E. Coli transformations were generally carried out by electroporation. 400 mL cultures of strains DH5a or BL21(DE3) were grown in L-broth to an OD 600 of 0.5 and harvested by centrifugation at 2,000 g. The cells were washed twice in ice-cold deionised water, resuspended in 1 mL 10% glycerol and stored in aliquots at −70° C. Ligation mixes were desalted using Millipore V Series™ membranes (0.0025 mm) pore size). 40 mL of cells were incubated with 1 mL of ligation mix or plasmid DNA on ice for 10 minutes in 0.2 cm electroporation cuvettes, and then pulsed using a Gene Pulser™ apparatus (BioRad) at 0.5 kVcm$^{-1}$, 250 mF. Transformants were selected on L-agar supplemented with tetracyline at 10 mg/mL or ampicillin at 100 mg/mL.

Expression

GLK was expressed from the vector pTB375NBSE in E. coli BL21 cells, producing a recombinant protein containing a 6-His tag immediately adjacent to the N-terminal methionine. Alternatively, another suitable vector is pET21(+)DNA, Novagen, Cat number 697703. The 6-His tag was used to allow purification of the recombinant protein on a column packed with nickel-nitrilotriacetic acid agarose purchased from Qiagen (cat no 30250).

GLKRP was expressed from the vector pFLAG CTC (IBI Kodak) in E. coli BL21 cells, producing a recombinant protein containing a C-terminal FLAG tag. The protein was purified initially by DEAE Sepharose ion exchange followed by utilisation of the FLAG tag for final purification on an M2 anti-FLAG immunoaffinity column purchased from Sigma-Aldrich (cat no. A1205).

(2) Oral Glucose Tolerance Test (OGTT)

Oral glucose tolerance tests (G. J Coope et al, British Journal of Pharmacology, (2006) 149, 328-335) may be performed on conscious Zucker obese fa/fa rats (age 12-13 weeks or older) fed a high fat diet (45% kcal fat) for at least two weeks prior to experimentation. The animals are fasted for 2 hours before use for experiments. A test compound or a vehicle is given orally 120 minutes before oral administration of a glucose solution at a dose of 2 g/kg body weight. Blood glucose levels are measured using a Accucheck glucometer from tail bled samples taken at different time points before and after administration of glucose (time course of 60 minutes). A time curve of the blood glucose levels is generated and the area-under-the-curve (AUC) for 120 minutes calculated (the time of glucose administration being time zero). Percent reduction in glucose excursion is determined using the AUC in the vehicle-control group as zero percent reduction.

REFERENCES

1. Printz, R. L., Magnuson, M. A. and Granner, D. K. (1993) Annual Review of Nutrition 13, 463-96
2. DeFronzo, R. A. (1988) Diabetes 37, 667-87
3. Froguel, P., Zouali, H., Vionnet, N., Velho, G., Vaxillaire, M., Sun, F., Lesage, S., Stoffel, M., Takeda, J. and Passa, P. (1993) New England Journal of Medicine 328, 697-702
4. Bell, G. I., Pilkis, S. J., Weber, I. T. and Polonsky, K. S. (1996) Annual Review of Physiology 58, 171-86
5. Velho, G., Petersen, K. F., Perseghin, G., Hwang, J. H., Rothman, D. L., Pueyo, M. E., Cline, G. W., Froguel, P. and Shulman, G. I. (1996) Journal of Clinical Investigation 98, 1755-61
6. Christesen, H. B., Jacobsen, B. B., Odili, S., Buettger, C., Cuesta-Munoz, A., Hansen, T., Brusgaard, K., Massa, O., Magnuson, M. A., Shiota, C., Matschinsky, F. M. and Barbetti, F. (2002) Diabetes 51, 1240-6
6a. Gloyn, A. L., Noordam, K., Willemsen, M. A. A. P., Ellard, S., Lam, W. W. K., Campbell, I. W., Midgley, P., Shiota, C., Buettger, C., Magnuson, M. A., Matschinsky, F. M., and Hattersley, A. T.; Diabetes 52: 2433-2440
7. Glaser, B., Kesavan, P., Heyman, M., Davis, E., Cuesta, A., Buchs, A., Stanley, C. A., Thornton, P. S., Permutt, M. A., Matschinsky, F. M. and Herold, K. C. (1998) New England Journal of Medicine 338, 226-30
8. Caro, J. F., Triester, S., Patel, V. K., Tapscott, E. B., Frazier, N. L. and Dohm, G. L. (1995) Hormone & Metabolic Research 27, 19-22
9. Desai, U. J., Slosberg, E. D., Boettcher, B. R., Caplan, S. L., Fanelli, B., Stephan, Z., Gunther, V. J., Kaleko, M. and Connelly, S. (2001) Diabetes 50, 2287-95
10. Shiota, M., Postic, C., Fujimoto, Y., Jetton, T. L., Dixon, K., Pan, D., Grimsby, J., Grippo, J. F., Magnuson, M. A. and Chemington, A. D. (2001) Diabetes 50, 622-9
11. Ferre, T., Pujol, A., Riu, E., Bosch, F. and Valera, A. (1996) Proceedings of the National Academy of Sciences of the United States of America 93, 7225-30
12. Seoane, J., Barbera, A., Telemaque-Potts, S., Newgard, C. B. and Guinovart, J. J. (1999) Journal of Biological Chemistry 274, 31833-8
13. Moore, M. C., Davis, S, N., Mann, S. L. and Chemington, A. D. (2001) Diabetes Care 24, 1882-7
14. Alvarez, E., Roncero, I., Chowen, J. A., Vazquez, P. and Blazquez, E. (2002) Journal of Neurochemistry 80, 45-53
15. Lynch, R. M., Tompkins, L. S., Brooks, H. L., Dunn-Meynell, A. A. and Levin, B. E. (2000) Diabetes 49, 693-700
16. Roncero, I., Alvarez, E., Vazquez, P. and Blazquez, E. (2000) Journal of Neurochemistry 74, 1848-57
17. Yang, X. J., Kow, L. M., Funabashi, T. and Mobbs, C. V. (1999) Diabetes 48, 1763-1772
18. Schuit, F. C., Huypens, P., Heimberg, H. and Pipeleers, D. G. (2001) Diabetes 50, 1-11
19. Levin, B. E. (2001) International Journal of Obesity 25, supplement 5, S68-S72.
20. Alvarez, E., Roncero, I., Chowen, J. A., Thorens, B. and Blazquez, E. (1996) Journal of Neurochemistry 66, 920-7
21. Mobbs, C. V., Kow, L. M. and Yang, X. J. (2001) American Journal of Physiology—Endocrinology & Metabolism 281, E649-54

22 Levin, B. E., Dunn-Meynell, A. A. and Routh, V. H. (1999) American Journal of Physiology 276, R1223-31
23 Spanswick, D., Smith, M. A., Groppi, V. E., Logan, S. D. and Ashford, M. L. (1997) Nature 390, 521-5
24 Spanswick, D., Smith, M. A., Mirshamsi, S., Routh, V. H. and Ashford, M. L. (2000) Nature Neuroscience 3, 757-8
25 Levin, B. E. and Dunn-Meynell, A. A. (1997) Brain Research 776, 146-53
26 Levin, B. E., Govek, E. K. and Dunn-Meynell, A. A. (1998) Brain Research 808, 317-9
27 Levin, B. E., Brown, K. L. and Dunn-Meynell, A. A. (1996) Brain Research 739, 293-300
28 Rowe, I. C., Boden, P. R. and Ashford, M. L. (1996) Journal of Physiology 497, 365-77
29 Fujimoto, K., Sakata, T., Arase, K., Kurata, K., Okabe, Y. and Shiraishi, T. (1985) Life Sciences 37, 2475-82
30 Kurata, K., Fujimoto, K. and Sakata, T. (1989) Metabolism: Clinical & Experimental 38, 46-51
31 Kurata, K., Fujimoto, K., Sakata, T., Etou, H. and Fukagawa, K. (1986) Physiology & Behavior 37, 615-20
32 Jetton T. L., Liang Y., Pettepher C. C., Zimmerman E. C., Cox F. G., Horvath K., Matschinsky F. M., and Magnuson M. A., J. Biol. Chem., February 1994; 269: 3641-3654
33 Reimann F. and Gribble F. M., Diabetes 2002 51: 2757-2763
34 Cheung A. T., Dayanandan B., Lewis J. T., Korbutt G. S., Rajotte R. V., Bryer-Ash M., Boylan M. O., Wolfe M. M., Kieffer T. J., Science, Vol 290, Issue 5498, 1959-1962, 8 Dec. 2000

The invention claimed is:

1. The compound 5-[3-[(2S)-1-(difluoromethoxy)propan-2-yl]oxy-5-[(5-methylpyrazin-2-yl)carbamoyl]phenoxy]-N,N-dimethyl-pyrazine-2-carboxamide or a salt thereof.

2. A pharmaceutical composition comprising the compound 5-[3-[(2S)-1-(difluoromethoxy)propan-2-yl]oxy-5-[(5-methylpyrazin-2-yl)carbamoyl]phenoxy]-N,N-dimethyl-pyrazine-2-carboxamide or a pharmaceutically-acceptable salt thereof, together with a pharmaceutically acceptable diluent or carrier.

3. A process for the preparation of the compound 5-[3-[(2S)-1-(difluoromethoxy)propan-2-yl]oxy-5-[(5-methylpyrazin-2-yl)carbamoyl]phenoxy]-N,N-dimethyl-pyrazine-2-carboxamide or a salt thereof comprising:
  i) reacting 3-[(2S)-1-(difluoromethoxy)propan-2-yl]oxy-5-hydroxy-N-(5-methylpyrazin-2-yl)benzamide with 5-chloro-N,N-dimethyl-pyrazine-2-carboxamide; or
  ii) reacting 3-[(2S)-1-(difluoromethoxy)propan-2-yl]oxy-5-[5-(dimethylcarbamoyl)pyrazin-2-yl]oxy-benzoic acid or an activated derivative thereof with 5-methylpyrazin-2-amine;

and thereafter optionally forming a salt thereof.

* * * * *